(12) United States Patent
Murphy et al.

(10) Patent No.: US 7,683,097 B2
(45) Date of Patent: Mar. 23, 2010

(54) TOPOISOMERASE INHIBITORS

(75) Inventors: Martin A. Murphy, St. Helena, CA (US); John Robert Schullek, Santa Clara, CA (US); John S. Ward, Redwood City, CA (US); Gary C. Look, Santa Clara, CA (US); Brian Siesel, San Francisco, CA (US)

(73) Assignee: Propharmacon Inc., San Jose, CA (US)

( * ) Notice: Subject to any disclaimer, the term of this patent is extended or adjusted under 35 U.S.C. 154(b) by 887 days.

(21) Appl. No.: 11/138,636

(22) Filed: May 25, 2005

(65) Prior Publication Data

US 2007/0004701 A1 Jan. 4, 2007

Related U.S. Application Data

(60) Provisional application No. 60/575,141, filed on May 27, 2004.

(51) Int. Cl.
C07C 233/64 (2006.01)
C07D 251/12 (2006.01)
C07D 241/10 (2006.01)
C07D 239/24 (2006.01)
C07D 207/04 (2006.01)
C07D 213/02 (2006.01)
C07D 277/08 (2006.01)
C07D 307/04 (2006.01)
A61K 31/53 (2006.01)
A61K 31/505 (2006.01)
A61K 31/166 (2006.01)
A61K 31/34 (2006.01)
A61K 31/40 (2006.01)
A61K 31/44 (2006.01)
A61K 31/445 (2006.01)
A61K 31/4965 (2006.01)
A61P 35/00 (2006.01)

(52) U.S. Cl. .......... 514/615; 564/123; 564/181; 544/182; 544/242; 544/316; 544/336; 546/288; 546/304; 548/146; 548/400; 549/429; 514/242; 514/256; 514/269; 514/275; 514/345; 514/352; 514/315; 514/365; 514/408; 514/461

(58) Field of Classification Search .......... 564/123, 564/181; 514/615, 242, 252.1, 256, 269, 514/275, 345, 352, 365, 408, 461; 544/182, 544/242, 316, 336; 546/192, 288, 304; 548/146, 548/400; 549/429

See application file for complete search history.

(56) References Cited

U.S. PATENT DOCUMENTS 7,115,750 B1 * 10/2006 Kato et al. ............ 548/416
2002/0016336 A1 * 2/2002 Duan et al. ............ 514/314
2004/0058903 A1 * 3/2004 Takasugi et al. ........ 514/210.2

FOREIGN PATENT DOCUMENTS

WO WO-03/093248 A1 * 11/2003

OTHER PUBLICATIONS

Cecil Textbook of Medicine, edited by Bennet, J.C., and Plum F., 20th edition, vol. 1, 1004-1010, 1996.*
West, Anthony R., Solid State Chemistry and its Applications, Wiley, New York, 1988, pp. 358 & 365.*
Vippagunta et al., Advanced Drug Delivery Reviews 48: 3-26, 2001.*
Wolff Manfred E. "Burger's Medicinal Chemistry, 5ed, Part 1", John Wiley & Sons, 1995, pp. 975-977.*
Banker, G.S. et al, "Modern Pharmaceutics, 3ed.", Marcel Dekker, New York. 1996, pp. 451 and 596.*
Andoh et al., Advances in Pharmacology, 29B, 93-103, 1994.*
Denny et al., Expert Opin. Emerg. Drugs, 9(1), 105-133, 2004.*
Ruchelman et al., Biorganic & Medicinal Chemistry, 12, 795-806, 2004.*
Database CAPLUS on STN; Accession No. 1933-17784, DN:27:17784, "Symmetrical triad prototropic systems. IX. The influence of polynuclear aryl groups upon mobility and equilibrium in the alpha, delta diarylmethyleneazomethine system." Journal of the Chemical Society, Shoppe, Charles; 1993, pp. 37-45, See HCaplus 27:17784.
Nardi et al., "Synthesis and Anticonvulsant Activity of N-(Benzoylalkyl) imidazoles and N-(wPhenyl-w-hydroxyalkyl) imidazoles." J. Med. Chem., 1981, vol. 24, pp. 727-731.

* cited by examiner

*Primary Examiner*—Venkataraman Balasubramanian

(57) ABSTRACT

The present invention provides compounds that are effective against inhibiting topoisomerase (i.e., topoisomerase I and/or topoisomerase II). These compounds are used for treating cell-proliferative disorders. In some instances, these compounds have anticancer activity, e.g., against multi-drug resistant cancers.

5 Claims, 7 Drawing Sheets

TOPOISOMERASE INHIBITORS

CROSS REFERENCES TO RELATED APPLICATIONS

This application claims priority to U.S. Provisional Application No. 60/575,141, filed on May 27, 2004, the teaching of which is hereby incorporated by reference in its entirety for all purposes.

FIELD OF INVENTION

The present invention provides compounds, their pharmaceutical compositions and methods of use. These compounds have useful activity against cell-proliferative disorders.

BACKGROUND OF THE INVENTION

DNA topoisomerases that were first discovered in 1971 (Wang, J. C., *J Mol Biol.*, 55(3), 523-33, 1971) are essential enzymes in both prokaryotic and eukaryotic cells as they play key roles in genome topology maintenance. These nuclear enzymes catalyze DNA scission and religation reactions that either relax or supercoil DNA strands as well as remove knots and catenations, and in doing so produce different DNA topoisomers. They are believed to relieve torsional strain on DNA during replication and transcription processes. Because of their importance for cell viability, inhibitors of the topoisomerases (Topo) have been useful in treating cell proliferative conditions, in particular, human cancers because of the cytotoxicity they produce. The Topos have now been clearly identified as a validated molecular target for a variety of widely prescribed anticancer drugs (Pommier, Y., *Cancer Therapeutics: Experimental and Clinical Agents*, Teicher, B. A. ed., Humana Press, Totowan N.J., 153-174, 1997; Sausville, E., *Anticancer Drug Development Workshop, DTP & NCI*, N. Carolina, 2002). Collectively, the topoisomerase inhibitors comprise 6% of the total world market for cancer drugs in chemotherapy.

There are two general types of enzymes each of which has a different mechanism of DNA scission and different topological function, Topo I and II. The function of Topo I is to relax either positive or negative supercoiled DNA (Wang, J. C., *Annu. Rev. Biochem.*, 65, 635-692, 1996) by cutting one strand of the duplex DNA, followed by strand passage of the intact strand, and finally religating the cut strand. Topo I does not require ATP hydrolysis for function. The strand-passage reaction requires that the enzyme be covalently attached to the DNA through a tyrosine residue (Ralph, R. K. et al., *Topics in Molecular and Structural Biology: Molecular Aspects of Anti-cancer Drug-DNA Interactions*, 1994). Topo I is not capable of more complex catalytic reactions such as catenation or decatenation because these processes require double strand cleavage.

Topo II acts on both strands of DNA by cutting; passage of a double-stranded DNA through the cleaved strands, followed by ligation and requires energy through ATP hydrolysis. It exists as two isozymes of 170 kD (Topo IIα) and 180 kD (Topo IIβ) (Drake, F. H. et al., *J. Biol. Chem.*, 262(34), 16739-47, 1987; Drake, F. H. et al., *Biochemistry*, 28(20), 8154-60, 1989) and can relax supercoiled closed circular DNA plasmids in vitro (Osheroff, N. et al., *J. Biol. Chem.*, 258(15), 9536-43, 1983). Topo IIα is highly expressed in proliferating cells and is located at the base of chromatin loops (Wood, E. R. et al., *J Cell Biol.*, 111(6 Pt 2), 2839-50, 1990) implying a role in chromosome separation in mitosis whereas Topo IIβ is localized in the nucleolus implying a role in gene expression (Ura, K. et al., *Nucleic Acids Res.*, 19(22), 6087-92, 1991) and its precise biological role is not known. Generally, many Topo IIα poisons also possess Topo IIβ poison activity (Austin C. A., *Bioessays*, 20(3), 215-26, 1998; Cornarotti, M. et al., *Mol. Pharmacol.*, 50(6), 1463-71, 1996; Perri, D. et al., *Biochem. Pharmacol.*, 56(4), 503-7 1998). Further, the significance of inhibitors specific for Topo IIβ such as XK469 (Gao, H. et al., *Proc. Natl. Acad. Sci. USA*, 96(21), 12168-73, 1999) has yet to be proven clinically.

Topo inhibitors can be divided into two classes by their mechanism of action: Topo poisons and reversible catalytic inhibitors. Topo catalytic inhibitors such as merbarone (Khelifa, T. et al., *Mol Pharmacol.*, 55(3), 548-56, 1999) or ICRF-193 (Roca, J. et al., *Proc. Natl. Acad. Sci. USA*, 91(5), 1781-5, 1994) work by inhibiting the overall catalytic activity of the enzyme without introducing double strand DNA breaks, and work by inhibiting either the DNA binding, cleavage, or religation steps. Topo poisons are compounds that stabilize the covalent DNA-enzyme intermediates and therefore, turn it into a DNA damaging agent by introducing high levels of double-strand breaks which ultimately leads to triggering of apoptotic pathways (Kaufmann, S. H., *Biochim. Biophys. Acta.*, 1400(1-3), 195-211, 1998). Topo poisons are known for both Topo I and II enzymes, and further, dual inhibitors of both Topo I and II are known to exist in each of the two general classes of inhibitors (Holden, J. A., *Curr. Med. Chem. Anti-Canc. Agents*, 1(1), 1-25, 2001).

Clinically relevant Topo II inhibitors act by trapping the enzyme in a covalent intermediate and can be divided into two classes. One class is comprised of DNA intercalators or minor-groove binders that impede the Topo religation step primarily by altering local DNA structure through directly binding DNA, and the second class consists of molecules that bind to the enzyme itself to prevent the DNA religation step.

Camptothecin is one of the first Topo I poisons to become a drug by binding to the Topo I-DNA complex reversibly (Leroy, D. et al., *Biochemistry*, 40(6), 1624-34, 2001). Second generation drugs to follow camptothecin are raltitrexed (AstraZeneca), irinotecan (Pharmacia), and topotecan (GlaxoSmithKline). Irinotecan has shown survival benefits in colorectal cancer as early as 1996, and is now a first-line use for colorectal cancer therapy and also has a major use in chronic lymphocytic leukemia. Topotecan has gained approval as a second-line treatment for ovarian and small cell lung cancer. These second generation drugs improve two problems with camptothecin, namely, the instability of the lactone ring in serum and low water solubility.

Anthracyclines, aminoanthracenes, podophyllotoxins, aminoacridines, ellipticines, and quinolones classes of molecules are known to act on Topo II. The most important drugs that target Topo II include the podophyllotoxins such as etoposide and the anthracyclines whose primary agent is doxorubicin, but amsacrine and mitoxantrone are marketed as well. Etoposide is front-line therapy for several malignancies including leukemias and lymphomas while the more widely used doxorubicin is front-line therapy in leukemias, lymphomas, and solid tumors including breast cancers. Second generation anthracyclines include daunorubicin (Gilead), and idarubicin (Pharmacia). The anthracyclines, in general, suffer from the major side effect of cardiotoxicity when administered chronically beyond certain accumulated doses. The second-generation compounds that follow doxorubicin are aimed at minimizing the cardiotoxic effects while maintaining anti-tumor effects. Second generation podophyllotoxins would include teniposide that is marketed as a drug.

Dual Topo I/II inhibitors which are furthest along in development would include: aclarubicin (NCI) which has completed phase II clinical studies, DACA (NCI) has phase I completed but halted, intoplicine (NCI) has completed phase I, TAS 103 (NCI/Taiho) is in phase I, BN80927 (Beaufour Ipsen) is in preclinical development, F11782 (Fabre) is also in preclinical, and XR11576 (Xenova/Millenium) which has completed phase I.

A significant problem that can arise in the clinic with most cancer treatments is the existence of multi-drug resistance (MDR). This can either be intrinsic when chemotherapy is started or acquired over time with treatment. The up-regulation of the MDR1 gene coding for P-glycoprotein (Pgp) is a major mechanism for acquired MDR (Endicott, J. A. et al., *Annu. Rev. Biochem.*, 58, 137-71, 1989). Pgp is an ATP-dependent, membrane-bound drug efflux pump that has been extensively studied. Pgp has been shown to have broad substrate specificity and is capable of effluxing numerous xenobiotics and drugs including anthracyclines, Vinca alkaloids, epipodophyllotoxins, and taxanes from the cytoplasm of cells. Due to the key role of Pgp in MDR, antagonists of this pump are being discovered and tested for their use as an adjunct to anticancer drugs (Kaye, S. B. et al., *J. Clin. Oncol.*, 16(2), 692-701, 1998; Sikic, B. I., *Oncology (Hunting)*, 13(5A), 183-7, 1999) to increase penetration of antitumor drugs for MDR reversal. The net result of acquired MDR during chemotherapeutic treatment is after an initial remission in tumor growth, a diminished sensitivity to a broad range of drugs is seen presumably due to decreased intracellular concentrations, and tumors become refractory to treatment. Small-cell lung cancer is a good example of a malignancy that typically acquires MDR, and makes treatment very difficult.

Pgp is also thought to play a significant role in the establishment of the blood-brain barrier and is highly present in other tissues including liver, intestine, lung, kidney, and even bone marrow. Work performed on mice lacking their endogenous Pgp's (mdr1a/1b) provide compelling evidence that high levels of Pgp in a tissue can decrease the overall accumulation of drugs which are recognized by this efflux pump (Schinkel, A. H. et al., *Proc. Natl. Acad. Sci. USA*, 94(8), 4028-33, 1997).

Other drug resistance mechanisms specifically relating to Topo-directed drugs are: reduced Topo expression levels, Topo enzyme mutations, lengthened cell cycle time, diminished cellular accumulation, and altered DNA repair function (Chen, A. Y. et al., *Annu Rev Pharmacol Toxicol.*, 34, 191-218, 1994). Also, inhibition of Topo I can induce increases in Topo II amounts, which can lead to resistance (Bonner, J. A. et al., *Cancer Chemother Pharmacol.*, 39(1-2), 109-12, 1996). Therefore, there is still a need in the art for compounds that inhibit Topo I or Topo II or are dual inhibitors of both Topo I and II and is active against multi-drug resistant cancers. The present invention provides such new compounds, compositions and methods of treatment.

BRIEF SUMMARY OF THE INVENTION

The present invention provides compounds that are inhibitors of topoisomerase. In many instances, the compounds of the present invention are inhibitors of both topoisomerase I and II. As such, the present invention provides compounds having the general structure I:

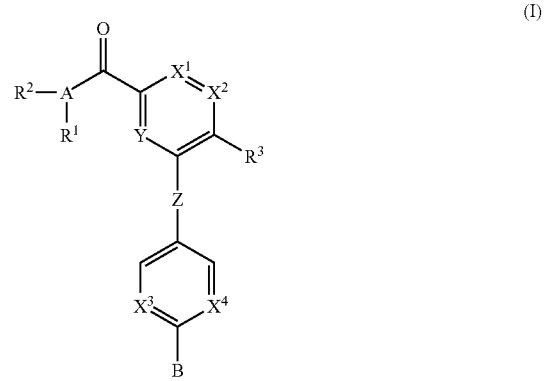

in which A is nitrogen or carbon. $R^1$ is a member selected from the group consisting of hydrogen, $(C_1-C_8)$alkyl, $(C_1-C_8)$heteroalkyl, $(C_3-C_8)$heterocycloalkyl$(C_1-C_8)$alkyl and aryl $(C_1-C_8)$alkyl. $R^2$ is a member selected from the group consisting of aryl, heteroaryl, aryl$(C_1-C_8)$alkyl, heteroaryl$(C_1-C_8)$alkyl, $(C_3-C_8)$cycloalkyl, $(C_3-C_8)$cycloalkyl$(C_1-C_6)$alkyl, $(C_3-C_8)$heterocycloalkyl, $(C_3-C_8)$heterocycloalkyl$(C_1-C_6)$alkyl, $(C_1-C_8)$heteroalkyl, and —X—$R^4$, wherein X is —NH— or —O— and $R^4$ is hydrogen, aryl —C(O)$R^5$ or heteroaryl, wherein $R^5$ is hydrogen, aryl$(C_1-C_4)$alkyleneoxy, $(C_1-C_4)$alkyl, or $(C_1-C_4)$alkoxy. Alternatively, $R^1$ and $R^2$ and the atom to which they are attached form a 5- to 7-membered ring having 0-3 heteroatoms. The 5- to 7-membered ring is optionally substituted with 1-4 substituents selected from the group consisting of alkyl, heteroalkyl, aryl, heteroaryl, amino, amino$(C_1-C_4)$alkyl, dialkylamino$(C_1-C_4)$alkyl, —C=NH(NH$_2$), —CN, hydroxy, —NHC(O)$R^6$, $X^9$NHC(O)$R^6$ and —C(O)$R^6$; wherein $R^6$ is $(C_1-C_6)$alkoxy, aryl$(C_1-C_6)$alkyleneoxy, heteroaryl$(C_1-C_6)$alkyleneoxy, amino, $(C_1-C_6)$alkylamino, aryl$(C_1-C_6)$alkylamino, heteroaryl$(C_1-C_6)$alkylamino, hydroxy, or $(C_1-C_4)$alkyl. $X^9$ is absent or $CH_2$. If present, any of said substituents located on adjacent atoms in said 5- to 7-membered ring may optionally be replaced with a substituent of formula -E-(CH$_2$)$_u$—F— to form a fused ring wherein u is an integer from 1-2, E and F are each independently $CH_2$, O or NH and wherein up to three bonds in said fused ring formed may optionally be replaced with a double bond; and wherein the fused ring is further substituted with 0-4 substitutents selected from the group consisting of halogen, aryl, heteroaryl, $(C_1-C_4)$alkyl, $(C_1-C_4)$heteroalkyl, hydroxy, amino, —CN and —NO$_2$. $X^1$ and $X^2$ are independently N or C—$R^7$, wherein $R^7$ is selected from the group consisting of hydrogen, halogen, alkyl, haloalkyl, heteroalkyl, aryl, —NO$_2$, —CN, —S(O)$_2R^8$, —S(O)$R^8$, wherein $R^8$ is a member selected from the group consisting of hydrogen, $(C_1-C_4)$alkyl, amino and alkylamino. Y is C—H or N. Z is a bond, —CH=CH—, or —C≡C—. $R^3$ is a member selected from the group consisting of hydrogen, halogen, alkyl, alkoxy, hydroxy, halo$(C_1-C_6)$alkyl, heteroalkyl, —NO$_2$, —CN, —CH$_2$CN, —SR$^9$, —O—S(O)R$^9$, —S(O)$_2R^9$, and —S(O)R$^9$, wherein $R^9$ is a member selected from the group consisting of hydrogen, $(C_1-C_4)$alkyl, amino and alkylamino. $X^3$ and $X^4$ are independently N or —C—$R^{10}$, wherein $R^{10}$ is a member selected from the group consisting of hydrogen, aryl, heteroaryl, hydroxy, hydroxymethyl, alkoxy, $(C_1-C_4)$dialkylamino$(C_1-C_4)$alkyl, halogen, aryl, heteroaryl, —S(O)$_2$Me, amino, $(C_1-C_4)$dialkylamino, $(C_1-C_6)$alkyl, —(CH$_2$)$_{d1}$(CO)OR$^{11}$, —(CH$_2$)$_{d2}$(CO)NR$^{11}R^{12}$, —(X$^{10}$)$_{d3}$(CH$_2$)$_{d4}$NR$^{11}$(CO)R$^{12}$, and —(X$^{10}$)$_{d5}$(CH$_2$)$_{d6}$O (CO)R$^{11}$; wherein at each occurrence, R$^{11}$ and R$^{12}$ is independently a member selected from the group consisting of hydrogen, (C$_1$-C$_6$)alkyl, (C$_1$-C$_6$)heteroalkyl, aryl, heteroaryl, aryl(C$_1$-C$_6$)alkyl, heteroaryl(C$_1$-C$_6$)alkyl, (C$_1$-C$_4$)dialkylamino, (C$_1$-C$_4$)alkylamino, hydroxymethyl, alkoxy, —(CH$_2$)$_{e1}$SO$_3$R$^{13}$, and —(CH$_2$)$_{e2}$CO$_2$R$^{13}$, wherein R$^{13}$ is hydrogen or (C$_1$-C$_6$)alkyl and e1 and e2 are each an integer from 0 to 4; X$^{10}$ is (C$_1$-C$_6$)alkylene, —O—, —S—, —S(O)—, —S(O)$_2$— or —NR$^{14}$—, wherein R$^{14}$ is hydrogen or (C$_1$-C$_6$)alkyl; and d1 to d6 are each an integer from 0 to 4. B is a member selected from the group consisting of hydrogen, aryl, heteroaryl, alkyl, heteroalkyl, alkoxy, benzyloxy, phenoxy, hydroxymethyl, halo(C$_1$-C$_4$)alkyl, halogen, —NO$_2$, —CN, —OC(O)NR$^{15}$R$^{16}$, —NR$^{17}$C(O)R$^{17}$, —C(O)R$^{17}$, —C(O)$_2$R$^{17}$, —(CH$_2$)$_{f1}$S(O)$_2$R$^{17}$, and —(CH$_2$)$_{f2}$S(O)R$^7$, wherein the subscripts f1 and f2 are each an integer from 0-3 and R$^{17}$ is a member selected from the group consisting of hydrogen, (C$_1$-C$_4$)alkyl, aryl, heteroaryl, hydroxy, amino, dialkylamino, alkylamino and arylalkylamino, wherein R$^{15}$ and R$^{16}$ are independently hydrogen, (C$_1$-C$_4$)alkyl, (C$_1$-C$_4$) heteroalkyl or aryl. Alternatively, R$^{15}$ and R$^{16}$ combine to form a 3-7 membered ring optionally having 1-3 additional heteroatoms and optionally having additional substituents selected from the group consisting of phenyl and (C$_1$-C$_4$) alkyl, and pharmaceutically acceptable prodrugs and solvates thereof.

In another aspect, this invention provides for pharmaceutical compositions of compounds having formula I or a prodrug or pharmaceutically acceptable salt thereof with a pharmaceutically acceptable carrier.

The compounds of formula I can be used in the treatment of cell-proliferative disorders. More particularly, the compounds of formula I can be used in the treatment of cancer and multi-drug resistant cancers. As such, the present invention also provides a method of treating cell-proliferative disorders (e.g., cancer) comprising administering to a subject suffering from a cell-proliferative disorder with an effective amount of a compound of formula I. These and other aspects, advantages and embodiments will become more apparent with the detailed description which follow.

DETAILED DESCRIPTION OF THE INVENTION

I. Definitions

Figure 1:
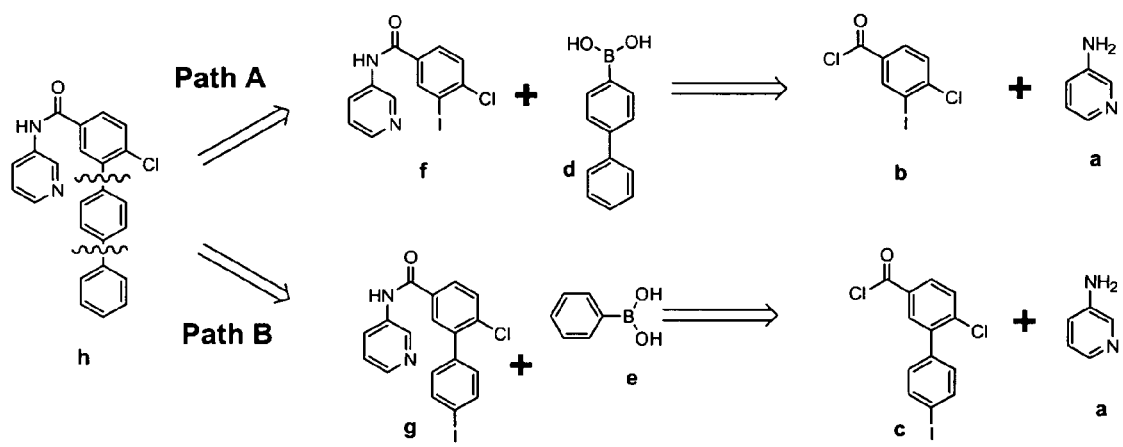
FIG. 1 provides a general retrosynthetic scheme for preparing compounds of the present invention.

The term "alkyl," by itself or as part of another substituent, means, unless otherwise stated, a straight or branched chain hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —CH$_2$CH$_2$CH$_2$CH$_2$—. Typically, an alkyl (or alkylene) group will have from 1 to 24 carbon atoms, with those groups having 10 or fewer carbon atoms being preferred in the present invention.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified by —CH$_2$—CH$_2$—S—CH$_2$CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the terms "aryl" or "heteroaryl" when used in combination with other terms (e.g., aryloxy, arylthioxy, arylalkyl) is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R'" each independently refer to hydrogen, unsubstituted ($C_1$-$C_8$)alkyl and heteroalkyl, unsubstituted aryl, aryl substituted with 1-3 halogens, heteroaryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form an optionally substituted 3-, 4-, 5-, 6-, or 7-membered ring optionally having 1-3 additional heteroatoms. For example, —NR'R" is meant to include 1-pyrrolidinyl, 4-piperazinyl and 4-morpholinyl. Optionally the newly formed 4- to 7-membered ring may additionally be substituted with a variety of group selected from: alkyl, heteroalkyl, aryl, heteroaryl, hydroxyl, halogen and alkoxy. Alternatively, two adjacent substituents on the newly formed 4- to 7-membered ring may be replaced with a substituent of formula -E-(CH$_2$)$_u$—F—, where u is 1-2, E and F are independently CH$_2$, and where up to 3 bonds in the new ring formed may optionally be replaced with a double bond and where the new ring formed may further be substituted with 0-4 substituents selected from the group consisting of halogen, halo($C_1$-$C_4$)alkyl, alkyl, —CN and —NO$_2$. Furthermore, any two substituents located on adjacent atoms or attached to the same atom in an alkyl or heteroalkyl substituent (including those groups often referred to as alkylene, alkenyl, heteroalkylene, heteroalkenyl, alkynyl, cycloalkyl, heterocycloalkyl, cycloalkenyl, and heterocycloalkenyl) can cyclize to form a 3- to 7-member ring optionally substituted with additional substituents selected from the group consisting of ($C_1$-$C_6$) alkyl, hetero($C_1$-$C_6$)alkyl, aryl, heteroaryl and hydroxyl; wherein if present, any of said substituents located on adjacent atoms in said 4- to 7-membered ring may optionally be replaced with a substituent of formula -E-(CH$_2$)$_u$—F— to form a fused ring wherein u is an integer from 1-2, E and F are each independently CH$_2$, O or NH; wherein up to three bonds in said fused ring formed may optionally be replaced with a double bond; and wherein said fused ring formed may further be substituted with 0-4 substitutents selected from the group consisting of halogen, alkyl, heteroalkyl, aryl, heteroaryl, —CN and —NO$_2$. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O) CH$_2$OCH$_3$, and the like).

Similarly, substituents for the aryl and heteroaryl groups are varied and are selected from: -halogen, —OR', —OC(O) R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$) =NH, —NR'C(NH$_2$)=NH, —NH—C(NH$_2$)=NR', —S(O) R', —S(O)$_2$R', —S(O)$_2$NR'R", —N$_3$, —CH(Ph)$_2$, perfluoro ($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

Two of the substituents on adjacent atoms of the aryl or heteroaryl ring may optionally be replaced with a substituent of the formula -T-C(O)—(CH$_2$)$_q$-U-, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

As used herein, the term "heteroatom" is meant to include oxygen (O), nitrogen (N), sulfur (S) and silicon (Si).

The term "cell proliferative disorder" includes disorders involving the undesired proliferation of a cell. Non-limiting examples of such disorders include cancerous tumors, (e.g., brain, lung (small cell and non-small cell), ovary, prostate, breast or colon) or other carcinomas or sarcomas (e.g., leukemia, lymphoma).

As used herein, the term "treating" a disease condition, includes either treating the disease in its active or remissive state as well as preventing or delaying the onset or contraction of the disease condition.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. A prodrug is a compound that, after administration, is metabolized or otherwise converted to an active or more active form with respect to at least one property. To produce a prodrug, a pharmaceutically active compound can be modified chemically to render it less active or inactive, but the chemical modification is such that an active form of the compound is generated by metabolic or other biological processes. A prodrug may have, relative to the drug, altered metabolic stability or transport characteristics, fewer side effects or lower toxicity, or improved flavor, for example (see the reference Nogrady, 1985, Medicinal Chemistry A Biochemical Approach, Oxford University Press, New York, pages 388-392). Prodrugs can also be prepared using compounds that are not drugs. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

II. Description of the Embodiments

A. Compounds

The present invention provides compounds having the formula (I):

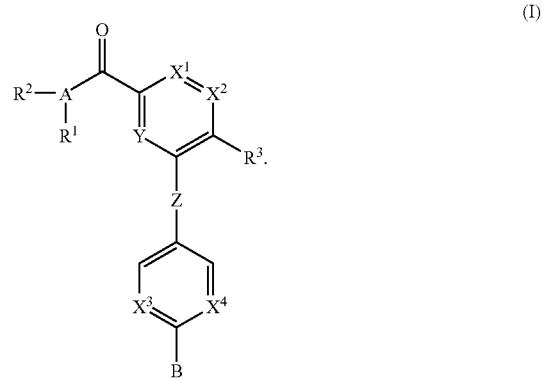

(I)

The compounds of formula I are useful for the treatment of cell proliferative disorders. In formula I, A is selected from the group consisting of carbon and nitrogen, preferably A is nitrogen. R$^1$ is a member selected from the group consisting of hydrogen, $(C_1-C_8)$alkyl, $(C_1-C_8)$heteroalkyl, $(C_3-C_8)$heterocycloalkyl$(C_1-C_8)$alkyl and aryl$(C_1-C_8)$alkyl. $R^2$ is a member selected from the group consisting of aryl, heteroaryl, aryl$(C_1-C_8)$alkyl, heteroaryl$(C_1-C_8)$alkyl, $(C_3-C_8)$cycloalkyl, $(C_3-C_8)$cycloalkyl$(C_1-C_6)$alkyl, $(C_3-C_8)$heterocycloalkyl, $(C_3-C_8)$heterocycloalkyl$(C_1-C_6)$alkyl, $(C_1-C_8)$heteroalkyl, and $-X-R^4$, wherein X is $-NH-$ or $-O-$ and $R^4$ is hydrogen, aryl, $-C(O)R^5$, or heteroaryl. $R^5$ is selected from the group consisting of hydrogen, aryl$(C_1-C_4)$alkyleneoxy, $(C_1-C_4)$alkyl and $(C_1-C_4)$alkoxy. Alternatively $R^1$ and $R^2$ and the atom to which they are attached join to form a 5- to 7-membered ring having 0-3 heteroatoms, wherein said 5- to 7-membered ring is optionally substituted with 1-4 substituents selected from the group consisting of alkyl, heteroalkyl, aryl, heteroaryl, amino, amino$(C_1-C_4)$alkyl, dialkylamino$(C_1-C_4)$alkyl, $-C=NH(NH_2)$, $-CN$, hydroxy, $-NHC(O)R^6$, $X^9NHC(O)R^6$ and $-C(O)R^6$; wherein $R^6$ is $(C_1-C_6)$alkoxy, aryl$(C_1-C_6)$alkeneoxy, heteroaryl$(C_1-C_6)$alkeneoxy, amino, $(C_1-C_6)$alkylamino, aryl$(C_1-C_6)$alkylamino, heteroaryl$(C_1-C_6)$alkylamino, hydroxy, or $(C_1-C_4)$alkyl. $X^9$, if present, is $CH_2$. Any of said substituents located on adjacent atoms in said 5- to 7-membered ring may optionally be replaced with a substituent of formula $-E-(CH_2)_u-F-$ to form a fused ring wherein, u is an integer from 1-2, E and F are each independently $CH_2$, O or NH. Up to three bonds in the fused ring formed may optionally be replaced with a double bond and wherein the fused ring formed is further substituted with 0-4 substitutents selected from the group consisting of halogen, aryl, heteroaryl, $(C_1-C_4)$alkyl, $(C_1-C_4)$heteroalkyl, hydroxy, amino, $-CN$ and $-NO_2$. In one embodiment, $R^1$ is hydrogen, $(C_1-C_8)$alkyl, $(C_3-C_8)$heterocycloalkyl or $(C_1-C_8)$heteroalkyl; and $R^2$ is an aryl group or a heteroaryl group containing 1-3 heteroatoms selected from the group consisting of nitrogen, oxygen or sulfur.

In a preferred embodiment, $R^1$ is hydrogen, $(C_1-C_8)$heteroalkyl or $(C_3-C_8)$heterocycloalkyl; and $R^2$ is aryl or heteroaryl, wherein in one embodiment, the aryl or heteroaryl group is selected from the group consisting of phenyl, naphthyl, pyridyl, pyrimidyl, indolyl, quinolyl, isoquinolyl, quinoxalinyl, oxazolyl, oxadiazolyl, benimidazolyl, pyrazinyl, pyradizinyl, triazinyl, benzothiazolyl, benzothiadiazolyl, thiazolyl and thiadiazolyl, wherein said aryl and heteroaryl group is optionally substituted the 1-3 substituents selected from the group consisting of aryl, heteroaryl, amino, phenyl, oxazolyl, $(C_1-C_4)$dialkylamino$(C_1-C_4)$alkyl, $-X^5NHC(O)X^6R^8$, $(C_1-C_8)$heterocycloalkyl$(C_1-C_6)$alkyl, $(C_1-C_8)$heterocycloalkyl, $(C_1-C_4)$alkoxy, hydroxymethyl, phenyl, $(C_1-C_4)$alkyl, halo$(C_1-C_4)$alkyl, fluoro, chloro, bromo, morpholinyl, piperazinyl, succinylimido, $-SR^{19}$, $-S(O)R^{19}$, $-S(O)_2R^{19}$, and $-C(O)R^{20}$, wherein $X^5$ and $X^6$ are each independently absent or is $(C_1-C_3)$alkyl; wherein $R^{18}$ is $(C_3-C_8)$heterocycloalkyl or $(C_1-C_6)$alkoxy; $R^{19}$ is selected from the group consisting of $(C_1-C_4)$alkyl, $(C_2-C_4)$alkenyl, amino, $(C_1-C_4)$dialkylamino and $(C_1-C_4)$dialkylamino$(C_1-C_4)$alkyl; and $R^{20}$ is a member selected from the group consisting of $(C_1-C_4)$alkyl, $(C_1-C_4)$alkoxy and hydroxy. In another embodiment, $R^2$ is a member selected from the group consisting of:

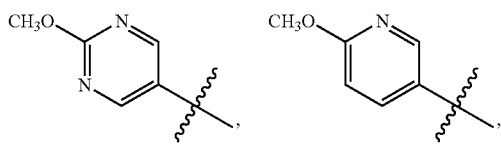

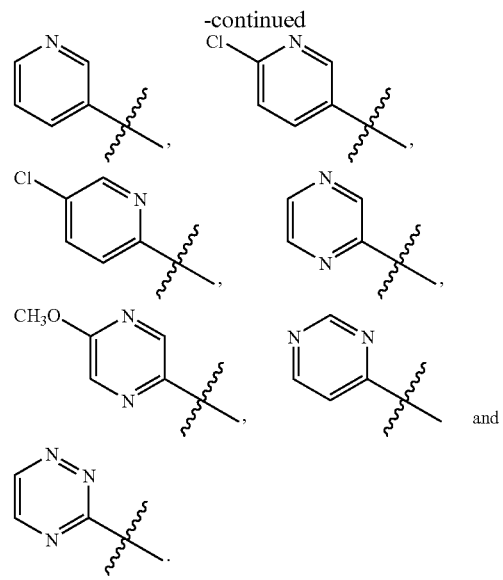

In another embodiment, $R^2$ has the formula

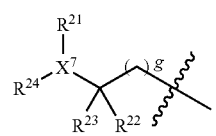

(II)

in which $X^7$ is N, O, S or C; but when $X^7$ is S or O, either $R^{21}$ or $R^{24}$ is absent. g is an integer from 1 to 6. $R^{21}$, $R^{22}$, $R^{23}$ and $R^{24}$ at each occurrence are independently a member selected from the group consisting of hydrogen, halogen, halo$(C_1-C_6)$alkyl, $(C_1-C_6)$alkyl, $(C_3-C_6)$cycloalkyl, aryl, heteroaryl, aryl$(C_1-C_6)$alkyl and $-C(O)_2R^{25}$; wherein $R^{25}$ is hydrogen. In one embodiment, g is 1. Alternatively, $R^{21}$ and $R^{24}$ taken together with $X^7$ form a 4- to 7-membered ring optionally containing 0-3 heteroatoms and optionally substituted with members selected from the group consisting of $(C_1-C_6)$alkyl, $(C_1-C_6)$acyl, aryl, heteroaryl, hydroxyl, alkoxy, amino and alkylamino. Alternatively, $R^{23}$ and $R^{24}$ taken together with the atoms to which they are attached to form a 4- to 7-membered ring containing 0-3 additional heteroatoms, wherein said 4- to 7-membered ring is optionally substituted with 1-3 substituents selected from the group consisting of $(C_1-C_6)$alkyl, $(C_1-C_6)$heteroalkyl, hydroxy or $C(O)_2R^{26}$, wherein $R^{26}$ is hydrogen or $(C_1-C_4)$alkyl.

In one embodiment, $R^2$ is selected from the group consisting of:

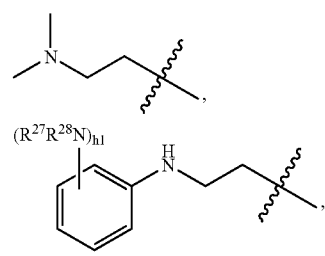

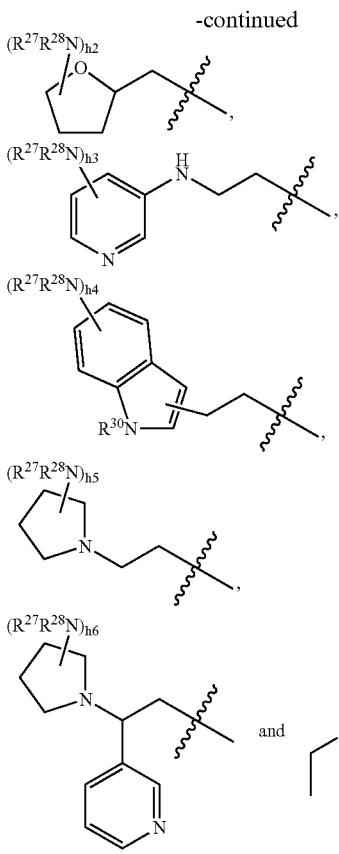

in which $R^{27}$ and $R^{28}$ is independently a member selected from the group consisting of hydrogen, $(C_1-C_6)$alkyl, $(C_1-C_6)$heteroalkyl, aryl, heteroaryl, halogen, hydroxyl, —$NO_2$, —CN, $C(O)R^{29}$ and amino, wherein $R^{29}$ is $(C_1-C_4)$alkyl, $(C_1-C_4)$alkoxy and aryl. $R^{30}$ is selected from the group consisting of hydrogen, $(C_1-C_4)$alkyl, hetero$(C_1-C_4)$alkyl and heteroaryl and h1 to h6 are each an integer from 0-4.

In yet another embodiment, the $R^2$ substituent has the formula

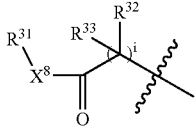

(III)

in which $X^8$ is —O—, —NH—, or —$NR^{34}$—; and wherein $R^{34}$ is hydrogen or $(C_1-C_4)$alkyl. $R^{31}$ is a member selected from the group consisting of hydrogen, $(C_1-C_8)$alkyl, aryl $(C_1-C_6)$alkyl, heteroaryl$(C_1-C_6)$alkyl, —$CHR^{35}(CO_2H)$, wherein $R^{35}$ is $(C_1-C_6)$alkyl, $(C_1-C_6)$heteroalkyl, heteroaryl $(C_1-C_6)$alkyl or aryl$(C_1-C_6)$alkyl. $R^{32}$ and $R^{33}$ at each occurrence are independently a member selected from the group consisting of hydrogen, halogen, halo$(C_1-C_6)$alkyl, $(C_1-C_6)$alkyl, hetero$(C_1-C_6)$alkyl, $(C_1-C_8)$cycloalkyl$(C_1-C_6)$alkyl, aryl$(C_1-C_6)$alkyl and heteroaryl$(C_1-C_6)$alkyl. i is an integer from 1 to 6. In one embodiment, i is 1. Alternatively, $R^{32}$ and $R^{33}$, or $R^{31}$ and $R^{34}$, and the atom(s) to which they are attached, optionally form a 3- to 7-membered ring optionally substituted with 1 to 4 substituents selected from the group consisting of $(C_1-C_6)$alkyl, hetero$(C_1-C_6)$alkyl, aryl, heteroaryl and hydroxyl. Any of said substituents located on adjacent atoms in said 3- to 7-membered ring may optionally be replaced with a substituent of formula -E-$(CH_2)_u$—F— to form a fused ring wherein, u is an integer from 1-2, E and F are each independently $CH_2$, O or NH wherein up to three bonds in the fused ring formed may optionally be replaced with a double bond. The fused ring formed is further be substituted with 0-4 substitutents selected from the group consisting of halogen, alkyl, heteroalkyl, aryl, heteroaryl, —CN and —$NO_2$.

Preferably, $R^2$ is selected from the group consisting of:

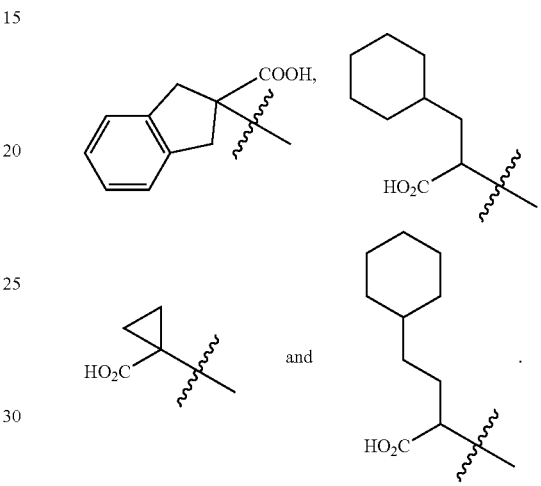

In formula I, $X^1$ and $X^2$ are independently N or C—$R^7$, wherein $R^7$ is a member selected from the group consisting of hydrogen, halogen, alkyl, haloalkyl, heteroalkyl, aryl, —$NO_2$, —CN, —$S(O)_2R^8$, —$S(O)R^8$, wherein $R^8$ is a member selected from the group consisting of hydrogen, $(C_1-C_4)$ alkyl, amino and alkylamino. Y is C—H or N. Z is a bond, —CH═CH—, or —C≡C—. In one embodiment, Z is a bond. $R^3$ is a member selected from the group consisting of hydrogen, halogen, alkyl, alkoxy, hydroxy, halo$(C_1-C_6)$alkyl, heteroalkyl, —$NO_2$, —CN, —$CH_2CN$, —$SR^9$, —$S(O)R^9$, —$S(O)_2R^9$, and —$S(O)R^9$, wherein $R^9$ is selected from the group consisting of hydrogen, $(C_1-C_4)$alkyl, amino and alkylamino.

$X^3$ and $X^4$ are independently N or —C—$R^{10}$, wherein $R^{10}$ is a member selected from the group consisting of hydrogen, aryl, heteroaryl, hydroxy, hydroxymethyl, alkoxy, $(C_1-C_4)$ dialkylamino$(C_1-C_4)$alkyl, halogen, aryl, heteroaryl, —S $(O)_2Me$, amino, $(C_1-C_4)$dialkylamino, $(C_1-C_6)$alkyl, —$(CH_2)_{d1}(CO)OR^{11}$, —$(CH_2)_{d2}(CO)NR^{11}R^{12}$, $(X^{10})_{d3}(CH_2)_{d4}NR^{11}(CO)R^{12}$, and $(X^{10})_{d5}(CH_2)_{d6}O(CO)R^{11}$; wherein at each occurrence, $R^{11}$ and $R^{12}$ is independently a member selected from the group consisting of hydrogen, $(C_1-C_6)$alkyl, $(C_1-C_6)$heteroalkyl, aryl, heteroaryl, aryl$(C_1-C_6)$alkyl, heteroaryl$(C_1-C_6)$alkyl, $(C_1-C_4)$dialkylamino, $(C_1-C_4)$alkylamino, hydroxymethyl, alkoxy, —$(CH_2)_{e1}SO_3R^{13}$, and $(CH_2)_{e2}CO_2R^{13}$, wherein $R^{13}$ is hydrogen or $(C_1-C_6)$ alkyl and y is an integer from 0 to 4; $X^{10}$ is $(C_1-C_4)$alkyl, —O—, —S—, —$S(O)$—, —$S(O)_2$— or —$NR^{14}$—, wherein $R^{14}$ is hydrogen or $(C_1-C_6)$alkyl; and n is an integer from 0 to 4. In one embodiment, $X^3$ or $X^4$ are each independently selected from the group consisting of N and C—$R^{10}$, wherein $R^{10}$ is selected from the group consisting of hydrogen, aryl, —$(CH_2)_{d1}(CO)OR^{11}$, —$(CH_2)_{d2}(CO)NR^{11}R^{12}$, —$(X^{10})_{d3}$ $(CH_2)_{d4}NR^{11}(CO)R^{12}$, and $-(X^{10})_{d5}(CH_2)_{d6}O(CO)R^{11}$; wherein at each occurrence, $R^{11}$ and $R^{12}$ is independently $(C_1-C_6)$alkyl, $(C_1-C_6)$heteroalkyl, aryl, heteroaryl, aryl$(C_1-C_6)$alkyl, heteroaryl$(C_1-C_6)$alkyl, $(C_1-C_4)$dialkylamino, $(C_1-C_4)$alkylamino, hydroxymethyl, alkoxy, $-(CH_2)_{e1}SO_3R^{13}$, or $-(CH_2)_{e2}CO_2R^{13}$, wherein $R^{13}$ is hydrogen or $(C_1-C_6)$alkyl and e1 and e2 are each an integer from 0 to 4; $X^{10}$ is $(C_1-C_6)$alkylene, $-O-$, or $-NR^{14}-$, wherein $R^{14}$ is hydrogen or $(C_1-C_6)$alkyl; and d1 to d6 are each an integer from 0 to 4.

B is a member selected from the group consisting of hydrogen, aryl, heteroaryl, alkyl, heteroalkyl, alkoxy, benzyloxy, phenoxy, hydroxymethyl, halo$(C_1-C_4)$alkyl, halogen, $-NO_2$, $-CN$, $-OC(O)NR^{15}R^{16}$, $-NR^{17}C(O)R^{17}$, $-C(O)R^{17}$, $-C(O)_2R^{17}$, $-(CH_2)_{f1}S(O)_2R^{17}$, and $-(CH_2)_{f2}S(O)R^{17}$, wherein the subscripts f1 and f2 are each an integer from 0-3 and $R^{17}$ is selected from the group consisting of hydrogen, $(C_1-C_4)$alkyl, aryl, heteroaryl, hydroxy, amino, dialkylamino, alkylamino and arylalkylamino; wherein $R^{15}$ and $R^{16}$ are independently hydrogen, $(C_1-C_4)$alkyl, $(C_1-C_4)$heteroalkyl or aryl; alternatively $R^{15}$ and $R^{16}$ combine to form a 3- to 7-membered ring having 1-3 heteroatoms; wherein said 3- to 7-membered ring can optionally have 1-3 substituents selected from the group consisting of phenyl and $(C_1-C_4)$alkyl.

In one embodiment, Z is a bond and B is aryl or heteroaryl. In another embodiment, B is selected from the group consisting of phenyl, pyridyl, indolyl, pyrimidinyl and $-(CH_2)_{f1}S(O)_2R^{17}$, wherein f1 is an integer between 0-1 and $R^{17}$ is selected from the group consisting of $(C_1-C_4)$alkyl, amino, dialkylamino and alkylamino. When B is aryl or heteroaryl and Z is a bond, the compounds of the invention can also be referred to as "terphenyl-amide compounds".

In yet another embodiment, Z is a bond and B is $-(CH_2)_{f1}S(O)_2R^{17}$, or $-(CH_2)_{f2}S(O)R^{17}$, wherein the subscripts f1 and f2 are each is an integer from 0-3 and $R^{17}$ is selected from the group consisting of hydrogen, $(C_1-C_4)$alkyl, aryl, heteroaryl, hydroxy, amino, dialkylamino, alkylamino and arylalkylamino.

Preferably B is a member selected from the group consisting of:

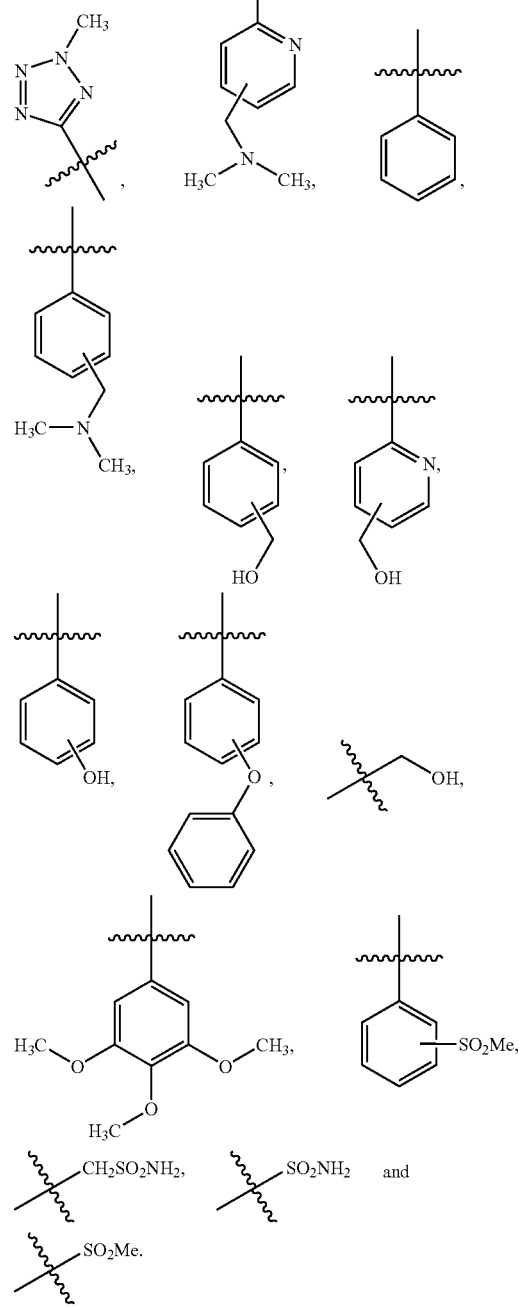

A family of specific compounds of particular interest within Formula I consists of compounds and pharmaceutically acceptable salts thereof as set forth in Table I.

TABLE I 1. 6-Chloro-4'-pyridin-2-yl-biphenyl-3-carboxylic acid (6-methoxy-pyridin-3-yl)-amide
2. 6-Chloro-[1,1';4',1"]terphenyl-3-carboxylic acid (2-methoxy-pyrimidin-5-yl)-amide
3. 6-Chloro-4'-dimethylsulfamoyl-biphenyl-3-carboxylic acid (6-methoxy-pyridin-3-yl)-amide
4. 6-Chloro-4'-pyridin-2-yl-biphenyl-3-carboxylic acid (6-methoxy-pyridin-3-yl)-amide TABLE I-continued 5. 6"-Chloro-[1,1';4',1"]terphenyl-3"-carboxylic acid pyrazin-2-ylamide
6. 6"-Chloro-2'-fluoro-[1,1';4',1"]terphenyl-3"-carboxylic acid (6-methoxy-pyridin-3-yl)-amide
7. 6-Chloro-3"-carboxamido-[1,1';4',1"]terphenyl-3-carboxylic acid (6-methoxy-pyridin-3-yl)-amide
8. 6-Chloro-[1,1';4',1"]terphenyl-3-carboxylic acid (6-methoxy-pyridin-3-yl)-amide
9. 6-Chloro-4'-pyridin-3-yl-biphenyl-3-carboxylic acid (6-methoxy-pyridin-3-yl)-amide
10. 6-Chloro-4'-pyridin-2-yl-biphenyl-3-carboxylic acid (6-methoxy-pyridin-3-yl)-amide
11. 6-Chloro-3"-hydroxy-[1,1';4',1"]terphenyl-3-carboxylic acid (6-methoxy-pyridin-3-yl)-amide
12. 6-Chloro-3'-hydroxy-biphenyl-3-carboxylic acid (6-methoxy-pyridin-3-yl)-amide
13. 6-Chloro-[1,1';4',1"]terphenyl-3-carboxylic acid (6-chloro-pyridin-3-yl)-amide
14. 6-Chloro-[1,1';4',1"]terphenyl-3-carboxylic acid (6-fluoro-pyridin-3-yl)-amide
15. 6-Chloro-[1,1';4',1"]terphenyl-3-carboxylic acid (6-methyl-pyridin-3-yl)-amide
16. 6-Chloro-3"-hydroxymethyl-[1,1';4',1"]terphenyl-3-carboxylic acid (6-methoxy-pyridin-3-yl)-amide
17. 6-Chloro-4'-pyridin-4-yl-biphenyl-3-carboxylic acid (6-methoxy-pyridin-3-yl)-amide
18. 4'-Acetyl-6-chloro-biphenyl-3-carboxylic acid (6-methoxy-pyridin-3-yl)-amide
19. 6-Chloro-4"-hydroxy-[1,1';4',1"]terphenyl-3-carboxylic acid (6-methoxy-pyridin-3-yl)-amide
20. 6-Chloro-[1,1';4',1"]terphenyl-3-carboxylic acid p-tolylamide
21. 5-Biphenyl-4-yl-6-chloro-N-(6-methoxy-pyridin-3-yl)-nicotinamide
22. 6-Chloro-4"-hydroxymethyl-[1,1';4',1"]terphenyl-3-carboxylic acid (6-methoxy-pyridin-3-yl)-amide
23. 6-Chloro-3"-methanesulfonyl-[1,1';4',1"]terphenyl-3-carboxylic acid (6-methoxy-pyridin-3-yl)-amide
24. 6"-Chloro-[1,1';4',1"]terphenyl-3"-carboxylic acid [1,2,4]triazin-3-ylamide
25. 6-Chloro-4'-methanesulfonyl-biphenyl-3-carboxylic acid (6-methoxy-pyridin-3-yl)-amide
26. 6-Chloro-[1,1';4',1"]terphenyl-3-carboxylic acid (2-pyrrolidin-1-yl-ethyl)-amide
27. 4-Methyl-piperazine-1-carboxylic acid 2'-chloro-5'-(6-methoxy-pyridin-3-ylcarbamoyl)-biphenyl-4-yl ester
28. 5-Fluoro-[1,1';4',1"]terphenyl-3-carboxylic acid (6-methoxy-pyridin-3-yl)-amide
29. 6-Methyl-[1,1';4',1"]terphenyl-3-carboxylic acid (6-methoxy-pyridin-3-yl)-amide
30. 4-Chloro-N-(6-methoxy-pyridin-3-yl)-3-(6-phenyl-pyridin-3-yl)-benzamide
31. 6"-Chloro-2'-fluoro-[1,1';4',1"]terphenyl-3"-carboxylic acid pyridin-3-ylamide
32. 6-Chloro-[1,1';4',1"]terphenyl-3-carboxylic acid (2-pyridin-3-yl-2-pyrrolidin-1-yl-ethyl)-amide
33. 6"-Chloro-[1,1';4',1"]terphenyl-3"-carboxylic acid (4,5-dihydro-thiazol-2-yl)-amide
34. 6"-Chloro-4-dimethylaminomethyl-[1,1';4',1"]terphenyl-3"-carboxylic acid (6-methoxy-pyridin-3-yl)-amide
35. 6-Chloro-[1,1';4',1"]terphenyl-3-carboxylic acid (2-diethylamino-ethyl)-amide
36. 6"-Chloro-[1,1';4',1"]terphenyl-3"-carboxylic acid (6-piperazin-1-yl-pyridin-3-yl)-amide
37. 6-Chloro-[1,1';4',1"]terphenyl-3-carboxylic acid pyrimidin-4-ylamide
38. 6-Chloro-[1,1';4',1"]terphenyl-3-carboxylic acid 3-aminomethyl-benzylamide
39. 4-Methyl-piperazine-1-carboxylic acid 2-chloro-5-(6-methoxy-pyridin-3-ylcarbamoyl)-[1,1';4',1"]terphenyl-4"-yl ester
40. 6-Methyl-4'-pyridin-2-yl-biphenyl-3-carboxylic acid (6-methoxy-pyridin-3-yl)-amide
41. 6-Chloro-[1,1';4',1"]terphenyl-3-carboxylic acid (piperidin-4-ylmethyl)-amide
42. 6-Chloro-[1,1';4',1"]terphenyl-3-carboxylic acid (6-hydroxymethyl-pyridin-3-yl)-amide
43. 6-Chloro-[1,1';4',1"]terphenyl-3-carboxylic acid piperidin-4-ylamide
44. 6-Chloro-[1,1';4',1"]terphenyl-3-carboxylic acid (6-methylsulfanyl-pyridin-3-yl)-amide
45. 6-Chloro-4'-(2-methyl-2H-tetrazol-5-yl)-biphenyl-3-carboxylic acid (6-methoxy-pyridin-3-yl)-amide
46. 3-[2-(6-Chloro-[1,1';4',1"]terphenyl-3-yl)-2-oxo-ethyl]-benzoic acid methyl ester
47. 6-Chloro-[1,1';4',1"]terphenyl-3-carboxylic acid [6-(4-methyl-piperazin-1-yl)-pyridin-3-yl]-amide
48. 6-Methyl-[1,1';4',1"]terphenyl-3-carboxylic acid (5-chloro-pyridin-2-yl)-amide
49. 6-Chloro-[1,1';4',1"]terphenyl-3-carboxylic acid (5-phenyl-[1,3,4]oxadiazol-2-yl)-amide
50. 6-Chloro-4'-dimethylaminomethyl-biphenyl-3-carboxylic acid (6-methoxy-pyridin-3-yl)-amide
51. 6-Chloro-3"-dimethylaminomethyl-[1,1';4',1"]terphenyl-3-carboxylic acid (4-methoxy-phenyl)-amide
52. 6-Chloro-[1,1';4',1"]terphenyl-3-carboxylic acid (2-dimethylamino-ethyl)-pyridin-3-yl-amide
53. 6"-Chloro-[1,1';4',1"]terphenyl-3"-carboxylic acid (6-methanesulfonyl-benzothiazol-2-yl)-amide
54. 4'-Bromo-6-chloro-biphenyl-3-carboxylic acid pyrazin-2-ylamide
55. 6-Chloro-4'-methanesulfinyl-biphenyl-3-carboxylic acid (6-methoxy-pyridin-3-yl)-amide
56. 6-Chloro-4'-nitro-biphenyl-3-carboxylic acid (6-methoxy-pyridin-3-yl)-amide
57. 4'-Benzyloxy-6-chloro-biphenyl-3-carboxylic acid (6-methoxy-pyridin-3-yl)-amide
58. 6-Chloro-[1,1';4',1"]terphenyl-3-carboxylic acid (tetrahydro-furan-2-ylmethyl)-amide
59. (6-Chloro-[1,1';4',1"]terphenyl-3-yl)-(3-dimethylamino-pyrrolidin-1-yl)-methanone TABLE I-continued 60. 6"-Chloro-[1,1';4',1"]terphenyl-3"-carboxylic acid [3-(2-methyl-[1,3]dioxolan-2-yl)-phenyl]-amide
61. 6-Chloro-biphenyl-3,3'-dicarboxylic acid 3'-amide 3-[(6-methoxy-pyridin-3-yl)-amide]
62. 6-Chloro-4'-(5-hydroxymethyl-pyridin-3-yl)-biphenyl-3-carboxylic acid (6-methoxy-pyridin-3-yl)-amide
63. 4'-Bromo-6-chloro-biphenyl-3-carboxylic acid (6-methoxy-pyridin-3-yl)-amide
64. 4"-Benzyloxy-6-chloro-[1,1';4',1"]terphenyl-3-carboxylic acid (6-methoxy-pyridin-3-yl)-amide
65. 6-Chloro-[1,1';4',1"]terphenyl-3-carboxylic acid pyridin-3-ylamide
66. 6-Chloro-[1,1';4',1"]terphenyl-3-carboxylic acid (furan-2-ylmethyl)-amide
67. 6"-Chloro-[1,1';4',1"]terphenyl-3"-carboxylic acid quinolin-6-ylamide
68. 6-Chloro-[1,1';3',1"]terphenyl-3-carboxylic acid (6-methoxy-pyridin-3-yl)-amide
69. 6-Chloro-[1,1';4',1"]terphenyl-3-carboxylic acid (3-fluoro-4-methoxy-phenyl)-amide
70. 6-Chloro-4'-pyrimidin-5-yl-biphenyl-3-carboxylic acid (6-methoxy-pyridin-3-yl)-amide
71. 6-Chloro-[1,1';4',1"]terphenyl-3-carboxylic acid [6-(2-dimethylamino-ethylsulfanyl)-pyridin-3-yl]-amide
72. 6-Chloro-4'-methanesulfonyl-biphenyl-3-carboxylic acid pyrazin-2-ylamide
73. 2-Chloro-5-(6-methoxy-pyridin-3-ylcarbamoyl)-[1,1';4',1"]terphenyl-3"-carboxylic acid
74. 4"-Aminomethyl-6-chloro-[1,1';4',1"]terphenyl-3-carboxylic acid (6-methoxy-pyridin-3-yl)-amide
75. 6-Chloro-3"-formyl-[1,1';4',1"]terphenyl-3-carboxylic acid (6-methoxy-pyridin-3-yl)-amide
76. 6-Chloro-4'-(5-dimethylaminomethyl-pyridin-3-yl)-biphenyl-3-carboxylic acid (6-methoxy-pyridin-3-yl)-amide
77. 6-Chloro-[1,1';4',1"]terphenyl-3-carboxylic acid methyl-(2-pyridin-2-yl-ethyl)-amide
78. 6-Chloro-[1,1';4',1"]terphenyl-3-carboxylic acid (2-methylsulfanyl-pyrimidin-5-yl)-amide
79. 6"-Chloro-[1,1';4',1"]terphenyl-3"-carboxylic acid (5-chloro-pyrimidin-2-yl)-amide
80. 6"-Chloro-[1,1';4',1"]terphenyl-3"-carboxylic acid (4-ethoxy-phenyl)-amide
81. (3-Amino-pyrrolidin-1-yl)-(6-chloro-[1,1';4',1"]terphenyl-3-yl)-methanone
82. [1,1';4',1"]Terphenyl-3"-carboxylic acid (2-pyrrolidin-1-yl-ethyl)-amide
83. 6-Chloro-[1,1';4',1"]terphenyl-3-carboxylic acid [3-(2-morpholin-4-yl-acetylamino)-phenyl]-amide
84. 6-Chloro-4'-pyridin-2-yl-biphenyl-3-carboxylic acid (6-oxo-1,6-dihydro-pyridin-3-yl)-amide
85. 6-Chloro-[1,1';4',1"]terphenyl-3-carboxylic acid [4-(2-morpholin-4-yl-acetylamino)-phenyl]-amide
86. 6-Chloro-[1,1';4',1"]terphenyl-3-carboxylic acid [1-(2-bromo-acetyl)-piperidin-4-ylmethyl]-amide
87. 6"-Chloro-[1,1';4',1"]terphenyl-3"-carboxylic acid (3-methyl-isoxazol-5-yl)-amide
88. 6-Chloro-[1,1';4',1"]terphenyl-3-carboxylic acid (5-bromo-pyridin-2-yl)-amide
89. 6"-Chloro-[1,1';4',1"]terphenyl-3"-carboxylic acid (6-morpholin-4-yl-pyridin-3-yl)-amide
90. 6-Chloro-[1,1';4',1"]terphenyl-3-carboxylic acid (6-dimethylaminomethyl-pyridin-3-yl)-amide
91. 6-Chloro-[1,1';4',1"]terphenyl-3-carboxylic acid (6-trifluoromethyl-pyridin-3-yl)-amide
92. 6-Fluoro-[1,1';4',1"]terphenyl-3-carboxylic acid (6-methoxy-pyridin-3-yl)-amide
93. 6"-Chloro-2'-fluoro-[1,1';4',1"]terphenyl-3"-carboxylic acid (2-pyrrolidin-1-yl-ethyl)-amide
94. 4'-Bromomethyl-6-chloro-biphenyl-3-carboxylic acid (6-methoxy-pyridin-3-yl)-amide
95. 6-Chloro-[1,1';4',1"]terphenyl-3-carboxylic acid (2-dimethylamino-ethyl)-amide
96. 6"-Chloro-[1,1';4',1"]terphenyl-3"-carboxylic acid (3-methoxy-phenyl)-amide
97. [1-(6-Chloro-[1,1';4',1"]terphenyl-3-carbonyl)-pyrrolidin-3-yl]-carbamic acid tert-butyl ester
98. 6-Chloro-[1,1';4',1"]terphenyl-3-carboxylic acid (5-methyl-isoxazol-3-yl)-amide
99. 6-Chloro-[1,1';4',1"]terphenyl-3-carboxylic acid (6-ethenesulfinyl-pyridin-3-yl)-amide
100. 6-Chloro-4'-methanesulfonyl-biphenyl-3-carboxylic acid (6-chloro-pyridin-3-yl)-amide
101. 6-Chloro-4'-sulfamoyl-biphenyl-3-carboxylic acid (6-methoxy-pyridin-3-yl)-amide
102. 6-Chloro-4'-hydroxy-biphenyl-3-carboxylic acid (6-methoxy-pyridin-3-yl)-amide
103. 6-Chloro-2"-dimethylaminomethyl-[1,1';4',1"]terphenyl-3-carboxylic acid (6-methoxy-pyridin-3-yl)-amide
104. 6-Chloro-[1,1';4',1"]terphenyl-3-carboxylic acid (1-carbamimidoyl-piperidin-4-yl)-amide
105. 6-Chloro-[1,1';4',1"]terphenyl-3-carboxylic acid (2-cyano-ethyl)-amide
106. 6-Biphenyl-4-yl-pyridine-2-carboxylic acid (6-methoxy-pyridin-3-yl)-amide
107. 6"-Chloro-2'-fluoro-[1,1';4',1"]terphenyl-3"-carboxylic acid pyrazin-2-ylamide
108. 6-Chloro-[1,1';4',1"]terphenyl-3-carboxylic acid (2-pyridin-3-yl-ethyl)-amide
109. 6"-Chloro-[1,1';4',1"]terphenyl-3"-carboxylic acid (4-cyano-phenyl)-amide
110. 6-Chloro-[1,1';4',1"]terphenyl-3-carboxylic acid [2-(1H-imidazol-4-yl)-ethyl]-pyrrolidin-2-ylmethyl-amide
111. 6-Biphenyl-4-yl-pyridine-2-carboxylic acid (2-diethylamino-ethyl)-amide TABLE I-continued 112. [1-(6-Chloro-[1,1';4',1'']terphenyl-3-carbonyl)-piperidin-4-ylmethyl]-carbamic acid tert-butyl ester
113. 6-Methoxy-[1,1';4',1'']terphenyl-3-carboxylic acid (6-methoxy-pyridin-3-yl)-amide
114. 6''-Chloro-[1,1';4',1'']terphenyl-3''-carboxylic acid (6-dimethylamino-pyridin-3-yl)-amide
115. 6''-Chloro-[1,1';4',1'']terphenyl-3''-carboxylic acid quinolin-8-ylamide
116. 4-Chloro-3-naphthalen-2-yl-N-piperidin-4-ylmethyl-benzamide
117. 6-Chloro-4'-pyridin-4-yl-biphenyl-3-carboxylic acid (2-pyrrolidin-1-yl-ethyl)-amide
118. 6''-Chloro-2'-fluoro-[1,1';4',1'']terphenyl-3''-carboxylic acid (piperidin-4-ylmethyl)-amide
119. 6''-Chloro-[1,1';4',1'']terphenyl-3''-carboxylic acid (3-acetyl-phenyl)-amide
120. 6''-Chloro-[1,1';4',1'']terphenyl-3''-carboxylic acid benzo[1,3]dioxol-5-ylamide
121. 6-Chloro-[1,1';4',1'']terphenyl-3-carboxylic acid (3,4,5-trimethoxy-phenyl)-amide
122. 6-Chloro-4''-methanesulfonyl-[1,1';4',1'']terphenyl-3-carboxylic acid (6-methoxy-pyridin-3-yl)-amide
123. (6-Chloro-[1,1';4',1'']terphenyl-3-yl)-[1,4]diazepan-1-yl-methanone
124. 6-Chloro-[1,1';4',1'']terphenyl-3-carboxylic acid pyridin-4-ylamide
125. 6-Chloro-4'-methanesulfonyl-biphenyl-3-carboxylic acid (2-dimethylamino-quinolin-6-yl)-amide
126. 6-Hydroxy-[1,1';4',1'']terphenyl-3-carboxylic acid (6-methoxy-pyridin-3-yl)-amide
127. (3-{[(6-Chloro-[1,1';4',1'']terphenyl-3-carbonyl)-amino]-methyl}-benzyl)-carbamic acid tert-butyl ester
128. 6''-Chloro-[1,1';4',1'']terphenyl-3''-carboxylic acid [4-(acetyl-methyl-amino)-phenyl]-amide
129. 6-Chloro-[1,1';4',1'']terphenyl-3-carboxylic acid (2-methanesulfonyl-pyrimidin-5-yl)-amide
130. 6-Chloro-3'',4'',5''-methanesulfonyl-[1,1';4',1'']terphenyl-3-carboxylic acid (6-methoxy-pyridin-3-yl)-amide
131. 5-(3-Fluorophenyl)-3'-fluoro-biphenyl-3-carboxylic acid (6-methoxy-pyridin-3-yl)-amide
132. 6-Chloro-[1,1';4',1'']terphenyl-3-carboxylic acid (6-methanesulfinyl-pyridin-3-yl)-amide
133. 6-Biphenyl-4-yl-pyridine-2-carboxylic acid (6-chloro-pyridin-3-yl)-amide
134. 6''-Chloro-[1,1';4',1'']terphenyl-3''-carboxylic acid cyclopentylamide
135. 6-Chloro-[1,1';4',1'']terphenyl-3-carboxylic acid {2-[4-(3-chloro-5-trifluoromethyl-pyridin-2-yl)-piperazin-1-yl]-ethyl}-amide
136. (6-Chloro-[1,1';4',1'']terphenyl-3-yl)-(3-pyridin-4-yl-pyrrolidin-1-yl)-methanone
137. 6-Chloro-[1,1';4',1'']terphenyl-3-carboxylic acid (pyridin-4-ylmethyl)-amide
138. 6''-Chloro-[1,1';4',1'']terphenyl-3''-carboxylic acid (3-phenyl-[1,2,4]thiadiazol-5-yl)-amide
139. 6''-Chloro-[1,1';4',1'']terphenyl-3''-carboxylic acid (5-trifluoromethyl-[1,3,4]thiadiazol-2-yl)-amide
140. 6''-Chloro-[1,1';4',1'']terphenyl-3''-carboxylic acid (4-methanesulfonyl-phenyl)-amide
141. (6-Chloro-[1,1';4',1'']terphenyl-3-yl)-piperazin-1-yl-methanone
142. 4-(6-Chloro-[1,1';4',1'']terphenyl-3-carbonyl)-piperazine-1-carboxamidine
143. 6-Biphenyl-4-yl-pyridine-2-carboxylic acid (4-methoxy-phenyl)-amide
144. 6-Chloro-[1,1';4',1'']terphenyl-3-carboxylic acid (3-chloro-4-methoxy-phenyl)-amide
145. 6-Chloro-3'-methanesulfonyl-biphenyl-3-carboxylic acid (6-methoxy-pyridin-3-yl)-amide
146. 6-Chloro-3'-hydroxymethyl-biphenyl-3-carboxylic acid (6-methoxy-pyridin-3-yl)-amide
147. 6-Chloro-[1,1';4',1'']terphenyl-3-carboxylic acid (6-methyl-1-oxy-pyridin-3-yl)-amide
148. 6-Chloro-4'-pyridin-2-yl-biphenyl-3-carboxylic acid (2-dimethylamino-ethyl)-(6-methoxy-pyridin-3-yl)-amide
149. 6-Chloro-3'-dimethylaminomethyl-biphenyl-3-carboxylic acid (6-methoxy-pyridin-3-yl)-amide
150. 6''-Chloro-[1,1';4',1'']terphenyl-3''-carboxylic acid (2,2,2-trifluoro-ethyl)-amide
151. 5-{4-[(6-Chloro-4'-methanesulfonyl-biphenyl-3-carbonyl)-amino]-phenyl}-furan-2-carboxylic acid ethyl ester
152. 6-Chloro-3',4',5'-trimethoxy-biphenyl-3-carboxylic acid (6-methoxy-pyridin-3-yl)-amide
153. 6-Chloro-4'-pyridin-2-yl-biphenyl-3-carboxylic acid (2-pyrrolidin-1-yl-ethyl)-amide
154. 6-Bromomethyl-4'-pyridin-2-yl-biphenyl-3-carboxylic acid (6-methoxy-pyridin-3-yl)-amide
155. 6-Chloro-4'-hydroxymethyl-biphenyl-3-carboxylic acid (6-methoxy-pyridin-3-yl)-amide
156. 6-Chloro-[1,1';4',1'']terphenyl-3-carboxylic acid pyridin-2-ylamide
157. 6''-Chloro-[1,1';4',1'']terphenyl-3''-carboxylic acid (4-acetyl-phenyl)-amide
158. 6''-Chloro-[1,1';4',1'']terphenyl-3''-carboxylic acid (3-methylsulfanyl-phenyl)-amide
159. 4-[(6-Chloro-[1,1';4',1'']terphenyl-3-carbonyl)-amino]-benzoic acid methyl ester
160. 6-Chloro-4'-methanesulfonyl-biphenyl-3-carboxylic acid (4-oxazol-2-yl-phenyl)-amide
161. 3'-Amino-6-chloro-biphenyl-3-carboxylic acid (6-methoxy-pyridin-3-yl)-amide
162. 6-Chloro-[1,1';4',1'']terphenyl-3-carboxylic acid (6-methoxy-pyrimidin-4-yl)-amide
163. 6''-Chloro-[1,1';4',1'']terphenyl-3''-carboxylic acid (5-ethyl-[1,3,4]thiadiazol-2-yl)-amide
164. 6-Biphenyl-4-yl-pyridine-2-carboxylic acid (2-dimethylamino-ethyl)-amide
165. 4-Chloro-3-(5-hydroxymethyl-pyridin-3-yl)-N-(6-methoxy-pyridin-3-yl)-benzamide TABLE I-continued 166. [(6"-Chloro-[1,1';4',1"]terphenyl-3"-carbonyl)-phenyl-amino]-acetic acid ethyl ester
167. 4-Methyl-piperazine-1-carboxylic acid 5-(6-methoxy-pyridin-3-ylcarbamoyl)-[1,1';4',1"]terphenyl-2-yl ester
168. 6-Chloro-[1,1';4',1"]terphenyl-3-carboxylic acid (2-pyridin-3-yl-ethyl)-amide
169. 6-Chloro-[1,1';4',1"]terphenyl-3-carboxylic acid (6-methoxy-1-oxy-pyridin-3-yl)-amide
170. 6"-Chloro-[1,1';4',1"]terphenyl-3"-carboxylic acid benzo[1,2,5]thiadiazol-4-ylamide
171. (4-Aminomethyl-piperidin-1-yl)-(6-chloro-[1,1';4',1"]terphenyl-3-yl)-methanone
172. 6-Chloro-[1,1';4',1"]terphenyl-3-carboxylic acid (6-methanesulfonyl-pyridin-3-yl)-amide
173. 6-Chloro-4'-methanesulfonyl-biphenyl-3-carboxylic acid (1-methyl-1H-benzoimidazol-5-yl)-amide
174. Methanesulfonic acid 5-(6-methoxy-pyridin-3-ylcarbamoyl)-[1,1';4',1"]terphenyl-2-yl ester
175. 6"-Chloro-[1,1';4',1"]terphenyl-3"-carboxylic acid (4-cyanomethyl-phenyl)-amide
176. 6-Chloro-4'-methanesulfonyl-biphenyl-3-carboxylic acid (4,5-dihydro-thiazol-2-yl)-amide
177. 6-Chloro-[1,1';4',1"]terphenyl-3-carboxylic acid (6-ethenesulfonyl-pyridin-3-yl)-amide
178. 1-(6"-Chloro-[1,1';4',1"]terphenyl-3"-carbonyl)-piperidine-4-carboxylic acid ethyl ester
179. 6-Chloro-[1,1';4',1"]terphenyl-3-carboxylic acid (4-chloro-phenyl)-amide
180. 4-Chloro-3-(5-dimethylaminomethyl-pyridin-3-yl)-N-(6-methoxy-pyridin-3-yl)-benzamide
181. 6-Chloro-[1,1';4',1"]terphenyl-3-carboxylic acid (3,4-dichloro-phenyl)-amide
182. {2-[(6"-Chloro-[1,1';4',1"]terphenyl-3"-carbonyl)-amino]-thiazol-4-yl}-methoxyimino-acetic acid ethyl ester
183. 6"-Chloro-[1,1';4',1"]terphenyl-3"-carboxylic acid (2-chloro-5-cyano-phenyl)-amide
184. 6"-Chloro-[1,1';4',1"]terphenyl-3"-carboxylic acid (3-ethoxy-phenyl)-amide
185. 4-(6-Chloro-[1,1';4',1"]terphenyl-3-carbonyl)-[1,4]diazepane-1-carboxamidine
186. 6-Chloro-4'-pyridin-4-yl-biphenyl-3-carboxylic acid pyrazin-2-ylamide
187. {2-[(6-Chloro-[1,1';4',1"]terphenyl-3-carbonyl)-amino]-ethyl}-trimethyl-ammonium
188. 6"-Chloro-[1,1';4',1"]terphenyl-3"-carboxylic acid isoquinolin-5-ylamide
189. (6-Chloro-[1,1';4',1"]terphenyl-3-yl)-(2-pyridin-4-yl-pyrrolidin-1-yl)-methanone
190. 6-Chloro-4'-cyano-biphenyl-3-carboxylic acid (2-pyrrolidin-1-yl-ethyl)-amide
191. 6-Chloro-[1,1';4',1"]terphenyl-3-carboxylic acid (pyridin-3-ylmethyl)-amide
192. 6"-Chloro-[1,1';4',1"]terphenyl-3"-carboxylic acid (3,4-dimethyl-isoxazol-5-yl)-amide
193. 3-[(6"-Chloro-[1,1';4',1"]terphenyl-3"-carbonyl)-amino]-pyrazine-2-carboxylic acid methyl ester
194. 6"-Chloro-[1,1';4',1"]terphenyl-3"-carboxylic acid (3,5-dimethoxy-phenyl)-amide
195. 6-Chloro-[1,1';4',1"]terphenyl-3-carboxylic acid (4-chloro-phenyl)-methyl-amide
196. 6-Chloro-4'-methanesulfonyl-biphenyl-3-carboxylic acid (3,4,5-trimethoxy-phenyl)-amide
197. 4-Chloro-N-(6-methoxy-pyridin-3-yl)-3-pyridin-3-yl-benzamide
198. 4-[(6-Chloro-[1,1';4',1"]terphenyl-3-carbonyl)-amino]-piperidine-1-carboxylic acid tert-butyl ester
199. 6-Chloro-[1,1';4',1"]terphenyl-3-carboxylic acid (1H-imidazol-4-ylmethyl)-amide
200. 6-Chloro-[1,1';4',1"]terphenyl-3-carboxylic acid (5-methylsulfanyl-[1,3,4]thiadiazol-2-yl)-amide
201. 6-Chloro-[1,1';4',1"]terphenyl-3-carboxylic acid (pyridin-2-ylmethyl)-amide
202. 2-[2-(6-Chloro-[1,1';4',1"]terphenyl-3-carbonyl)-1,2,3,4-tetrahydro-isoquinoline-3-carbonyl]-1,2,3,4-tetrahydro-isoquinoline-3-carboxylic acid [2-(1H-imidazol-4-yl)-ethyl]-amide
203. 2-(6-Chloro-[1,1';4',1"]terphenyl-3-carbonyl)-1,2,3,4-tetrahydro-isoquinoline-3-carboxylic acid [2-(1H-imidazol-4-yl)-ethyl]-amide
204. 6-Chloro-[1,1';4',1"]terphenyl-3-carboxylic acid {5-amino-2-[2-(1H-imidazol-4-yl)-ethylcarbamoyl]-indan-2-yl}-amide
205. 2-(6-Chloro-[1,1';4',1"]terphenyl-3-carbonyl)-1,2,3,4-tetrahydro-isoquinoline-3-carboxylic acid {2-cyclohexyl-1-[2-(1H-imidazol-4-yl)-ethylcarbamoyl]-ethyl}-amide
206. 6-Chloro-4'-pyridin-4-yl-biphenyl-3-carboxylic acid pyrazin-2-ylamide
207. 6-Chloro-[1,1';4',1"]terphenyl-3-carboxylic acid [1,3,4]thiadiazol-2-ylamide
208. 6-Chloro-[1,1';4',1"]terphenyl-3-carboxylic acid (2-pyridin-4-yl-ethyl)-amide
209. 6-Chloro-[1,1';4',1"]terphenyl-3-carboxylic acid {1-[2-(1H-imidazol-4-yl)-ethylcarbamoyl]-3-phenyl-propyl}-amide
210. 6"-Chloro-[1,1';4',1"]terphenyl-3"-carboxylic acid (2-chloro-pyridin-3-yl)-amide
211. 6-Chloro-[1,1';4',1"]terphenyl-3-carboxylic acid (6-chloro-pyridazin-3-yl)-amide
212. 6"-Chloro-[1,1';4',1"]terphenyl-3"-carboxylic acid (4-methoxy-phenyl)-methyl-amide
213. 3-[(6"-Chloro-[1,1';4',1"]terphenyl-3"-carbonyl)-amino]-benzoic acid ethyl ester
214. 6-Chloro-[1,1';4',1"]terphenyl-3-carboxylic acid (5-methyl-[1,3,4]thiadiazol-2-yl)-amide
215. 2-[(6"-Chloro-2'-fluoro-[1,1';4',1"]terphenyl-3"-carbonyl)-amino]-3-cyclohexyl-propionic acid
216. 4-Phenyl-pyridine-2-carboxylic acid (6-methoxy-pyridin-3-yl)-amide
217. 6-Chloro-[1,1';4',1"]terphenyl-3-carboxylic acid (1-aza-bicyclo[2.2.2]oct-3-yl)-amide
218. (6-Chloro-[1,1';4',1"]terphenyl-3-yl)-(5-nitro-2,3-dihydro-indol-1-yl)-methanone
219. 6-Chloro-N-(6-methoxy-pyridin-3-yl)-5-p-tolyl-nicotinamide
220. 2-[(5"-Chloro-2'-fluoro-[1,1';4',1"]terphenyl-2"-carbonyl)-amino]-3-cyclohexyl-propionic acid TABLE I-continued 221. 6"-Chloro-[1,1';4',1"]terphenyl-3"-carboxylic acid [2-(2,5-dioxo-pyrrolidin-1-yl)-phenyl]-amide
222. (6"-Chloro-[1,1';4',1"]terphenyl-3"-yl)-(4-phenyl-piperazin-1-yl)-methanone
223. 2-[(6-Chloro-[1,1';3',1"]terphenyl-3-carbonyl)-amino]-4-phenyl-butyric acid
224. 6"-Chloro-[1,1';4',1"]terphenyl-3"-carboxylic acid benzo[1,3]dioxol-5-yl-ethyl-amide
225. 6"-Chloro-[1,1';4',1"]terphenyl-3"-carboxylic acid [4-(4-nitro-benzenesulfonyl)-phenyl]-amide
226. 4-Chloro-N-(6-methoxy-pyridin-3-yl)-3-pyrimidin-5-yl-benzamide
227. 4-p-Tolyl-pyridine-2-carboxylic acid (6-methoxy-pyridin-3-yl)-amide
228. 6-Chloro-4'-methanesulfonyl-biphenyl-3-carboxylic acid (tetrahydro-furan-2-ylmethyl)-amide
229. 4-(3-Fluoro-phenyl)-pyridine-2-carboxylic acid (6-methoxy-pyridin-3-yl)-amide
230. 6-Chloro-4'-methanesulfonyl-biphenyl-3-carboxylic acid (3-methoxy-4-oxazol-5-yl-phenyl)-amide
231. 4-[(6"-Chloro-[1,1';4',1"]terphenyl-3"-carbonyl)-amino]-benzoic acid ethyl ester
232. 2-[(6-Chloro-4'-phenoxy-biphenyl-3-carbonyl)-amino]-4-phenyl-butyric acid
233. 6-Biphenyl-4-yl-pyridine-2-carboxylic acid pyrazin-2-ylamide
234. {4-[(6"-Chloro-[1,1';4',1"]terphenyl-3"-carbonyl)-amino]-phenyl}-acetic acid ethyl ester
235. 2-[(4'-tert-Butyl-biphenyl-4-carbonyl)-amino]-indan-2-carboxylic acid
236. 2-[(6-Chloro-[1,1';3',1"]terphenyl-3-carbonyl)-amino]-3-cyclohexyl-propionic acid
237. 2-{2-[(6-Chloro-[1,1';4',1"]terphenyl-3-carbonyl)-amino]-4-phenyl-butyrylamino}-4-phenyl-butyric acid
238. 6-Chloro-[1,1';4',1"]terphenyl-3-carboxylic acid (3-amino-propyl)-amide
239. 2-[(5"-Chloro-2'-fluoro-[1,1';4',1"]terphenyl-2"-carbonyl)-amino]-4-phenyl-butyric acid
240. 3-(6-Chloro-[1,1';4',1"]terphenyl-3-carbonyl)-thiazolidine-4-carboxylic acid
241. 6"-Chloro-[1,1';4',1"]terphenyl-3"-carboxylic acid (5-cyclopropyl-[1,3,4]thiadiazol-2-yl)-amide
242. 6"-Chloro-[1,1';4',1"]terphenyl-3"-carboxylic acid (4-cyano-naphthalen-1-yl)-amide
243. 2-{2-[(6-Chloro-[1,1';4',1"]terphenyl-3-carbonyl)-amino]-4-phenyl-butyrylamino}-3-cyclohexyl-propionic acid
244. 6-Chloro-[1,1';4',1"]terphenyl-3-carboxylic acid [2-(1H-imidazol-4-yl)-ethyl]-piperidin-4-ylmethyl-amide
245. 6-Chloro-biphenyl-3-carboxylic acid [2-(1H-imidazol-4-yl)-ethyl]-amide
246. 6"-Chloro-[1,1';4',1"]terphenyl-3"-carboxylic acid (2-benzenesulfonyl-phenyl)-amide
247. 2-{[2-(6-Chloro-[1,1';4',1"]terphenyl-3-carbonyl)-1,2,3,4-tetrahydro-isoquinoline-3-carbonyl]-amino}-3-(1H-imidazol-4-yl)-propionic acid
248. 2-[(6-Chloro-4'-cyclohexyl-biphenyl-3-carbonyl)-amino]-indan-2-carboxylic acid
249. 2-[(6-Chloro-4'-dimethylamino-biphenyl-3-carbonyl)-amino]-3-cyclohexyl-propionic acid
250. 3-Cyclopropyl-2-[(6,4'-dichloro-biphenyl-3-carbonyl)-amino]-propionic acid
251. 3-(6-Chloro-[1,1';4',1"]terphenyl-3-carbonyl)-thiazolidine-4-carboxylic acid
252. 2-[(6,3',4'-Trichloro-biphenyl-3-carbonyl)-amino]-indan-2-carboxylic acid
253. 2-[(6-Chloro-4'-trifluoromethyl-biphenyl-3-carbonyl)-amino]-indan-2-carboxylic acid
254. 2-[(6-Chloro-3'-trifluoromethyl-biphenyl-3-carbonyl)-amino]-indan-2-carboxylic acid
255. 2-[(6,5'-Dichloro-2'-methoxy-biphenyl-3-carbonyl)-amino]-indan-2-carboxylic acid
256. 5'-(1-Carboxy-2-cyclohexyl-ethylcarbamoyl)-2'-chloro-biphenyl-4-carboxylic acid
257. 2-[5'-(1-Carboxy-2-cyclohexyl-ethylcarbamoyl)-2'-chloro-biphenyl-4-yl]-quinoline-4-carboxylic acid
258. 2-[(6-Chloro-4'-methylsulfanyl-biphenyl-3-carbonyl)-amino]-indan-2-carboxylic acid
259. 2-[(4'-Benzyloxy-6-chloro-biphenyl-3-carbonyl)-amino]-4-phenyl-butyric acid
260. 2-[(6-Chloro-3'-methoxy-biphenyl-3-carbonyl)-amino]-indan-2-carboxylic acid
261. 2-[(6,3',5'-Trichloro-biphenyl-3-carbonyl)-amino]-indan-2-carboxylic acid
262. 2-{[2-(6-Chloro-[1,1';4',1"]terphenyl-3-carbonyl)-1,2,3,4-tetrahydro-isoquinoline-3-carbonyl]-amino}-3-(1H-imidazol-4-yl)-propionic acid
263. 2-(3-Benzo[1,3]dioxol-5-yl-4-chloro-benzoylamino)-indan-2-carboxylic acid
264. 2-[(2-Ethyl-biphenyl-4-carbonyl)-amino]-indan-2-carboxylic acid
265. 2-[(4'-Ethyl-biphenyl-4-carbonyl)-amino]-indan-2-carboxylic acid
266. 2-[(6,2',3',5'-Tetrachloro-biphenyl-3-carbonyl)-amino]-indan-2-carboxylic acid
267. 2-[(Biphenyl-4-carbonyl)-amino]-indan-2-carboxylic acid
268. 2-[(4'-Cyano-biphenyl-4-carbonyl)-amino]-indan-2-carboxylic acid
269. 2-[(6,3',5'-Trichloro-biphenyl-3-carbonyl)-amino]-indan-2-carboxylic acid
270. 5'-(2-Carboxy-indan-2-ylcarbamoyl)-2'-chloro-biphenyl-3-carboxylic acid methyl ester
271. 6-Chloro-4'-(1H-tetrazol-5-yl)-biphenyl-3-carboxylic acid (6-methoxy-pyridin-3-yl)-amide
272. 2-Biphenyl-4-yl-N-(6-methoxy-pyridin-3-yl)-isonicotinamide
273. N-(6-Methoxy-pyridin-3-yl)-5-p-tolyl-nicotinamide
274. 2-(3-Fluoro-phenyl)-N-(6-methoxy-pyridin-3-yl)-isonicotinamide
275. 5-(3-Fluoro-phenyl)-N-(6-methoxy-pyridin-3-yl)-nicotinamide
276. 6-Chloro-5-(3-fluoro-phenyl)-N-(6-methoxy-pyridin-3-yl)-nicotinamide
277. N-(6-Methoxy-pyridin-3-yl)-2-phenyl-isonicotinamide
278. N-(6-Methoxy-pyridin-3-yl)-5-phenyl-nicotinamide
279. 5-Biphenyl-4-yl-N-(6-methoxy-pyridin-3-yl)-nicotinamide
280. N-(6-Methoxy-pyridin-3-yl)-6-p-tolyl-nicotinamide TABLE I-continued 281. N-(6-Methoxy-pyridin-3-yl)-2-p-tolyl-isonicotinamide
282. N-(6-Methoxy-pyridin-3-yl)-6-phenyl-nicotinamide
283. 6-(3-Fluoro-phenyl)-N-(6-methoxy-pyridin-3-yl)-nicotinamide
284. 6-Fluoro-[1,1';4',1'']terphenyl-3-carboxylic acid (6-methoxy-pyridin-3-yl)-amide
285. 2'-Chloro-5'-(6-methoxy-pyridin-3-ylcarbamoyl)-biphenyl-3-carboxylic acid
286. (6''-Chloro-[1,1';4',1'']terphenyl-3''-yl)-(6-nitro-2,3-dihydro-indol-1-yl)-methanone
287. 8-(6''-Chloro-[1,1';4',1'']terphenyl-3''-carbonyl)-4-methyl-5,6,7,8-tetrahydro-1-oxa-8-aza-anthracen-2-one
288. 1-(6-Chloro-[1,1';4',1'']terphenyl-3-carbonyl)-octahydro-indole-2-carboxylic acid
289. 4-[(6-Chloro-[1,1';4',1'']terphenyl-3-carbonyl)-amino]-tetrahydro-pyran-4-carboxylic acid
290. 1-[(6-Chloro-[1,1';4',1'']terphenyl-3-carbonyl)-amino]-4-hydroxy-cyclohexanecarboxylic acid
291. 4-[(6-Chloro-[1,1';4',1'']terphenyl-3-carbonyl)-amino]-piperidine-4-carboxylic acid
292. 1-[(6-Chloro-[1,1';4',1'']terphenyl-3-carbonyl)-amino]-3-hydroxy-cyclopentanecarboxylic acid
293. 6-Chloro-[1,1';4',1'']terphenyl-3-carboxylic acid (6-hydroxymethyl-pyridin-3-yl)-amide
294. 6-Chloro-4'-pyridin-2-yl-biphenyl-3-carboxylic acid (6-methoxy-pyridin-3-yl)-amide
295. 6-(2-Fluoro-biphenyl-4-yl)-N-(6-methoxy-pyridin-3-yl)-nicotinamide
296. 6-Chloro-[1,1';4',1'']terphenyl-3-carboxylic acid N'-pyridin-2-yl-hydrazide
297. N'-(6-Chloro-[1,1';4',1'']terphenyl-3-carbonyl)-hydrazinecarboxylic acid 9H-fluoren-9-ylmethyl ester
298. 6-Chloro-[1,1';4',1'']terphenyl-3-carboxylic acid hydrazide
299. 6-Chloro-[1,1';4',1'']terphenyl-3-carboxylic acid
300. O'-(6-Chloro-[1,1';4',1'']terphenyl-3-carbonyl)-hydroxylaminecarboxylic acid tert-butyl ester
301. 6-Chloro-[1,1';4',1'']terphenyl-3-carboxylic acid [1,2,4]triazol-1-ylamide
302. 2-{2-[(6-Chloro-[1,1';4',1'']terphenyl-3-carbonyl)-amino]-4-phenyl-butyrylamino}-3-cyclohexyl-propionic acid
303. 6''-Chloro-[1,1';4',1'']terphenyl-3''-carboxylic acid (4-methoxy-phenyl)-amide
304. 6-Chloro-[1,1';4',1'']terphenyl-3-carboxylic acid (1-{2-cyclohexyl-1-[2-(1H-imidazol-4-yl)-ethylcarbamoyl]-ethylcarbamoyl}-3-phenyl-propyl)-amide
305. 2-[([1,1';3',1'']Terphenyl-5'-carbonyl)-amino]-indan-2-carboxylic acid
306. 2-[(6-Chloro-2'-trifluoromethyl-biphenyl-3-carbonyl)-amino]-indan-2-carboxylic acid
307. 2-{2-[(6-Chloro-[1,1';4',1'']terphenyl-3-carbonyl)-amino]-4-phenyl-butyrylamino}-3-(1H-imidazol-4-yl)-propionic acid
308. 6-Chloro-[1,1';4',1'']terphenyl-3-carboxylic acid [6-(4-methyl-piperazin-1-ylmethyl)-pyridin-3-yl]-amide
309. {2-[(6''-Chloro-[1,1';4',1'']terphenyl-3''-carbonyl)-amino-thiazol-4-yl}-acetic acid ethyl ester
310. 6''-Chloro-[1,1';4',1'']terphenyl-3''-carboxylic acid cyclopropylmethyl-amide
311. 6''-Chloro-[1,1';4',1'']terphenyl-3''-carboxylic acid cyclopropylamide
312. 2-[4-Chloro-2-(4-ethyl-phenylethynyl)-benzoylamino]-4-phenyl-butyric acid
313. 4-Chloro-N-[2-(1H-imidazol-4-yl)-ethyl]-3-phenylethynyl-benzamide
314. 2-[4-Chloro-3-(4-chloro-phenylethynyl)-benzoylamino]-4-phenyl-butyric acid
315. 2-[2-(4-Chloro-3-styryl-benzoylamino)-4-phenyl-butyrylamino]-3-cyclohexyl-propionic acid
316. 2-(4-Chloro-3-phenylethynyl-benzoylamino)-4-phenyl-butyric acid
317. 2-(4-Chloro-3-phenylethynyl-benzoylamino)-4-hydroxy-butyric acid
318. 2-(4-Chloro-3-m-tolylethynyl-benzoylamino)-4-phenyl-butyric acid
319. 2-(4-Chloro-3-phenylethynyl-benzoylamino)-3-cyclopropyl-propionic acid
320. 2-[(6''-Chloro-[1,1';4',1'']terphenyl-3''-carbonyl)-amino]-indan-2-carboxylic acid
321. 2-[(6''-Chloro-[1,1';4',1'']terphenyl-3''-carbonyl)-methyl-amino]-propionic acid
322. 1-[(6''-Chloro-[1,1';4',1'']terphenyl-3''-carbonyl)-amino]-cyclopropanecarboxylic acid
323. 3-[(6''-Chloro-[1,1';4',1'']terphenyl-3''-carbonyl)-amino]-propionic acid
324. 2-{[4-Chloro-3-(4-chloro-phenylethynyl)-benzoyl]-cyclohexyl-amino}-propionic acid
325. 2-[(4-Chloro-3-phenylethynyl-benzoyl)-cyclohexyl-amino]-propionic acid
326. 2-(4-Chloro-3-phenylethynyl-benzoylamino)-indan-2-carboxylic acid
327. 6-Chloro-[1,1';4',1'']terphenyl-3-carboxylic acid
328. {3-[(6-Chloro-[1,1';4',1'']terphenyl-3-carbonyl)-amino]-propyl}-carbamic acid tert-butyl ester
329. O'-(6-Chloro-[1,1';4',1'']terphenyl-3-carbonyl)-hydroxylamine
330. 4-Phenylethynyl-benzoic acid
331. 4-{[(6-Chloro-[1,1';4',1'']terphenyl-3-carbonyl)-amino]-methyl}-piperidine-1-carboxylic acid tert-butyl ester
332. 4-Chloro-3-phenylethynyl-N-pyridin-3-yl-benzamide
333. 2-[4-Chloro-3-(4-trifluoromethyl-phenylethynyl)-benzoylamino]-3-cyclohexyl-propionic acid
334. 4-Chloro-N-methyl-3-phenylethynyl-benzamide
335. 4-Chloro-3-phenylethynyl-benzamide
336. 3-(4-Chloro-3-phenylethynyl-benzoyl)-thiazolidine-4-carboxylic acid
337. 2-(6''-Chloro-[1,1';4',1'']terphenyl-3''-carbonyl)-1,2,3,4-tetrahydro-isoquinoline-1-carboxylic acid
338. 6-Chloro-[1,1';4',1'']terphenyl-3-carboxylic acid (6-fluoro-pyridin-3-yl)-amide
339. 6-Chloro-4'-bromo-biphenyl-3-carboxylic acid (6-methoxy-pyridin-3-yl)-amide The compounds of the present invention are readily prepared from commercially available starting material generally following the retrosynthetic schemes outlined in FIG. 1. In both paths, the generation of an aryl acid chloride b or c from commercial acids followed by heteroaromatic amine a addition provides for the desired amide precursors f or g. In Path A, the key step requires a Suzuki style coupling (Miyaura, N. et al., *Synth. Commun.*, 60, 513-516, 1981; Review: Suzuki A. In *Metal-Catalyzed Cross-Coupling Reactions*; Diederich F., Stang P. J. Eds. Wiley-VCH:Weinheim, 1998) that involves catalytic palladium and accessible biphenyl boronic acid substrates. Path B is similar but the key step is a slightly modified Suzuki coupling of a phenyl boronic acid substrate. Synthesis of the proper starting materials is straightforward given accessible sources from commercial vendors. Using the synthetic routes described in FIG. 1, followed by purification by, for example, semi-preparative HPLC methods, the substituted-amide compounds of the present invention are produced.

One skilled in the art will appreciate that substitution of one starting material or reagent for another in the retrosynthetic scheme described in FIG. 1 will provide other compounds that are within the scope of the present invention. Other examples of synthetic routes and starting materials that can be used in the present invention are provided in Examples 1 to 39. Generally, a skilled artisan will recognized that other primary and secondary amines can be used in the synthesis in place of the heteroaromatic amine a. Moreover, a skilled artisan will recognize that substituting the biphenyl boronic acid d with a phenyl boronic acid will produce other various compounds of the present invention. Other variations of the retrosynthetic scheme described in FIG. 1 will be apparent to one skilled in the art.

C. Pharmaceutical Compositions

In addition to compounds that bind inhibit the activity of topoisomerase I and II, the present invention further provides compositions comprising one or more of the above compounds in combination with a pharmaceutically acceptable excipient.

In one embodiment, the present invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include, but are not limited to, solid, semi-solid or liquid media including water and non-toxic organic solvents.

In another embodiment, the present invention provides the subject compounds in the form of a pro-drug, which can be metabolically or chemically converted to the subject compound by the recipient host. A wide variety of pro-drug derivatives are known in the art such as those that rely on hydrolytic cleavage or oxidative activation of the prodrug.

The compositions can be provided in any convenient form, including tablets, capsules, lozenges, troches, hard candies, powders, sprays, creams, suppositories, etc. As such, the compositions, in pharmaceutically acceptable dosage units or in bulk, may be incorporated into a wide variety of containers. For example, dosage units may be included in a variety of containers including capsules, pills, etc.

The pharmaceutical compositions of the present invention are suitable for use in a variety of drug delivery systems. Examples of suitable formulations for use in the present invention are found in *Remington's Pharmaceutical Sciences* (Mack Publishing Company, Philadelphia, Pa., 17th ed., 1985), which is incorporated herein by reference. In addition, for a brief review of methods for drug delivery, (see, Langer, *Science* 249:1527-1533, 1990), which is incorporated herein by reference.

The pharmaceutical compositions of the present invention are intended for parenteral, topical, oral or local administration. In certain aspects, the pharmaceutical compositions are administered parenterally, e.g., intravenously, subcutaneously, intradermally, or intramuscularly. In one embodiment, the invention provides compositions for parenteral administration which comprise a compound of the present invention, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well-known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For solid formulations, compounds of the present invention can be admixed with conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, the compounds of the present invention and antidiabetic agents are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of the present invention or a pharmaceutically acceptable salt.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material.

In powders, the carrier is a finely divided solid that is in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

It will be appreciated that the actual preferred course of therapy will vary according to, inter alia, the mode of administration of the compound of the present invention, the particular formulation being utilized, the mode of administration of the compounds, the particular disease being treated and the particular host being treated. The optimal course of therapy for a given set of conditions can be ascertained by those skilled in the art using conventional course of therapy determination tests and in view of the information set out herein.

III. Method of Use

In yet another aspect, the present invention provides methods of treating cell-proliferative disorders (i.e., cancer) by administering to a subject having such a disease or condition, a therapeutically effective amount of a compound of the present invention. In another preferred embodiment, the present invention provides for methods of treating a subject having cancer selected from the group consisting of leukemia, colon, ovarian, renal, brain and breast cancer by administering to the subject a therapeutically effective amount of a compound of the present invention. In yet another embodiment, the present invention provides methods of treating multi-drug resistant cancers and tumors. The "subject" is defined herein to include animals such as mammals, including, but not limited to, primates (e.g., humans), cows, sheep, goats, horses, dogs, cats, rabbits, rats, mice and the like.

Depending on the subject's condition, the compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment cell proliferative disorders that require inhibition to either topoisomerase I or II inhibitor or both topoisomerase I and II, an appropriate dosage level will generally be about 0.001 to 100 mg per kg patient body weight per day which can be administered in single or multiple doses. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

IV. Examples

A. In Vitro Assays

1. Topo IIα Decatenation Inhibition and Topo I Relaxation Inhibition Assays

Figure 2:
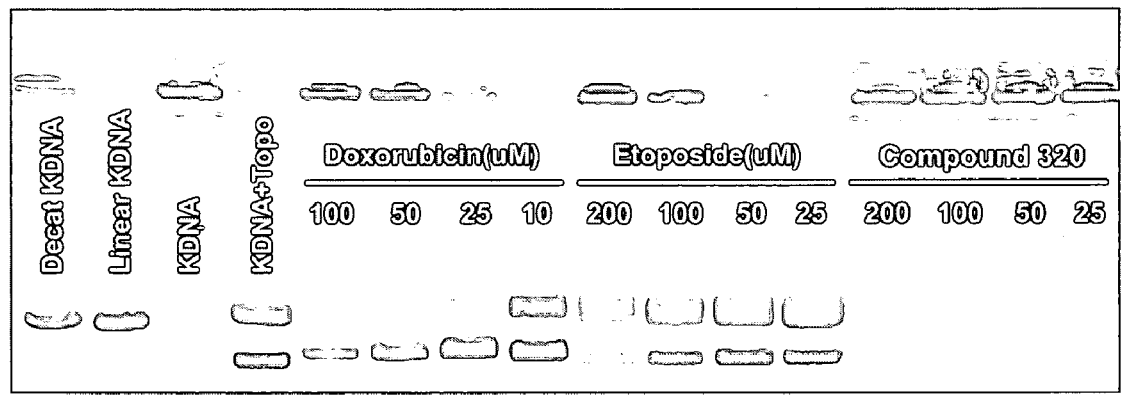
FIG. 2 shows inhibition of Topo IIα decatenation assay results for a compound of the present invention. Note that compound 320 autofluoresces slightly. When present, high molecular weight kDNA has not migrated from the loading well.
Figure 3:
FIG. 3 shows a Topo I dependent relaxation assay results for a compound of the present invention. Lane 1 contains Relaxed pBR322 (sc pBR322+Topo I); Lanes 2 to 8 contain 100, 75, 50, 20, 10, 5, 1 µM respectively of compound 320; Lanes 9 to 14 contain 100, 75, 50, 20, 10, 5 µM respectively of compound 191; and Lane 15-contains supercoiled pBR322, no Topoisomerase I.

The enzyme assays used for determining Topo IIα inhibition was either the ATP-dependent decatenation of high molecular weight kDNA (kinetoplast) as substrate or the relaxation of supercoiled pBR322 each incorporating human Topo IIα (Topogen Inc. Columbus, Ohio) and following literature protocols (Fortune, J. M. et al., *J. Biol. Chem.*, 273 (28), 17643-50 1998; Muller, M. T. et al., *Biochemistry*, 27(22), 8369-79, 1988). The 2.5 Kd mini-circle product derived from the catenated substrate is resolved on an agarose gel with ethidium bromide staining after electrophoresis. Likewise, the relaxed form of pBR322 is resolved from the faster moving supercoiled form during electrophoresis. A sample gel of the decatenation assay is shown in FIG. 2 where there is complete inhibition seen for 320 and partial inhibition for doxorubicin and etoposide. The DNA relaxation activity of Topo I was determined according to the method of Larson et al. (Larsen, A. K. et al., *Biochem. Pharmacol.*, 46(8), 1403-12, 1993) with pBR322 as substrate and human Topo I also supplied by Topogen. The product of this reaction is relaxed plasmid and the topoisomers are resolved on either a native or chloroquine-containing agarose gel as shown in FIG. 3. Further study of 320 was conducted to determine if intercalation was its mechanism of Topo IIα inhibition or whether stabilization of the covalent complex was involved.

2. Topo IIα DNA Intercalation Assay

Gel retardation assays were done on 320 and other biaryl/terphenyl acid compounds, to test for electrophoretic mobility shifts due to the presence of a substance that directly binds DNA. With ethidium bromide (EtBr) and doxorubicin as positive controls included, none of the biaryl acids showed any mobility shift of pBR322 plasmid on gels. Mobility shifts were seen for EtBr and doxorubicin. To confirm these results, a DNA-intercalator displacement assay (Perrin, D. et al., *Biochem. Pharmacol.*, 59(7), 807-19, 2000) was used to measure displacement of EtBr from DNA.

Figure 4:
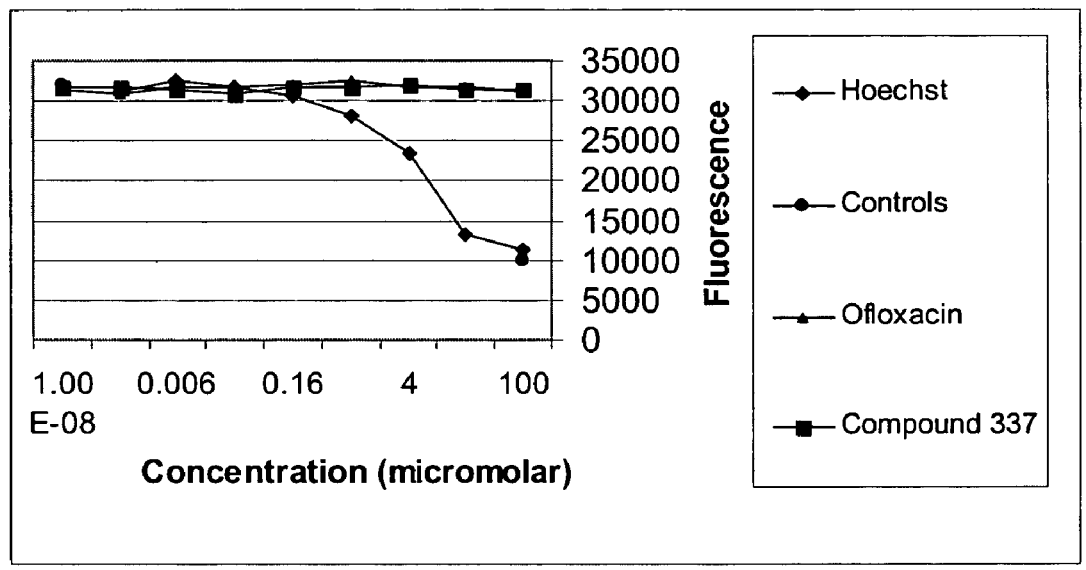
FIG. 4 shows a DNA-intercalator displacement assay results for a compound of the present invention. The curve labeled "Hoechst" corresponds to Hoechst 33258. Controls are: 1) no EtBr (min. fluorescence) and 2) no compound (max. fluorescence).

FIG. 4 shows the lack of intercalator displacement from calf thymus DNA by 337, a terphenyl acid and ofloxacin, a compound known to not be a DNA intercalator. The positive control compound Hoechst 33258 clearly demonstrates displacement of EtBr with a low μM $IC_{50}$ value.

3. Topo IIα DNA Covalent Complex Stabilization Assay

Figure 5:
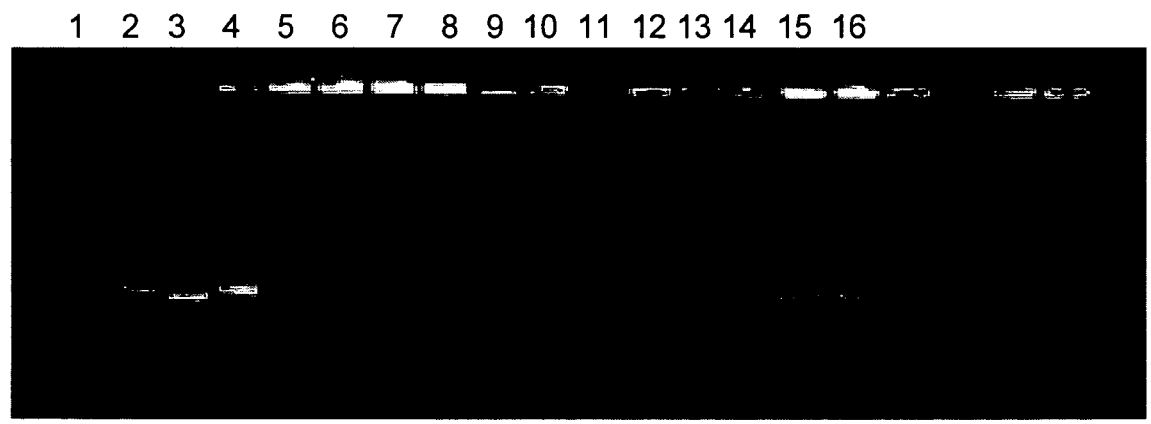
FIG. 5 shows a KDNA decantenation assay results using Topo IIα. Lane 1 contains KDNA; Lane 2 contains nicked minicircle marker; Lane 3 contains linear minicircle; Lane 4 contains KDNA+Topo IIα; Lanes 5 to 8 contain Topo II+Etoposide@100, 50, 25, 10 µM respectively; and Lanes 13 to 16 contain Topo II+320@25, 20, 10, 5 µM respectively.

To determine if the compound 320 stabilizes the TopoIIα-DNA covalent complex, cleavage intermediates are trapped by the addition of SDS to the reaction (Wilson Byl, J. A., et al., *Biochemistry*, 40, 712-718, 2001). After proteinase K digestion to digest any covalently bound Topo, the products are electrophoresed and stained with EtBr. The appearance of an additional band that is a linear form of the 2.5 Kb minicircle product is indicative of a compound's ability to stabilize the covalent complex. As seen in FIG. 5, 320 does not show this linear form and therefore, does not stabilize the covalent complex. Etoposide was used a positive control due to its ability to stabilize the covalent complex and the linear form is present in the wells containing this drug. Similar tests for covalent complex stabilization of Topo I reactions were investigated and these results were similar and showed no apparent stabilization of the covalent complex.

4. Cell Proliferation Assay

Figure 6:
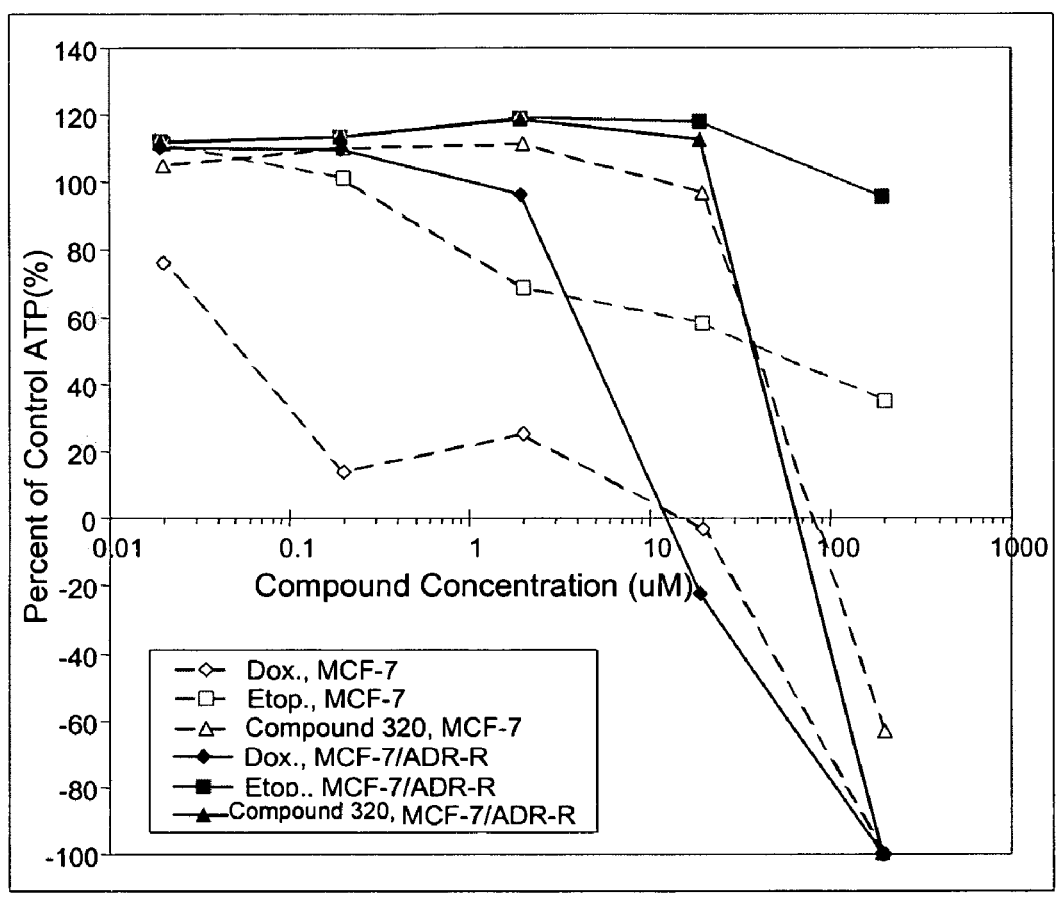
FIG. 6 shows a cell proliferation assay results for a compound of the present invention. The MCF-7 cell line, the MDR cell line, and the MCF-7/ADR cell line were used. Alamar Blue™ was used to quantitate cell viability.

As shown in FIG. 6, 320 was tested against a human-derived tumor line (MCF-7), and one MDR counterpart, MCF-7/ADR with the cells being exposed to compound for 48 hrs. There was no shift in potency from the parent line as compared to the resistant line. In contrast, both etoposide and doxorubicin were substantially less potent (100-fold) in the MCF-7/ADR cell line. The approximate $IC_{50}$ of 320 is 30 μM with the data as shown in FIG. 6, and the shifts in potency for doxorubicin and etoposide are also shown.

B. Xenograft Assay

Figure 7:
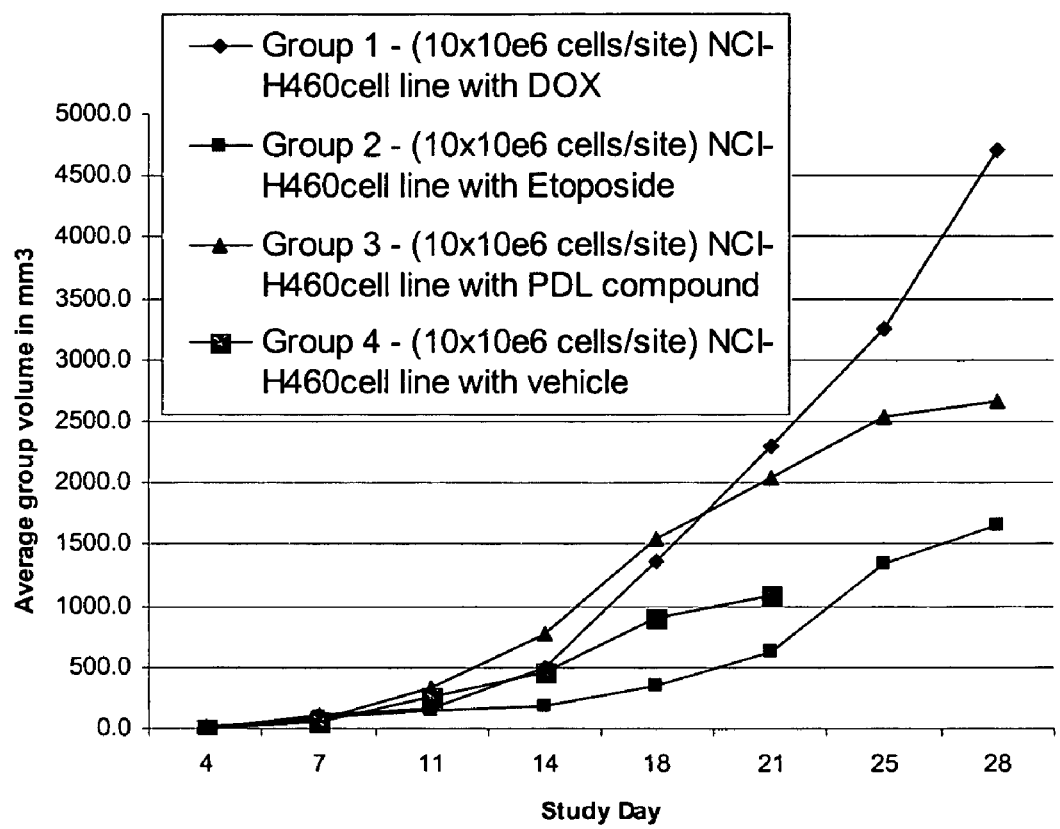
FIG. 7 shows a NCI-H460 xenograft study with compound 320.

A human xenograft study in nude mice was carried out on 320 in comparison to etoposide and doxorubicin and shown in FIG. 7. An acute toxicological study was performed for 320 prior to the xenograft study. Two groups (n=3) of female CD-1 mice were injected intraperitoneally (i.p.) with either 10 or 100 mg/Kg of 320 dissolved in 5% DMSO, 10% PEG400. Two mice in the high dose group survived, and all the low dose mice survived with no visible side effects for seven days at which point they were euthanised. A second MTD study was done by the intravascular (i.v.) route using 4 groups of CD-1 mice for the following: vehicle, 3, 10 and 30 mg/Kg injections which were to be given daily for days 1-5 and study duration of two weeks, at which point survivors would be euthanised. Two animals in the highest dose group survived with one animal dying after 3 injections. All other animals survived to the end of the study.

For the xenograft study, the dosing schedules were 25 mg/Kg 320 given on days 1-5, 35 mg/Kg etoposide (Kraus-Berthier, L. et al., *Clin. Cancer Res.*, 6(1), 297-304, 2000) given on days 7, 10, and 14, and 5 mg/Kg doxorubicin (Kraus-Berthier, L. et al., *Eur. J. Cancer*, 33(11), 1881-7, 1997) given on days 7 and 14, and vehicle control. All injections were by the i.v. route; groups were 5 NCR nu/nu mice. The cell line NCI-H460 was used to produce the tumors that appeared by day 7. The T/C values could not be calculated because the control animals had to be sacrificed on day 21 due to tumor ulceration. FIG. 7 shows a plot of the mean tumor volumes over time that shows the greatest anti-tumor activity with respect to final tumor volume in the etoposide animals, followed by 320, and the least efficacy seen with doxorubicin. Etoposide showed the greatest initial growth delay of the three compounds and the most growth inhibition as well. 320 showed no initial growth delay but after a lag time showed some final growth inhibition. One animal from each of the three drug-treated groups died prior to the end of the study. All survivors to day 28 were euthanised at this time and tumor volumes measured.

EXAMPLES

Chemistry: Unless otherwise noted, all solvents and reagents were obtained from commercial suppliers and used without further purification. Analytical thin layer chromatography (TLC) was performed on aluminum sheets precoated with silica gel obtained from Merck. Visualization was accomplished by using an UV light (254 nm) after dipping in phosphomolybdic acid in MeOH followed by heating. Purification was done by semi-preparative HPLC on a Ranin HPLX instrument with a YMC 2.5 μm C18 analytic column (50×4.6 mm, (10-95% $ACN/H_2O$ 0.1% TFA, 7 min, 3 mL/min)) and a two-channel UV detector (220 and 260 nm). Infrared spectra (IR) were recorded in the range of 4000 $cm^{-1}$ to 600 $cm^{-1}$ using a Perkin-Elmer Spectrum BX Fourier transformed infrared spectrophotometer. Infrared spectra of solids were obtained from Nujol mull samples and liquids samples were applied neat on sodium chloride disks. UV spectra were obtained using a HP 8425 UV/VIS instrument with quartz 1 mL cuvets. $^1H$ and $^{13}C$ NMR experiments were performed on a Bruker AMX 400 MHz instrument. Chemical shifts are reported in parts per million (ppm) relative to tetramehylsilane (TMS). Low-resolution ESI-MS mass spectra were recorded on a Finnigan LCQ DUO MS instrument using a Gilson analytic HPLC with UV/VIS detector. APCI (atmospheric chemical ionization) mass spectrometry was performed on a Finnigan TSQ 7000 Triple Quad MS instrument equipped with a HP 1090 HPLC. Purity of compounds was checked with a reversed phase Ranin SD200 analytic HPLC with PDA detector or a Waters 2690 analytic HPLC with model 996 PDA detector and both equipped with a YMC 3.5 μm C18 analytic column (20×4.6 mm, UV detection (10-90%

ACN/H₂O 0.1% TFA, 12 min, 220 nm, 1 mL/min)). The abbreviations below are defined as follows:

DMF = dimethylformamide
DMSO = dimethylsulfoxide
DCM = dichloromethane
HPLC = High pressure liquid chromatography
rt = retention time
HOBT = hydroxybenzotriazole
DCC = dicyclohexylcarbodiimide
TFA = trifluoroacetic acid
FMOC = 9-fluorenylmethoxycarbonyl
HATU = O-(7-Azabenzotriazol-1-yl)-N,N,N',N'-tetramethyluronium hexafluorophosphate
HOAT = Hydroxy-7-Azabenzotriazole
DMAP = 2-dimethylaminopyridine
DIEA = diisopropylethylamine
EtOAc = ethyl acetate
Et2O = diethyl ether

Example 1

The following example illustrates the synthesis of 6-Chloro-[1,1';4',1"]terphenyl-3-carboxylic acid (pyridin-4-ylmethyl)-amide (137).

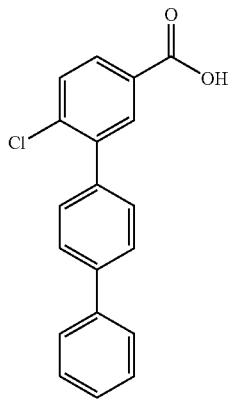

327

6-Chloro-[1,1';4',1"]terphenyl-3-carboxylic acid (327): To an oven dried 2 L round bottom flask was added 525 mL of dry DMF, 225 mL of 2.0 M solution of K₂CO₃, 16 μm of 4-biphenyl boronic acid, and 25 μm of 4-Chloro-3-iodo benzoic acid. The mixture was degassed for 25 minutes by bubbling 10 psi N₂ gas through canula needle through the reaction solution. To the degassed solution was added 1.93 μm of Pd₂dba₃ and the resultant mixture was stirred for at 65° C. After 24 hours, the solution was cooled and 300 mL of saturated Na₂S₂O₅ was added. After vigorous mixing the mixture was filtered through a coarse sintered glass filter to remove the palladium. The solution was acidified with 1N HCl which resulted in the formation of a precipitate. After one hour, the solid material was collected by filtration with a coarse sintered glass filter. The precipitate was washed with water (5×100 mL) to remove the residual solvents and 33.3 μm of a slightly yellow powder was isolated and then dried under vacuum for 12 hours. The powder was taken up in 150 mL of acetone and to it was added 45 mL of water. The resultant solution warmed until all of the solid material was dissolved. After cooling at 0° C. for 10 hours, the precipitate was collected by sintered glass filter and dried over night under vacuum to yield 25.5 gm of flat white flakes were recovered for a 93.4% yield. ¹H NMR 400 MHz DMSO-d6: $\delta_H$ 7.91-7.29 (12H, m); MS (ES⁻) m/z 308 (M+); HPLC (214 nm), rt 6.64 min, 99.0%.

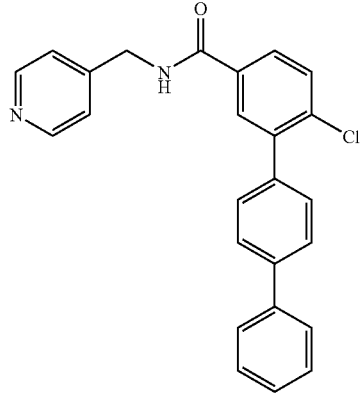

137

6-Chloro-[1,1';4',1"]terphenyl-3-carboxylic acid (pyridin-4-ylmethyl)-amide (137): To an oven dried 50 mL round bottom flask was added 20 mL of dry methylene chloride (DCM), 1.0 gm of 327, 15 mL of 2M SOCl₂, and 2 drops of dimethyl formamide (DMF). The mixture was stirred for 2 hours at room temperature. The solution was rotary evaporated to leave the neat acid chloride weighing 1.15 g (>99% yield). To this residue was added 25 mL of tetrahydrofuran (THF). Approximately 5 mL of the solution (0.8 mmol) was transferred to an oven dried 25 mL round bottom flask and to it was added 3.5 mL of diisopropyl ethyl amine, 83 μL (0.82 mmol, 1.05 g) of 4-benyl amine pyridine. The resultant solution was stirred for 3 hours then quenched by the addition of 5 mL of water and 5 mL of DCM. The product was taken up in 20 mL of DCM and washed with water (5×15 mL) and dried over Na₂SO₄. The solution was rotary evaporated to leave a yellow oil weighing 283 mg (86.5% crude yield). Approximately 5 mg of the crude product were purified by semipreparative HPLC to provide 4.1 mg of the titled compound. ¹H NMR 400 MHz DMSO-d6: $\delta_H$ 9.49 (2H, d, J=3.1 Hz), 8.71 (2H, d, J=3.1 Hz), 8.02 (1H, s), 7.88-7.28 (11H, m); 4.65 (2H, s), 3.70 (1H, br s); MS (ES⁺) m/z 399 (M+H); HPLC (214 nm), rt 4.92 min, 99.4%.

Example 2

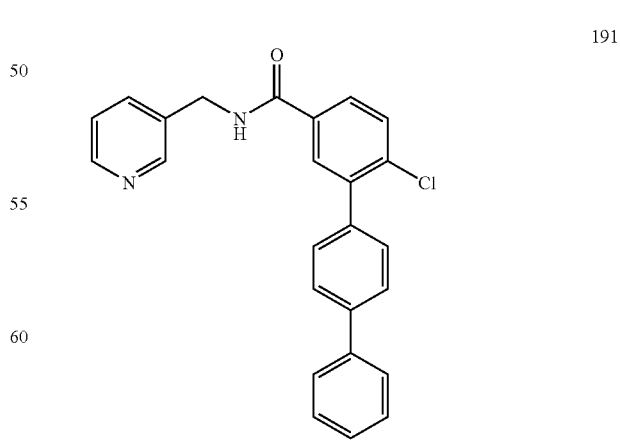

191

6-Chloro-[1,1';4',1"]terphenyl-3-carboxylic acid (pyridin-3-ylmethyl)-amide (191): ¹H NMR 400 MHz DMSO-d6: $\delta_H$ 9.22 (1H, dd, J=3.1, 3.7 Hz), 8.67 (1H, s), 8.54 (1H, d, J=3.1 Hz), 8.06 (1H, d, J=3.7 Hz), 7.88 (1H, s), 7.78-7.24 (11H, m); 4.46 (2H, s), 4.12 (1H, br s); MS (ES⁺) m/z 399 (M+H); HPLC (214 nm), rt 4.86 min, 99.8%.

Example 3

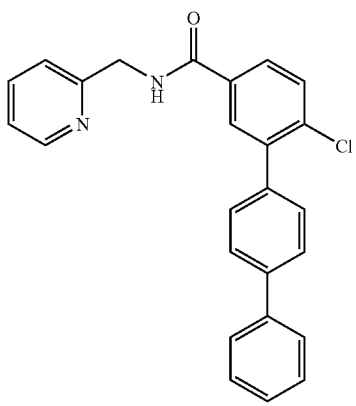

201

6-Chloro-[1,1';4',1"]terphenyl-3-carboxylic acid (pyridin-2-ylmethyl)-amide (201): ¹H NMR 400 MHz DMSO-d6: $\delta_H$ 9.32 (1H, dd, J=2.7, 3.1 Hz), 8.62 (1H, d, J=2.7 Hz), 8.09 (1H, s), 8.05-7.32 (15H, m); 4.58 (2H, s); MS (ES⁺) m/z 399 (M+H); HPLC (214 nm), rt 5.04 min, 98.3%.

Example 4

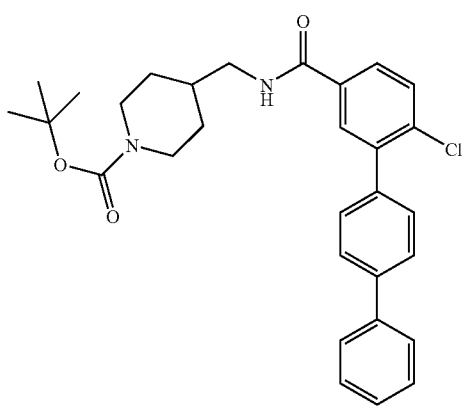

331

4-{[(6-Chloro-[1,1';4',1"]terphenyl-3-carbonyl)-amino]-methyl}-piperidine-1-carboxylic acid tert-butyl ester (331): To an oven dried 50 mL round bottom flask was added 10 mL of dry DCM and 10 mL of dry DMF, 1.0 gm of 327, and 496 mg hydroxybenzotriazole (HOBT). The mixture was stirred and to it was added DMF (5 mL) until all of the HOBT was dissolved. After one hour, 5 mL (~0.66 mmol) of the solution was transferred to an oven dried 25 mL round bottom flask. To this was added 140 mg of 4-Aminomethyl-piperidine-1-carboxylic acid tert-butyl ester (0.65 mmol), followed by 134 mg of dicyclohexyl carbodiimide (DCC) dissolved in 2 mL of DCM. The resultant solution was left stirring over 1 atm. of nitrogen for 10 hours. The reaction solution was quenched by the addition of 5 mL of water and 5 mL of DCM. The product was extracted in 20 mL of DCM and the organic extract was further washed with brine (2×15 mL) and water (3×15 mL) and dried over Na₂SO₄. The organic solution was rotary evaporated to leave a pale orange oil weighing 266 mg (87.8% crude yield). Approximately 70 mg of the crude product were purified by semipreparative HPLC to yield 50 mg of the titled compound. ¹H NMR 400 MHz DMSO-d6: $\delta_H$ 8.56-7.27 (12H, m), 3.88-0.90 (12H, m), 1.27 (9H, s); MS (ES⁺) m/z 505 (M+H), 449 (M+H, loss of —C(CH₃)₃); HPLC (214 nm), rt 7.40 min, 99.4%.

Example 5

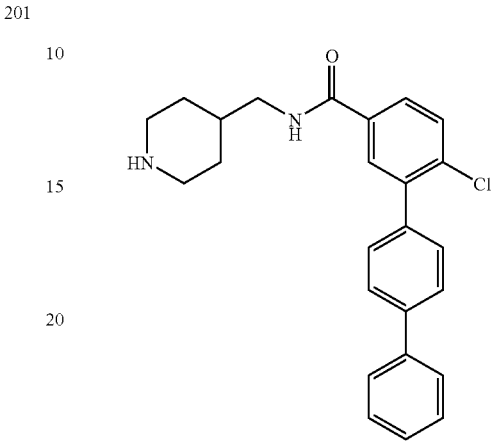

41

6-Chloro-[1,1';4',1"]terphenyl-3-carboxylic acid (piperidin-4-ylmethyl)-amide (41): To an oven dried 10 mL round bottom flask was added 5 mL of DCM, 20 mg (0.04 mmol) of 331, 1.5 mL trifluoroacetic acid (TFA), and 50 μL H₂O. The reaction solution was stirred for 1 hour and quenched with 1 mL of saturated NaHCO₃. The product was taken up in 20 mL of DCM and the organic solution further washed with water (3×15 mL) and dried over Na₂SO₄. The organic solution was rotary evaporated to provide 16.0 mg of the product as a pale tan oil (99.0% yield). ¹H NMR 400 MHz DMSO-d6: $\delta_H$ 8.71 (1H, dd, J=2.7, 3.1 Hz), 8.48 (1H, br s), 8.07 (1H, br s), 7.90 (1H, s), 7.83-7.30 (10H, m); 3.28-1.16 (11H, m); MS (ES⁺) m/z 405 (M+H); HPLC (214 nm), rt 4.94 min, 99.8%.

Example 6

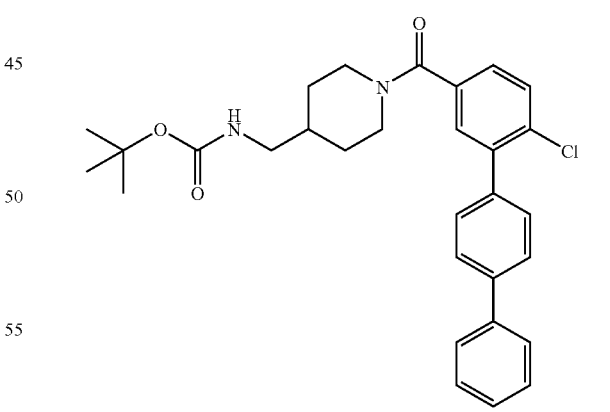

112

[1-(6-Chloro-[1,1';4',1"]terphenyl-3-carbonyl)-piperidin-4-ylmethyl]-carbamic acid tert-butyl ester (112): To an oven dried 50 mL round bottom flask was added 10 mL of dry DCM and 10 mL of dry DMF, 1.0 gm of 327, and 496 mg HOBT. The mixture was stirred and to it was added DMF (5 mL) until all of the HOBT dissolved. After one hour, 5 mL (~0.66 mmol) of the solution was transferred to an oven dried 25 mL round bottom flask. To this solution was added 140 mg of Piperidin-4-ylmethyl-carbamic acid tert-butyl ester (0.65 mmol) followed by 135 mg of dicyclohexylcarbodiimide (DCC) dissolved in 2 mL of DCM. The solution was left stirring over 1 atm. of nitrogen for 10 hours. The reaction solution was quenched by the addition of 5 mL of water and 5 mL of DCM. The product was taken up in 20 mL of DCM and washed with (2×15 mL) brine and (3×15 mL) H₂O, then dried over Na₂SO₄. The organic solution was rotary evaporated to leave 299 mg of a pale orange oil (91.1% crude yield). Approximately 70 mg of the crude product were purified by semipreparative HPLC to provide 45 mg of the product. ¹H NMR 400 MHz DMSO-d6: δ$_H$ 7.73-7.26 (12H, m), 6.82 (1H, br s), 4.39-0.91 (11H, m), 1.22 (9H, s); MS (ES⁺) m/z 505 (M+H), 449 (M+H, —C(CH₃)₃); HPLC (214 nm), rt 7.11 min, 90.0%.

Example 7

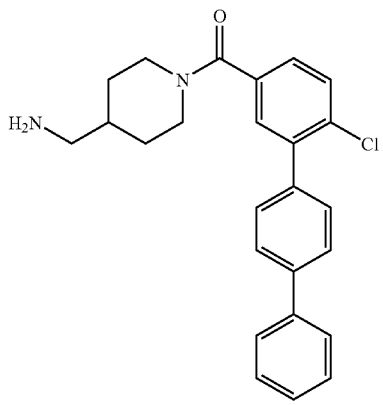

171

(4-Aminomethyl-piperidin-1-yl)-(6-chloro-[1,1';4',1"]terphenyl-3-yl)-methanone (171): To an oven dried 10 mL round bottom flask was added 5 mL of DCM, 20 mg (0.04 mmol) 120, 1.5 mL trifluoroacetic acid (TFA), and 50 μL H₂O. The solution was stirred for 1 hour and quenched with 1 mL of saturated NaHCO₃. The product was taken up in 20 mL of DCM and washed with (3×15 mL) H₂O and dried over Na₂SO₄. The organic solution was rotary evaporated to leave 15.9 mg of a pale tan oil (97.5% yield). ¹H NMR 400 MHz DMSO-d6: δ$_H$ 7.76-7.26 (12H, m), 4.43-1.02 (13H, m); MS (ES⁺) m/z 405 (M+H); HPLC (214 nm), rt 4.74 min, 99.8%.

Example 8

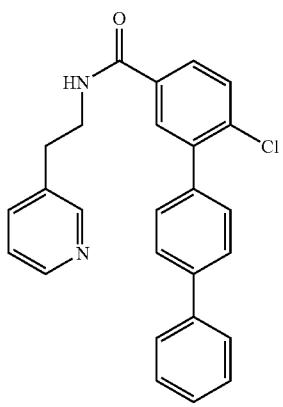

168

6-Chloro-[1,1';4',1"]terphenyl-3-carboxylic acid (2-pyridin-3-yl-ethyl)-amide (168): ¹H NMR 400 MHz DMSO-d6: δ$_H$ 8.73 (1H, s), 8.71-8.51 (2H, m), 8.17(1H, dd, J=2.8, 3.5 Hz), 7.78-7.24 (12H, m); 3.54 (2H, dd, J=4.1, 10.5 Hz), 2.96 (2H, dd, J=4.1, 10.5 Hz); MS (ES⁺) m/z 413 (M+H); HPLC (214 nm), rt 4.99 min, 99.7%.

Example 9

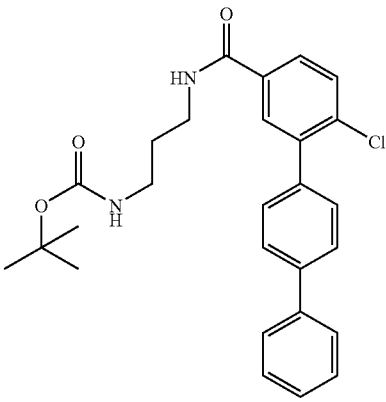

328

{3-[(6-Chloro-[1,1';4',1"]terphenyl-3-carbonyl)-amino]-propyl}-carbamic acid tert-butyl ester (328): To an oven dried 50 mL round bottom flask was added 12 mL of dry DCM, 12 mL of dry DMF, 1.2 gm of 327 and 595 mg HOBT. The mixture was stirred and DMF (5 mL) added until all of the HOBT dissolved. After one hour, 5 mL (~0.65 mmol) of the solution was transferred to an oven dried 25 mL round bottom flask. To this solution was added 100 mg of (3-Amino-propyl)-carbamic acid tert-butyl ester (0.65 mmol) followed by 1.30 g of polystyrene bound dicyclohexyl carbodiimide (PS-DCC) dissolved in 2 mL of DCM. The solution was left stirring over 1 atm. of nitrogen for 3 hours. The solution was quenched by the addition of 5 mL of water and 5 mL of DCM. The product was filtered and then dissolved in 20 mL of DCM, washed with (2×15 mL) brine, (3×15 mL) H₂O and dried over Na₂SO₄. The organic solution was rotary evaporated to leave a pale orange oil weighing 244 mg (80.8% crude yield). Approximately 60 mg of the crude product were purified by semipreparative HPLC to provide 49 mg of the product. ¹H NMR 400 MHz DMSO-d6: δ$_H$ 8.52 (1H, br s), 7.89-7.29 (12H, m), 6.69 (1H, br s), 3.15-1.45 (6H, m), 1.29 (9H, s); MS (ES⁺) m/z 465 (M+H), 365 (M+H—C(O)C(CH₃)₃); HPLC (214 nm), rt 9.54 min, 95.9%.

Example 10

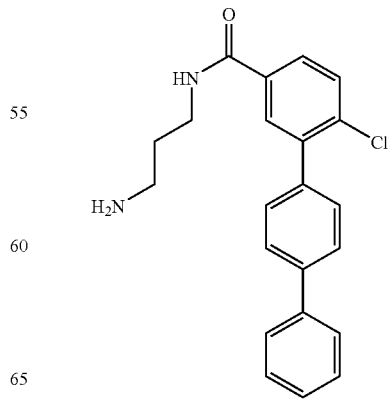

238

6-Chloro-[1,1';4',1"]terphenyl-3-carboxylic acid (3-amino-propyl)-amide (238): To an oven dried 10 mL round bottom flask was added 5 mL of DCM, 10 mg (0.022 mmol) of 328, 1.5 mL trifluoroacetic acid (TFA), and 50 μL H₂O. The solution was stirred for 1 hour and quenched with 1 mL of saturated NaHCO₃. The product was taken up in 10 mL of DCM and washed with (3×5 mL) H₂O and dried over Na₂SO₄. The organic solution was rotary evaporated to leave 5.9 mg of a pale yellow oil (73.6% yield). MS (ES⁺) m/z 365 (M+H); HPLC (214 nm), rt 7.06 min, 99.8%.

Example 11

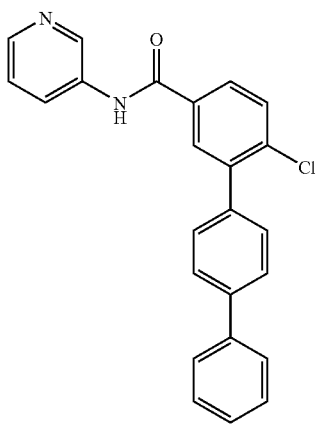

65

6-Chloro-[1,1';4',1"]terphenyl-3-carboxylic acid pyridin-3-ylamide (65): ¹H NMR 400 MHz DMSO-d6: $\delta_H$ 10.83 (1H br s), 9.16 (1H br s), 8.52 (1H br s), 8.39 (1H br s), 8.16 (1H s), 8.09 (1H J=2.5, 3.6 Hz), 7.93-7.42 (11H m); MS (ES⁺) m/z 385 (M+H); HPLC (214 nm), rt 5.19 min, 99.7%.

Example 12

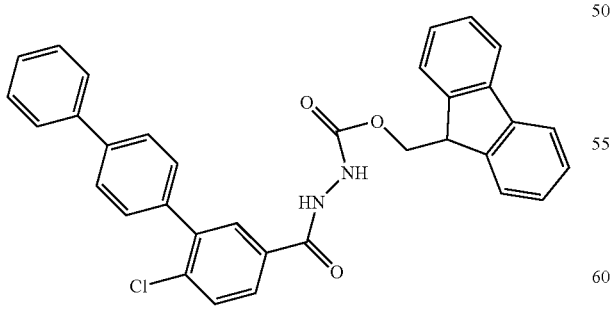

297

N'-(6-Chloro-[1,1';4',1"]terphenyl-3-carbonyl)-hydrazinecarboxylic acid 9H-fluoren-9-ylmethyl ester (297): ¹H NMR 400 MHz DMSO-d6: $\delta_H$ 10.63 (1H s), 9.42 (1H s), 7.89-7.11 (19H m); 5.46-528 (3H, m); MS (ES⁺) m/z 545 (M+H); HPLC (214 nm), rt 6.36 min, 99.7%.

Example 13

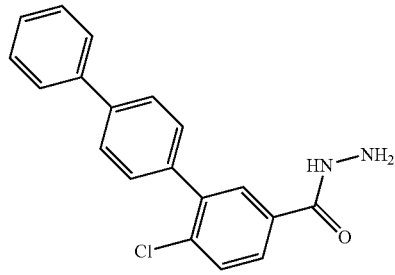

298

6-Chloro-[1,1';4',1"]terphenyl-3-carboxylic acid hydrazide (298): MS (ES⁺) m/z 323 (M+H); HPLC (214 nm), rt 7.33 min, 99.7%.

Example 14

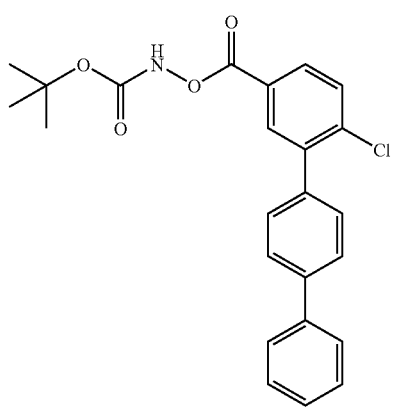

300

O'-(6-Chloro-[1,1';4',1"]terphenyl-3-carbonyl)-hydroxylaminecarboxylic acid tert-butyl ester (300): ¹H NMR 400 MHz DMSO-d6: $\delta_H$ 10.96 (1H br s), 8.01-7.32 (12H m), 1.29 (9H, s); MS (ES⁺) m/z 323 (M+H—BOC); HPLC (214 nm), rt 7.74 min, 98.2%.

Example 15

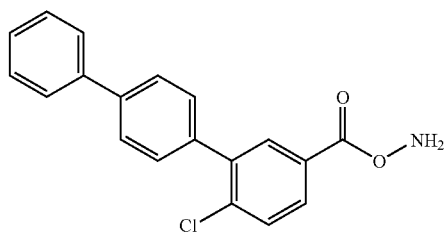

329

O'-(6-Chloro-[1,1';4',1'']terphenyl-3-carbonyl)-hydroxylamine (329): MS (ES⁺) m/z 323 (M+H); HPLC (214 nm), rt 7.05 min, 99.8%.

Example 16

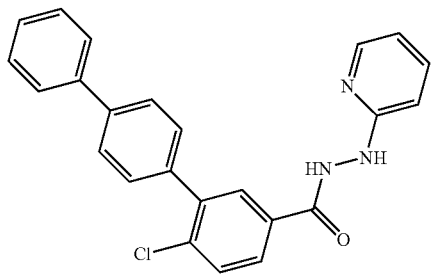

296

6-Chloro-[1,1';4',1'']terphenyl-3-carboxylic acid N'-pyridin-2-yl-hydrazide (296): ¹H NMR 400 MHz DMSO-d6: $\delta_H$ 10.89 (1H br s), 7.93-7.42 (16H m), 3.75 (1H, br s); MS (ES⁺) m/z 400 (M+H); HPLC (214 nm), rt 4.74 min, 99.8%.

Example 17

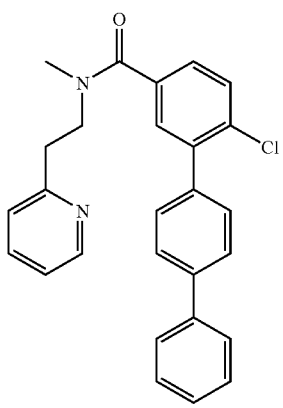

77

6-Chloro-[1,1';4',1'']terphenyl-3-carboxylic acid methyl-(2-pyridin-2-yl-ethyl)-amide (77): MS (ES⁺) m/z 427 (M+H); HPLC (214 nm), rt 5.43 min, 99.8%.

Example 18

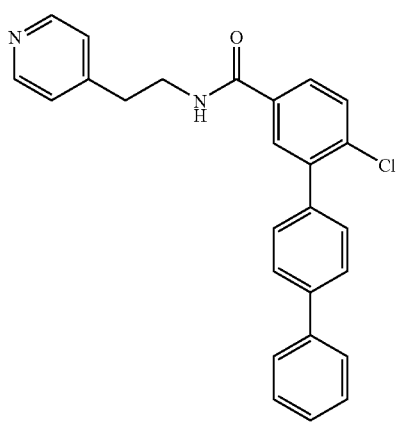

208

6-Chloro-[1,1';4',1'']terphenyl-3-carboxylic acid (2-pyridin-4-yl-ethyl)-amide (208): ¹H NMR 400 MHz DMSO-d6 $\delta_H$ 8.65-7.26 (16H, m), 6.43 (1H, br s), 3.61 (2H, dd, J=3.7, 10.8 Hz), 3.05 (2H, dd, J=3.7, 10.8 Hz); MS (ES⁺) m/z 413 (M+H); HPLC (214 nm), rt 5.01 min, 99.8%.

Example 19

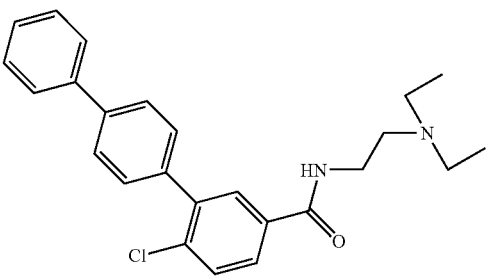

35

6-Chloro-[1,1';4',1'']terphenyl-3-carboxylic acid (2-diethylamino-ethyl)-amide (35): ¹H NMR 400 MHz DMSO-d6: $\delta_H$ 8.65-7.26 (16H, m), 6.43 (1H, br s), 3.61 (2H, dd, J=3.7, 10.8 Hz), 3.05 (2H, dd, J=3.7, 10.8 Hz), 2.82-2.69 (4H, m), 1.01-0.91 (6H, m); MS (ES⁺) m/z 407 (M+H); HPLC (214 nm), rt 5.62 min, 99.8%.

Example 20

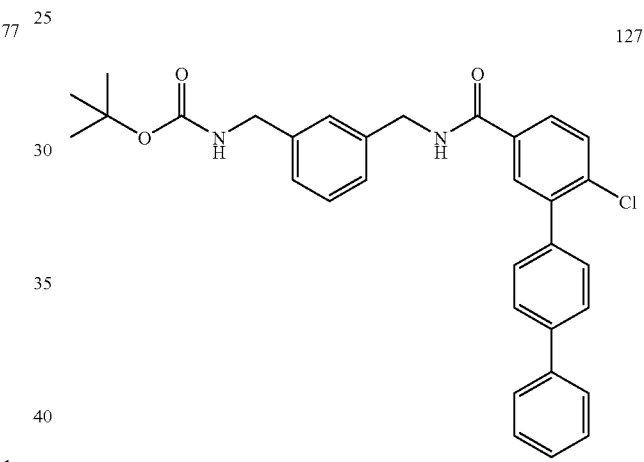

127

(3-{[(6-Chloro-[1,1';4',1'']terphenyl-3-carbonyl)-amino]-methyl}-benzyl)-carbamic acid tert-butyl ester (127): ¹H NMR 400 MHz DMSO-d6: $\delta_H$ 9.12 (1H br s), 7.92-7.04 (17H, m), 4.42 (2H, d, J=11.6 Hz), 3.98 (2H, d, J=11.2 Hz), 1.29 (9H s); MS (ES⁺) m/z 549 (M+Na); HPLC (214 nm), rt 9.53 min, 99.8%.

Example 21

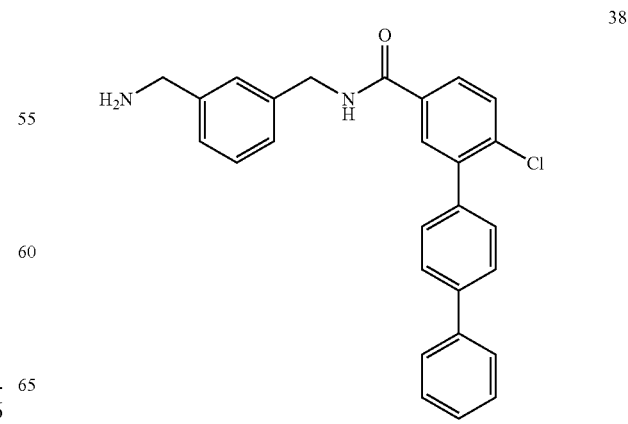

38

6-Chloro-[1,1';4',1"]terphenyl-3-carboxylic acid 3-aminomethyl-benzylamide (38): MS (ES+) m/z 427 (M+H); HPLC (214 nm), rt 5.72 min, 99.1%.

Example 22

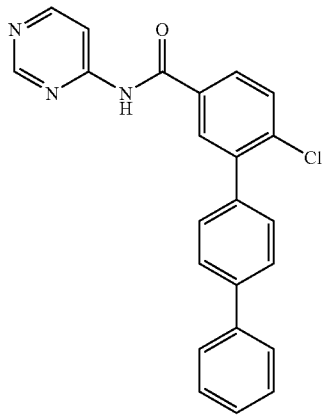

6-Chloro-[1,1';4',1"]terphenyl-3-carboxylic acid pyrimidin-4-ylamide (37): $^1$H NMR 400 MHz DMSO-d6: $\delta_H$ 8.88-7.26 (16H, m); MS (ES+) m/z 386 (M+H); HPLC (214 nm), rt 6.58 min, 99.8%.

Example 23

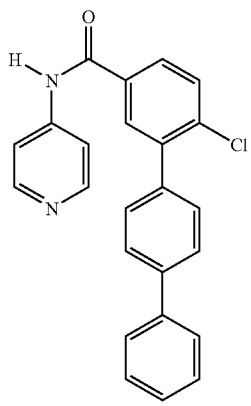

6-Chloro-[1,1';4',1"]terphenyl-3-carboxylic acid pyridin-4-ylamide (124): $^1$H NMR 400 MHz DMSO-d6: $\delta_H$ 8.51 (1H, br s), 8.65-6.78 (17H, m); MS (ES+) m/z 385 (M+H); HPLC (214 nm), rt 5.78 min, 99.7%.

Example 24

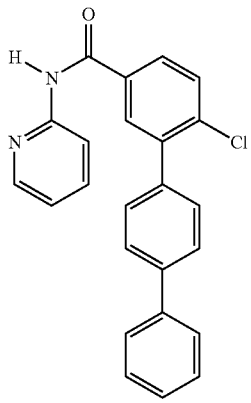

6-Chloro-[1,1';4',1"]terphenyl-3-carboxylic acid pyridin-2-ylamide (156): MS (ES+) m/z 385 (M+H); HPLC (214 nm), rt 6.27 min, 99.3%.

Example 25

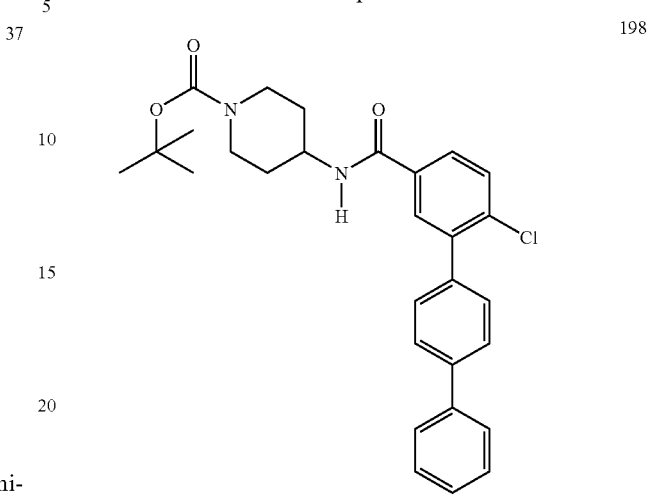

4-[(6-Chloro-[1,1';4',1"]terphenyl-3-carbonyl)-amino]-piperidine-1-carboxylic acid tert-butyl ester (198): MS (ES+) m/z 491 (M+H); HPLC (214 nm), rt 7.69 min, 92.5%.

Example 26

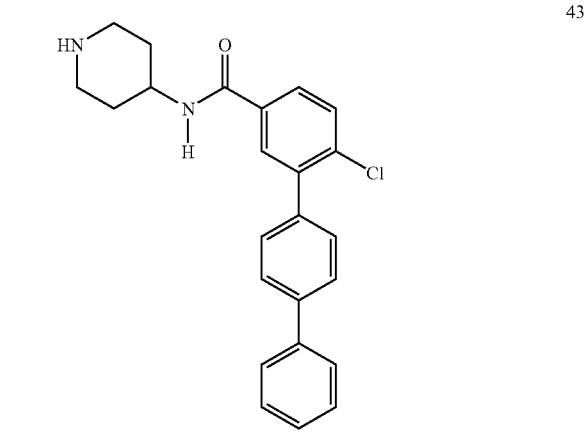

6-Chloro-[1,1';4',1"]terphenyl-3-carboxylic acid piperidin-4-ylamide (43): MS (ES+) m/z 391 (M+H); HPLC (214 nm), rt 5.42 min, 99.8%.

Example 27

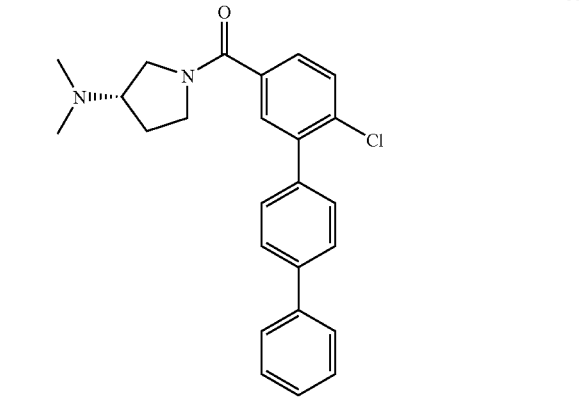

(6-Chloro-[1,1';4',1"]terphenyl-3-yl)-(3-dimethylamino-pyrrolidin-1-yl)-methanone (59): MS (ES+) m/z 405 (M+H); HPLC (214 nm), rt 5.11 min, 99.8%.

Example 28

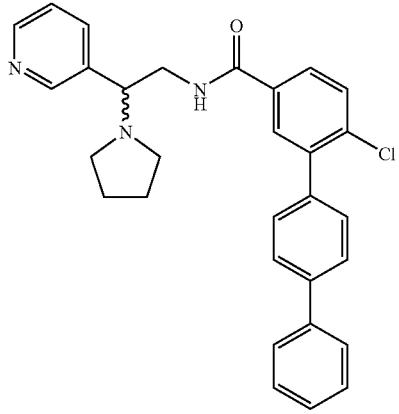

6-Chloro-[1,1';4',1"]terphenyl-3-carboxylic acid (2-pyridin-3-yl-2-pyrrolidin-1-yl-ethyl)-amide (32): MS (ES+) m/z 482 (M+H); HPLC (214 nm), rt 5.17 min, 98.1%.

Example 29

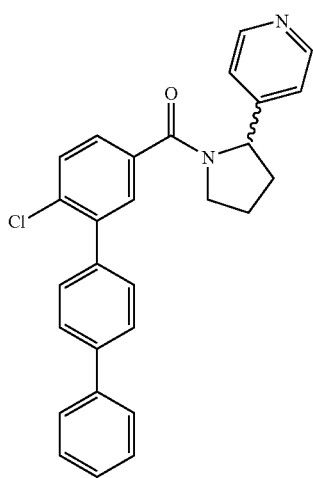

(6-Chloro-[1,1';4',1"]terphenyl-3-yl)-(2-pyridin-4-yl-pyrrolidin-1-yl)-methanone (189): MS (ES+) m/z 439 (M+H); HPLC (214 nm), rt 5.53 min, 99.8%.

Example 30

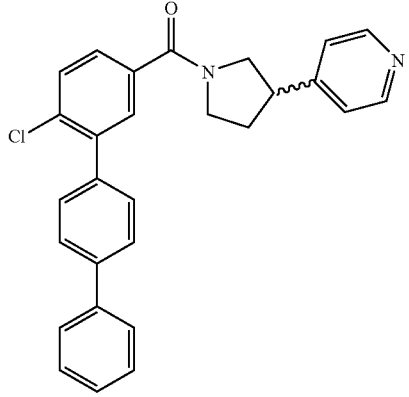

(6-Chloro-[1,1';4',1"]terphenyl-3-yl)-(3-pyridin-4-yl-pyrrolidin-1-yl)-methanone (136): MS (ES+) m/z 439 (M+H); HPLC (214 nm), rt 5.22 min, 99.3%.

Example 31

The following example provides the resin-based synthesis of a compound of the present invention: 2-[(6"-Chloro-[1,1';4',1"]terphenyl-3"-carbonyl)-amino]-indan-2-carboxylic acid (320)

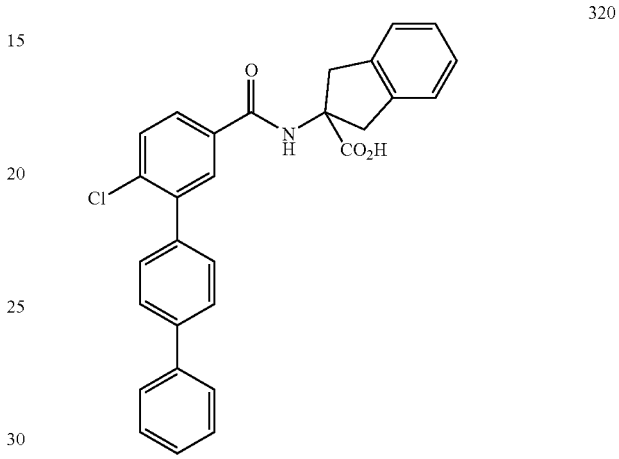

2-[(6"-Chloro-[1,1';4',1"]terphenyl-3"-carbonyl)-amino]-indan-2-carboxylic acid (320): To a 25 mL sterile centrifuge tube was added 10 mL of DCM. To this was added 1.0 g of Irori Wang resin (1.36 mmol/g loading) and 1.62 g of 2-(9H-Fluoren-9-ylmethoxycarbonylamino)-indan-2-carboxylic acid, 803 µL DCC, 597 mg HOBT, and 2 mg of dimethylaminopyridine (DMAP). The solution was capped and gentle agitated for 20 hours. A small sample of the resin (10.8 mg) was washed (2×DMF, 2×DCM, 2×Et$_2$O) and dried in a vacuum for 30 minutes. To this resin was added 1 mL of 30% piperidine in DMF for 30 minutes to remove the FMOC protecting group. 1 mL of DMF was added and four 100 µL samples were analyzed by UV to determine the FMOC content. The loading was determined to be 0.369 mmol/g (42% of theoretical). The remaining resin was added to 20 mL of 30% piperdine/DMF solution for one hour, washed (2×DMF, 2×DCM, 2×Et$_2$O) and dried under vacuum for 12 hours. To a 25 mL sterile centrifuge tube was added 36 mL of DCM. To this was added the 1 g of indene loaded resin, 1.15 g of 4-Chloro-3-iodo benzoic acid, 2.09 g PyBOP, and 2.13 mL DIEA. After 2 hours the resin was rinsed and a bromophenyl blue solution added to 3 mg of beads. Primary amine was detected and the coupling reaction was repeated using 20 mL of N-methylproline (NMP), 1 g of indene loaded resin, 1.2 g 4-Chloro-3-Iodo benzoic acid, 1.6 g HATU, 0.56 g HOAT, and 2.1 mL of DIEA. After 15 hours of agitation, a second bromophenyl blue test was performed and no amine detected.

In a separate 25 mL pear shaped flask was added 10 mL of acetone, 1 g of Iodo phenyl-indene loaded resin, 1.98 g 4-Biphenyl boronic acid, 0.25 g Pd$_2$dba$_3$, and 1 mL of 2M K$_2$CO$_3$. The resultant mixture was heated to 65° C. for 22 hours. The resin was filtered and washed (2×Na$_2$SO$_5$, 2×H$_2$O, 2×DMF, 2×CH₃OH, 2×DCM, 1×EtOAc, 2×Et₂O) and dried in a vacuum for 10 hours. Cleavage of the product from the resin was effected by the addition of 5 mL TFA, 0.10 ml, H₂O, 0.10 mL DCM in a 15 mL enclosed fritted funnel for 20 minutes. The filtrate was removed, the resin washed (3×15 mL DCM), and all fractions collected. Rotary evaporation of the filtrate left 156 mg of a crude product as an oil (24% yield). 16 mg of the crude oil was purified by semipreparative HPLC to obtain 10.2 mg pure product. ¹H NMR 400 MHz DMSO-d6: $\delta_H$ 12.5 (1H br s), 8.93 (1H s), 7.94-7.10 (16H, m), 4.61 (2H, d, J=13.5 Hz), 3.38 (2H, d, J=13.6 Hz); MS (ES⁻) m/z 468 (M−H); HPLC (214 nm), rt 6.90 min, 99.4%.

Example 32

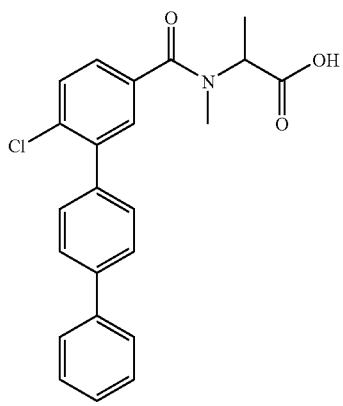

2-[(6"-Chloro-[1,1';4',1"]terphenyl-3"-carbonyl)-methyl-amino]-propionic acid (321): MS (ES⁻) m/z 392 (M−H); HPLC (214 nm), rt 6.22 min, 98.9%.

Example 33

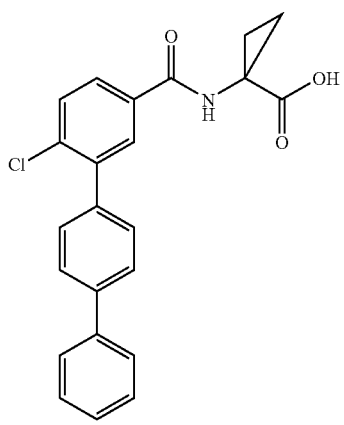

1-[(6"-Chloro-[1,1';4',1"]terphenyl-3"-carbonyl)-amino]-cyclopropanecarboxylic acid (322): ¹H NMR 400 MHz DMSO-d6: $\delta_H$ 8.65 (1H s), 7.98-7.10 (12H, m), 2.55 (2H, s), 1.44 (2H s); MS (ES⁻) m/z 390 (M−H); HPLC (214 nm), rt 6.05 min, 99.6%.

Example 34

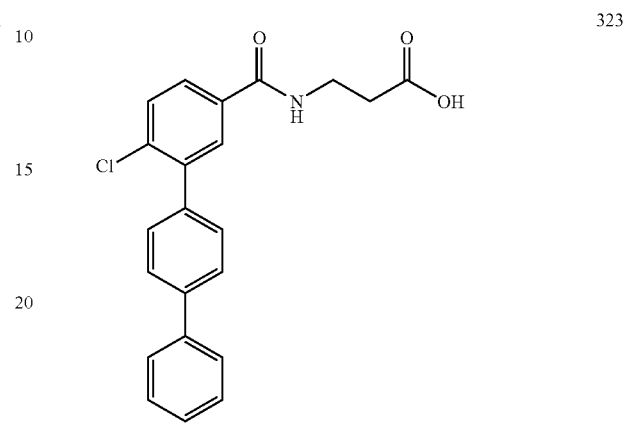

3-[(6"-Chloro-[1,1';4',1"]terphenyl-3"-carbonyl)-amino]-propionic acid (323): MS (ES⁻) m/z 378 (M−H); HPLC (214 nm), rt 5.67 min, 99.7%.

Example 35

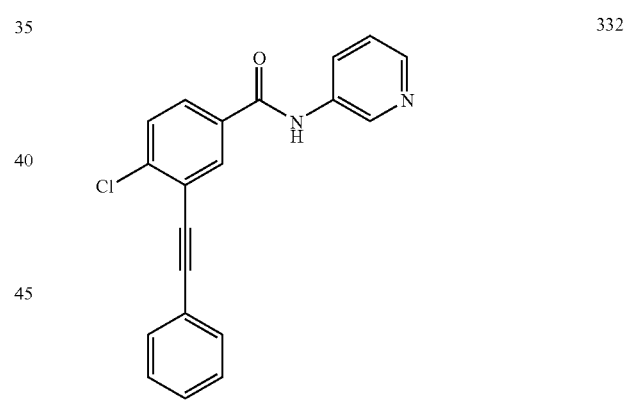

4-Chloro-3-phenylethynyl-N-pyridin-3-yl-benzamide (332): To a 50 mL oven dried flask was added 20 mL of dry DCM, 1.0 g of 330 and 2 drops of DMF. To the resultant solution was slowly was added 2 mL of 2M oxalylchloride. The reaction was stirred under nitrogen for 1 hour. The solution was rotary evaporated to leave the crude acid chloride product. After addition of 28 mL of tetrahydrofuran (THF), 7 mL of the acid chloride was added to an oven dried 25 mL round bottom flask with 95 mg of 3-aminopyridine and 0.87 mL of DIEA. The solution was stirred for 1.5 hours. To the reaction solution were added 5 mL of water and 5 mL of EtOAc. The organic extract was washed (3×brine, 3×H₂O) then dried over Na₂SO₄ for 1 hour, filtered and concentrated by rotary evaporation. Over night vacuum drying provided in 253 mg of a light tan oil for an 80.1% yield. MS (ES⁺) m/z 317 (M+H); HPLC (214 nm), rt 5.37 min, 99.1%.

Example 36

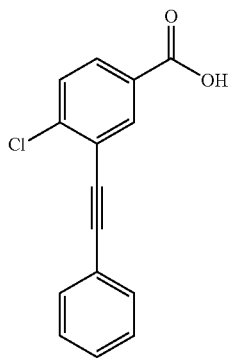

4-Chloro-3-phenylethynyl-benzoic acid (330): To a 1 L oven dried flask was added 225 mL of dry DMF, 9 mL of phenyl acetylene, 77 mL of DIEA, and 25 gm of 4-Chloro-3-iodo benzoic acid. The mixture was degassed by bubbling 10 psi $N_2$ gas through a canula needle for 25 minutes. 2.02 gm of $Pd_2dba_3$ and 338 mg of $(o\text{-Tolyl})_3P$ were added and the resulting mixture stirred for 69 hours a 65° C. The solution was cooled and 500 mL of saturated $Na_2S_2O_5$ was added and shaken vigorously in a separatory funnel. The water portion was removed and a gelatinous film remained in the flask after pouring off of the organic layer. The organic layer was filtered through coarse filter paper into a 4 L Erlenmeyer flask to remove the remaining polymeric material and left to stand for 8 hours. No additional precipitation was observed. To the organic solution was added one liter of water followed by 500 mL of sodium metabisulfite. Precipitation of the product was observed and the solution cooled in an ice bath for an additional 2 hours. The precipitated solids were collected by filteration in a funnel and washed (3×500 mL) with ice water. The solids were dried over night under vacuum. 58.7 gm of large opaque crystals were recovered. The crystals were dissolved in 1 L of ethyl acetate (EtOAc) in a separatory funnel, washed (3×brine, 3×$H_2O$), and dried with $Na_2SO_4$ for 1 hour. The solution was filtered and the solvent removed by rotary evaporatoration. Over night drying under vacuum resulted provided 18.57 g of product as plate like crystals (81.7% yield). $^1$H NMR 400 MHz DMSO-d6: $\delta_H$ 11.52 (1H s), 7.88-7.20 (8H m); MS (ES$^-$) m/z 256 (M–H); HPLC (214 nm), rt 4.94 min, 99.8%.

Example 37

324

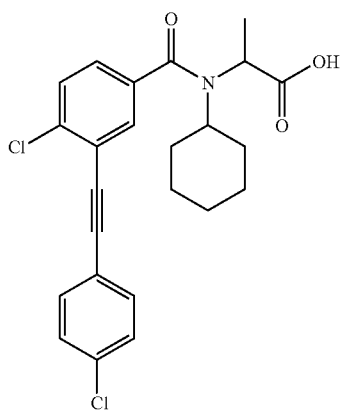

2-{[4-Chloro-3-(4-chloro-phenylethynyl)-benzoyl]-cyclohexyl-amino}-propionic acid (324): MS (ES$^+$) m/z 444 (M+H); HPLC (214 nm), rt 7.90 min, 94.6%.

Example 38

325

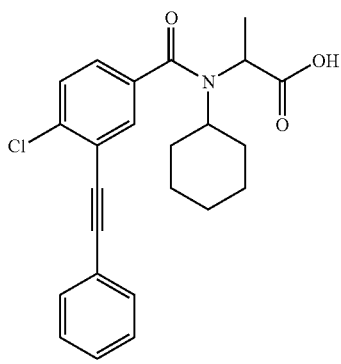

2-[(4-Chloro-3-phenylethynyl-benzoyl)-cyclohexyl-amino]-propionic acid (325): $^1$H NMR 400 MHz DMSO-d6: $\delta_H$ 7.99 (1H s), 7.94-7.22 (7H, m); 6.45 (1H, d, J=1.5 Hz), 3.79-3.72 (2H, m), 1.95-0.91 (13H m); MS (ES$^+$) m/z 410 (M+H); HPLC (214 nm), rt 7.92 min, 98.5%.

Example 39

326

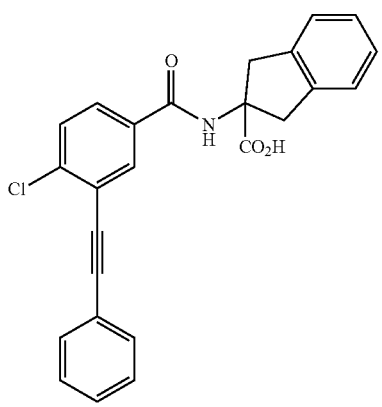

2-(4-Chloro-3-phenylethynyl-benzoylamino)-indan-2-carboxylic acid (326): MS (ES$^+$) m/z 416 (M+H); HPLC (214 nm), rt 7.92 min 98.5%.

Example 40

The following example illustrates the synthesis of 6-Chloro-4'-dimethylsulfamoyl-biphenyl-3-carboxylic acid (6-methoxy-pyridin-3-yl)-amide (3).

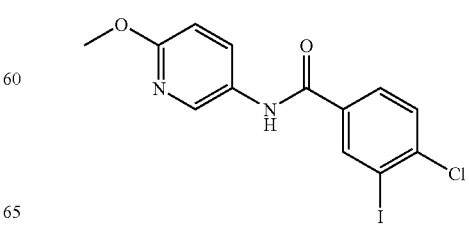

6-Chloro-1-Iodophenyl-3-carboxylic acid (6-methoxy-pyridin-3-yl)-amide: To an oven dried 50 mL round bottom flask was added 20 mL of dry methylene chloride (DCM), 2.35 g of 4-Chloro-3-iodo benzoic acid, and 3 drops of dimethyl formamide (DMF) to this solution was added drop wise by addition funnel 7.0 mL of 2.0M oxalyl chloride ($CO_2Cl_2$). The resultant mixture was stirred for 6 hours at room temperature. The solution was rotary evaporated to leave the neat acid chloride weighing 2.41 g (>98% yield). To this residue was added 20 mL of acetonitrile (ACN), 1.33 mL of diisopropyl ethyl amine, 1.25 mL (8.4 mmol, 0.45 g) of 2-Methoxy-5-amino pyridine. The resultant solution was stirred for 15 hours and heated to reflux then quenched by the addition of 10 mL of brine and 10 mL of EtOAc. The product was taken up in 20 mL of EtOAc and washed with brine (1×15 mL), 1 M NaOH (2×25 mL), water (1×15 mL) and dried over $MgSO_4$. The solution was rotary evaporated to leave a purplish waxy solid weighing 2.84 g (91.2% crude yield). The solids were dissolved into 25 mL of warm methanol (MeOH) and left sealed for 24 hours. White-violet powder was recovered. This process repeated again to yield 1.96 g (63.0%) fluffy light violet solid. TLC was single spot rf 0.58 in 1:1 Hexane/Ethyl Acetate. $^1$H NMR 400 MHz DMSO-d6: $\delta_H$ 9.01 (1H, br s), 8.24-6.77 (7H, m), 3.65 (3H, s); MS (ES$^+$) m/z 389 (M+H); HPLC (214 nm), rt 4.22 min, 99.4%.

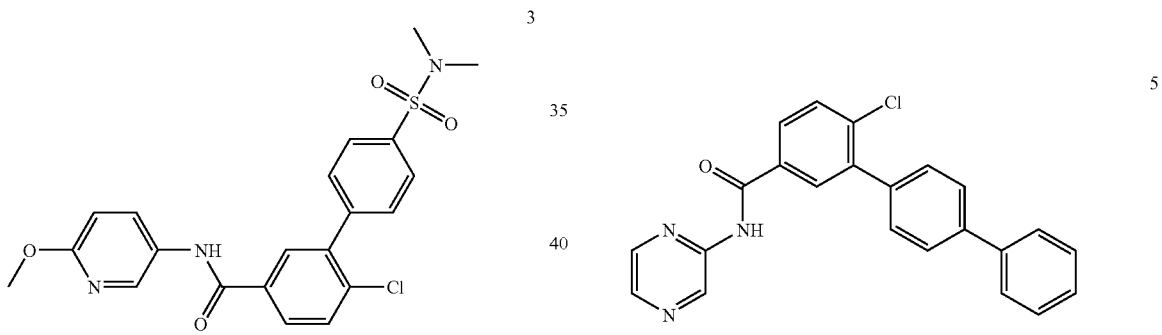

3

6-Chloro-4'-dimethylsulfamoyl-biphenyl-3-carboxylic acid (6-methoxy-pyridin-3-yl)-amide (3): To an oven dried 25 mL round bottom flask was added 5 mL of anhydrous 1,2-dimethoxyethane (DME), 0.388 g of 6-Chloro-1-iodophenyl-3-carboxylic acid (6-methoxy-pyridin-3-yl)-amide, 0.458 g of N,N-Dimethyl 4-boronobenzenesulfonamide, 21 mg tris(dibenzylideneacetone)dipalladium (0) chloroform adduct, and 1.5 mL of 2.0 M sodium carbonate. The mixture was stirred at reflux for 28 hours and quenched by the addition of 10 mL of saturated sodium metabisulfite and 10 mL of Ethyl Acetate (EtOAc). The mixture was taken up in 10 mL of EtOAc and washed with sodium metabisulfite (1×15 mL), 1 M NaOH (2×25 mL), water (1×15 mL) and dried over $MgSO_4$. The solution was rotary evaporated to leave a light tan powdery solid weighing 0.52 g (>100% crude yield). The solids were dissolved into 7 mL of warm methanol (MeOH) and left sealed for 24 hours. White needles were recovered. This crystallization process was repeated again to yield 0.300 g (67.3%) white shiny crystals. TLC was single spot rf 0.41 in 1:1 Hexane/Ethyl Acetate. $^1$H NMR 400 MHz DCM-d2: $\delta_H$ 8.82-6.97 (11H, m), 4.02 (3H, s), 2.71 (6H, s); MS (ES$^+$) m/z 447 (M+H); HPLC (214 nm), rt 5.34 min, 99.3%.

Example 41

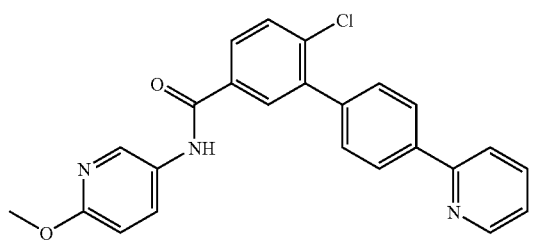

1

6-Chloro-4'-pyridin-2-yl-biphenyl-3-carboxylic acid (6-methoxy-pyridin-3-yl)-amide (1): $^1$H NMR 400 MHz DMSO-d6: $\delta_H$ 8.84 (1H, br s), 8.14-6.74 (14H, m), 3.69 (3H, s); MS (ES$^+$) m/z 417 (M+H); HPLC (214 nm), rt 6.03 min, 99.0%.

Example 42

5

6"-Chloro-[1,1';4',1"]terphenyl-3"-carboxylic acid pyrazin-2-ylamide (5): $^1$H NMR 400 MHz CDCl: $\delta_H$ 9.01 (1H, br s), 8.21-7.20 (15H, m); MS (ES$^+$) m/z 387 (M+H); HPLC (214 nm), rt 6.41 min, 93.7%.

Example 43

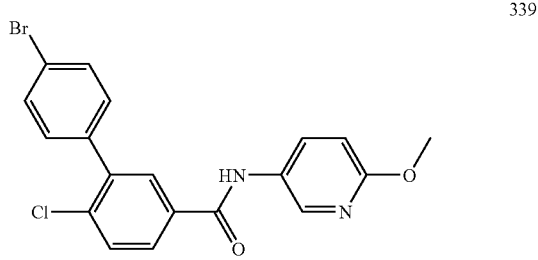

339

6-Chloro-4'-bromo-biphenyl-3-carboxylic acid (6-methoxy-pyridin-3-yl)-amide (339): $^1$H NMR 400 MHz DMSO-d6: δ$_H$ 10.38 (1H, br s), 8.49-6.84 (10H, m), 3.71 (3H, s); MS (ES$^+$) m/z 419 (M+H); HPLC (214 nm), rt 6.14 min, 99.4%.

Example 44

The compounds listed in Table II were prepared using the procedures outlined in the above Examples. These compounds were tested in the cell proliferation assay (MCF-7 cell line) as described above and exhibited the following levels of activity: +, IC50>10 μM, ++, IC50<10 μM and >1 μM, +++, IC50<1 μM.

TABLE II

| Compound | Activity |
| --- | --- |
|  | +++ |
|  | +++ |
|  | +++ |

TABLE II-continued

| Compound | Activity |
| --- | --- |
|  | +++ |
|  | +++ |
|  | +++ |
|  | ++ |

TABLE II-continued

| Compound | Activity |
|---|---|
| (structure: 4-chloro-3-(biphenyl-4-yl)-N-(6-(vinylsulfinyl)pyridin-3-yl)benzamide) | ++ |
| (structure: 4-chloro-3-(biphenyl-4-yl)-N-(5-(trifluoromethyl)-1,3,4-thiadiazol-2-yl)benzamide) | ++ |
| (structure: N-(4,5-dihydrothiazol-2-yl)-4-chloro-3-(4'-(methylsulfonyl)biphenyl-4-yl)benzamide) | ++ |
| (structure: tetrahydroisoquinoline derivative with histamine-ethyl amide and 4-chloro-3-(biphenyl-4-yl)benzoyl group) | + |
| (structure: N-(2-chloropyridin-3-yl)-4-chloro-3-(biphenyl-4-yl)benzamide) | + |
| (structure: tert-butyl (4-chloro-3-(biphenyl-4-yl)benzoyloxy)carbamate) | + |

TABLE II-continued

| Compound | Activity |
|---|---|
| 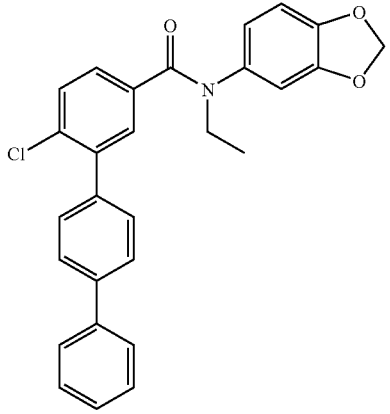 | + |

Example 45

The compounds listed in Table III were prepared using the procedures outlined in the above Examples. These compounds were tested in cell proliferation assays and exhibited the following levels of activity: +, GI50 or IC50>25 µM; ++, GI50 or IC50<25 µM and >1 µM; +++, GI50 or IC50≦1 µM.

TABLE III

| | Panel/Cell Line | | | | | |
|---|---|---|---|---|---|---|
| Compound No. | Leukemia HL-60 | Leukemia HL60-MX1 (MDR) | NSC Lung Cancer NCI-H460 | SC Lung Cancer H69-AR (MDR) | Colon Cancer HCT-15 | CNS Cancer SF-268 |
| 8 | +++ | ++ | +++ | +++ | +++ | +++ |
| 33 | ++ |  |  | ++ | + | ++ |
| 43 | ++ | +++ | ++ | +++ | ++ | ++ |
| 37 | ++ | +++ | ++ | +++ | ++ | ++ |
| 5 | +++ | +++ | +++ | +++ | +++ | +++ |
| 58 | ++ | ++ | ++ | +++ | ++ | ++ |
| 52 | ++ | ++ | ++ | ++ | ++ | ++ |
| 17 |  | +++ | +++ |  | +++ | +++ |
| 40 |  | +++ | +++ | +++ | +++ | +++ |
| 6 |  | +++ | +++ | +++ | +++ | ++ |
| 13 |  |  | +++ |  | +++ | ++ |
| 303 |  |  | +++ |  | +++ | +++ |
| 338 |  |  | +++ |  | +++ | +++ |
| 20 |  |  | ++ |  | + | ++ |
| 26 |  |  | ++ |  | ++ | ++ |
| 36 |  |  | +++ |  |  |  |
| 32 |  | ++ |  | +++ |  | ++ |
| 68 |  |  | +++ |  |  |  |
| 236 |  |  |  |  |  | + |
| 223 |  |  |  |  |  | + |

Example 46

The compounds listed in Table IV were prepared using the procedures outlined in the above Examples. These compounds were tested in cell proliferation assays and exhibited the following levels of activity: +, GI50 or IC50>25 µM; ++, GI50 or IC50<25 µM and >1 µM; +++, GI50 or IC50≦1 µM.

TABLE IV

| | Panel/Cell Line | | | | | | |
|---|---|---|---|---|---|---|---|
| Compound No. | Melanoma SK-MEL-2 | Ovarian Cancer OVCAR-3 | Uterine MES-SA/Dx5 | Renal Cancer UO-31 | Prostate Cancer PC-3 | Breast Cancer MCF-7 | Breast Cancer NCI-ADR |
| 8 | ++ | +++ | +++ | ++ | +++ | + | +++ |
| 33 | ++ | ++ |  | ++ | ++ | ++ |  |
| 43 | ++ | ++ | +++ | ++ | ++ | ++ | +++ |
| 37 | + | + | +++ | ++ | ++ | ++ | +++ |
| 5 | ++ | +++ | +++ | +++ | +++ | +++ |  |
| 58 | ++ | ++ | +++ | ++ | ++ | ++ | +++ |
| 52 | ++ | ++ | +++ | ++ | ++ | ++ | ++ |
| 17 | +++ | +++ | +++ | +++ | +++ | +++ | +++ |
| 40 | + | +++ | +++ |  | +++ | +++ |  |
| 6 | ++ | +++ | +++ | ++ | +++ | +++ | +++ |
| 13 | ++ | +++ |  | ++ | +++ | +++ |  |
| 303 | + | +++ |  | ++ | +++ | +++ |  |
| 338 | ++ | +++ |  | ++ | +++ | +++ |  |
| 20 | + | ++ |  | ++ | ++ | +++ |  |
| 26 | ++ | ++ |  | ++ | ++ | ++ |  |
| 36 |  |  | +++ |  |  | +++ | +++ |
| 32 |  |  | +++ |  |  | +++ | ++ |
| 68 |  |  |  |  |  | +++ |  |
| 236 |  |  |  |  |  | + |  |
| 223 |  |  |  |  |  | + |  |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teaching of this invention that certain changes and modifications may be made thereto without departing form the spirit or scope of the appended claims.

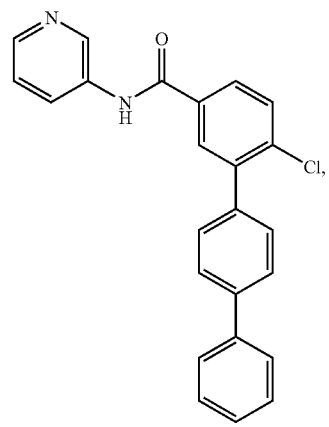

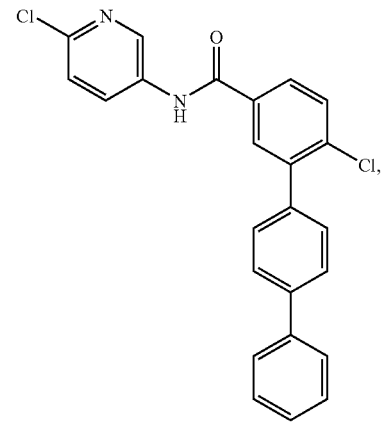

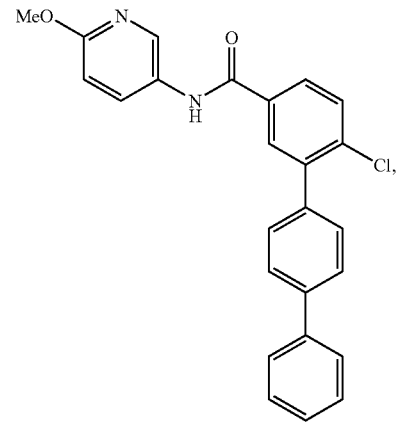

71
-continued
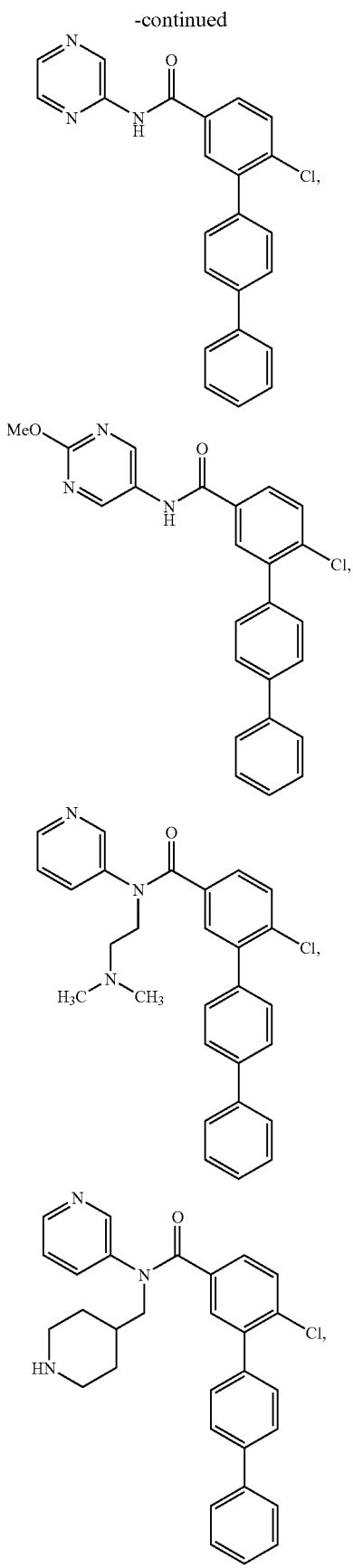
72
-continued
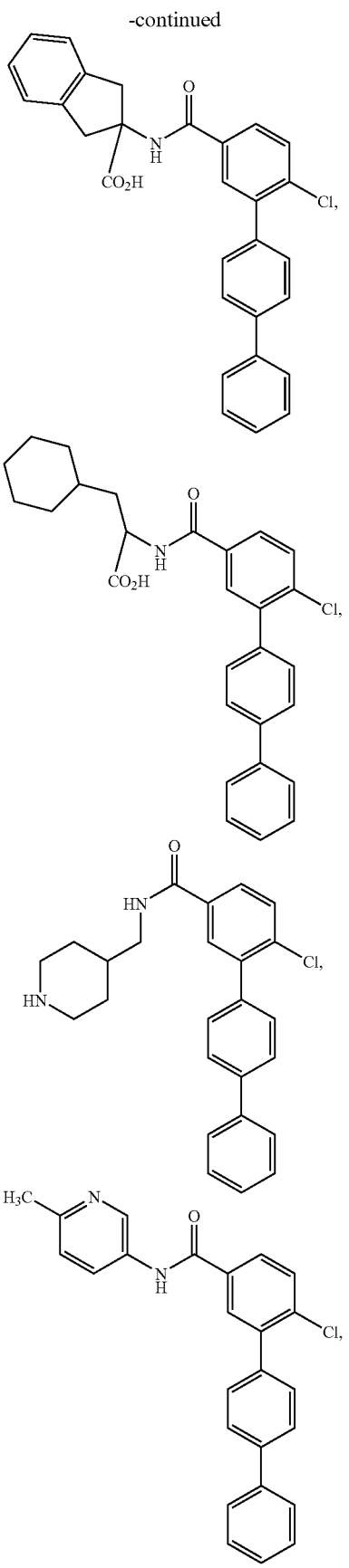

-continued
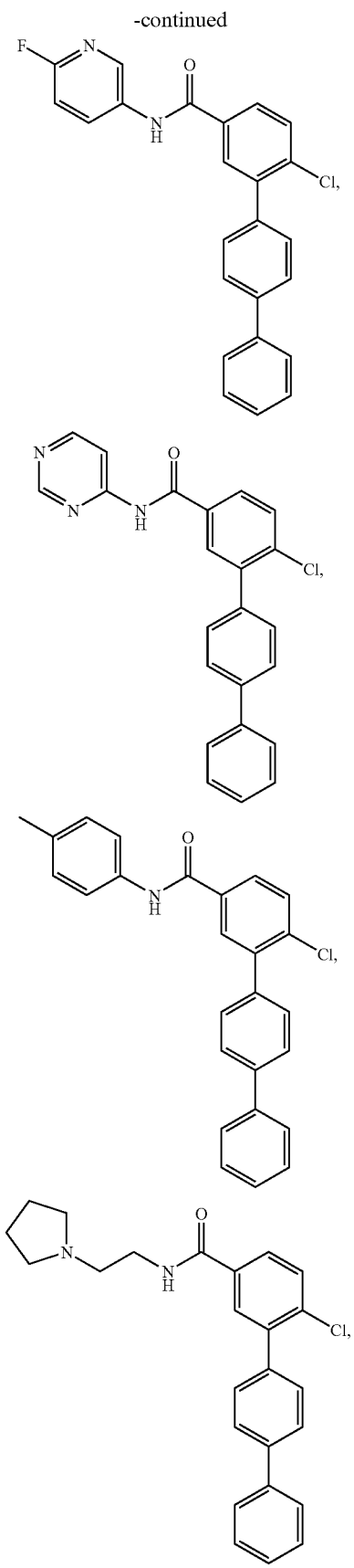
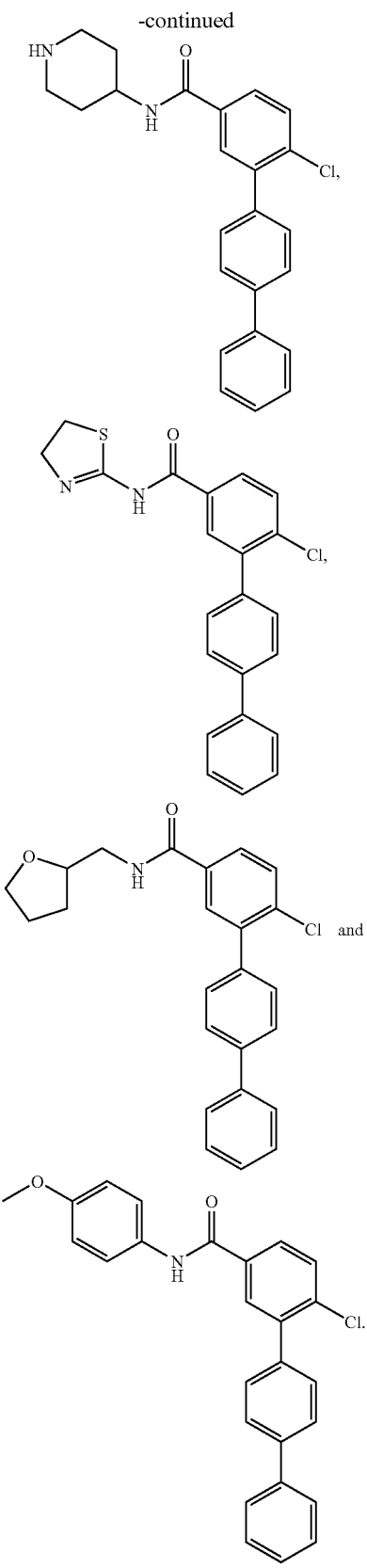

What is claimed is:

1. A compound of formula

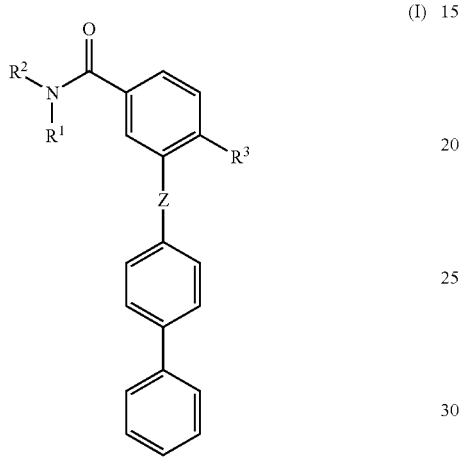

(I)

or a pharmaceutically acceptable salt thereof,
wherein $R^1$ is a member selected from the group consisting of hydrogen, $(C_1-C_8)$alkyl, $(C_1-C_8)$heteroalkyl, $(C_3-C_8)$ heterocycloalkyl$(C_1-C_8)$alkyl and aryl$(C_1-C_8)$alkyl;
$R^2$ is a member selected from the group consisting of

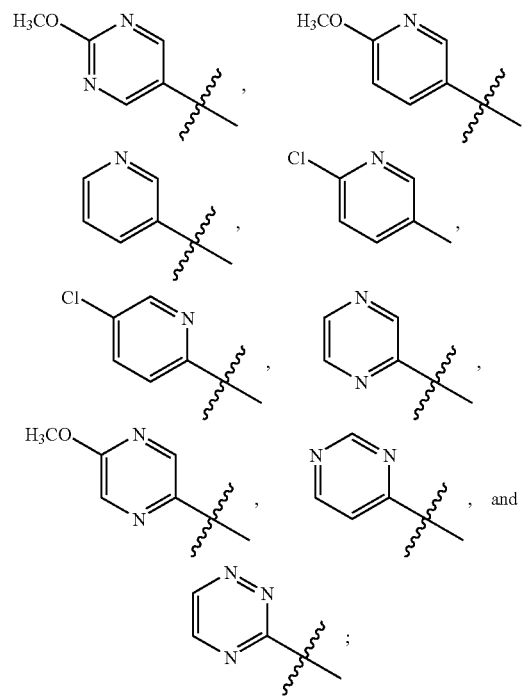

Z is a bond; and
$R^3$ is a member selected from the group consisting of hydrogen, halogen, alkyl, alkoxy, hydroxy, halo$(C_1-C_6)$ alkyl, heteroalkyl, —$NO_2$, —CN, —$CH_2CN$, —$SR^9$, —O—$S(O)R^9$, —$S(O)_2R^9$, and —$S(O)R^9$, wherein $R^9$ is a member selected from the group consisting of $(C_1-C_4)$alkyl, amino and alkylamino.

2. A compound of formula

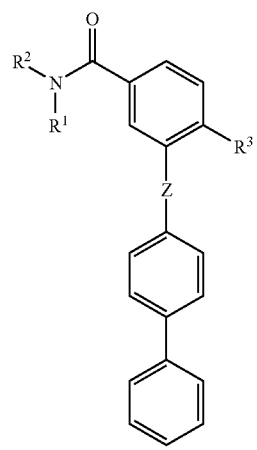

(I)

or a pharmaceutically acceptable salt thereof,
wherein $R^1$ is a member selected from the group consisting of hydrogen, $(C_1-C_8)$alkyl, $(C_1-C_8)$heteroalkyl, $(C_3-C_8)$ heterocycloalkyl$(C_1-C_8)$alkyl and aryl$(C_1-C_8)$alkyl;
$R^2$ has the formula:

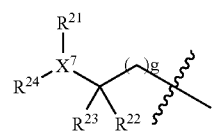

(II)

wherein
$X^7$ is N, O, or S and when $X^7$ is S or O, either $R^{21}$ or $R^{24}$ is absent;
g is an integer from 1-6;
$R^{21}$, $R^{22}$, $R^{23}$ and $R^{24}$ are each independently a member selected from the group consisting of hydrogen, halogen, halo$(C_1-C_6)$alkyl, $(C_1-C_6)$alkyl, $(C_3-C_6)$cycloalkyl, aryl, heteroaryl, aryl$(C_1-C_6)$alkyl and —C$(O)_2R^{25}$; wherein $R^{25}$ is hydrogen;
alternatively, when $X^7$ is N then $R^{21}$ and $R^{24}$ taken together with $X^7$ join to form a 4- to 7-membered ring containing 0-3 heteroatoms, wherein said 4- to 7-membered ring is optionally substituted with 1-3 substituents selected from the group consisting of $(C_1-C_6)$alkyl, $(C_1-C_6)$acyl, aryl, heteroaryl, hydroxy, alkoxy, amino and alkylamino;
alternatively, $R^{23}$ and $R^{24}$ taken together with the atoms to which they are attached join to form a 4- to 7-membered ring containing 0-3 heteroatoms, wherein said 4- to 7-membered ring is optionally substituted with 1-3 substituents selected from the group consisting of $(C_1-C_6)$ alkyl, $(C_1-C_6)$heteroalkyl, hydroxy and $C(O)_2R^{26}$, wherein $R^{26}$ is hydrogen or $(C_1-C_4)$alkyl;

Z is a bond; and

R³ is a member selected from the group consisting of hydrogen, halogen, alkyl, alkoxy, hydroxy, halo($C_1$-$C_6$) alkyl, heteroalkyl, —$NO_2$, —CN, —$CH_2CN$, —$SR^9$, —O—$S(O)R^9$, —$S(O)_2R^9$, and —$S(O)R^9$, wherein $R^9$ is a member selected from the group consisting of ($C_1$-$C_4$)alkyl, amino and alkylamino.

3. The compound of claim 2, wherein R² has the formula selected from the group consisting of:

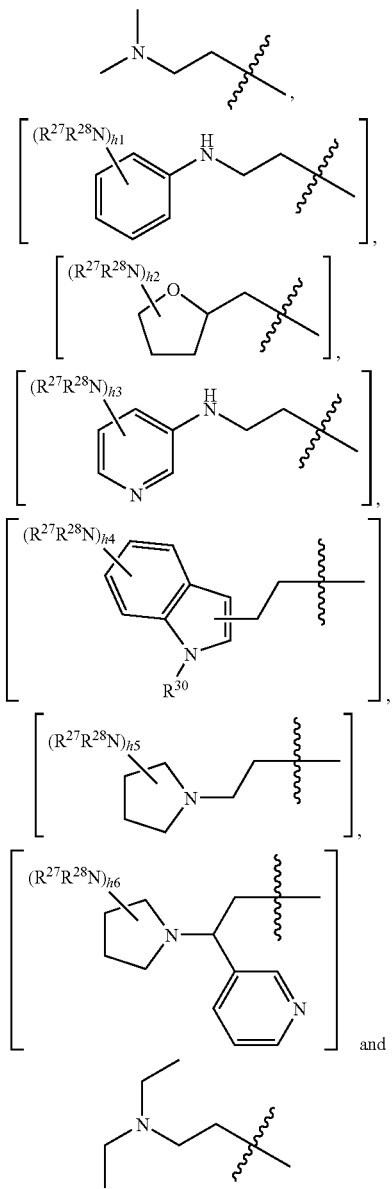

4. A compound selected from group consisting of:
6-Chloro-[1,1';4',1"]terphenyl-3-carboxylic acid (2-methoxy-pyrimidin-5-yl)-amide,
6"-Chloro-[1,1';4',1"]terphenyl-3"-carboxylic acid pyrazin-2-ylamide,
6-Chloro-3"-carboxamido-[1,1';4',1"]terphenyl-3-carboxylic acid (6-methoxy-pyridin-3-yl)-amide,
6-Chloro-[1,1';4',1"]terphenyl-3-carboxylic acid (6-methoxy-pyridin-3-yl)-amide,
6-Chloro-3"-hydroxy-[1,1';4',1"]terphenyl-3-carboxylic acid (6-methoxy-pyridin-3-yl)-amide,
6-Chloro-[1,1';4',1"]terphenyl-3-carboxylic acid (6-chloro-pyridin-3-yl)-amide,
6-Chloro-[1,1';4',1"]terphenyl-3-carboxylic acid (6-fluoro-pyridin-3-yl)-amide,
6-Chloro-[1,1';4', 1"]terphenyl-3-carboxylic acid (6-methyl-pyridin-3-yl)-amide,
6-Chloro-3"-hydroxymethyl-[1,1';4',1"]terphenyl-3-carboxylic acid (6-methoxy-pyridin-3-yl)-amide,
6-Chloro-4"-hydroxy-[1,1';4',1"]terphenyl-3-carboxylic acid (6-methoxy-pyridin-3-yl)-amide,
6-Chloro-[1,1';4',1"]terphenyl-3-carboxylic acid p-tolylamide,
6-Chloro-4"-hydroxymethyl-[1,1';4',1"]terphenyl-3-carboxylic acid (6-methoxy-pyridin-3-yl)-amide,
6-Chloro-3"-methanesulfonyl-[1,1';4',1"]terphenyl-3-carboxylic acid (6-methoxy-pyridin-3-yl)-amide,
6"-Chloro-[1,1';4',1"]terphenyl-3"-carboxylic acid [1,2,4]triazin-3-ylamide,
6-Chloro-[1,1';4',1"]terphenyl-3-carboxylic acid (2-pyrrolidin-1-yl-ethyl)-amide,
5-Fluoro-[1,1';4',1"]terphenyl-3-carboxylic acid (6-methoxy-pyridin-3-yl)-amide,
6-Methyl-[1,1';4',1"]terphenyl-3-carboxylic acid (6-methoxy-pyridin-3-yl)-amide,
6"-Chloro-2'-fluoro-[1,1';4',1"]terphenyl-3"-carboxylic acid pyridin-3-ylamide,
6-Chloro-[1,1';4',1"]terphenyl-3-carboxylic acid (2-pyridin-3-yl-2-pyrrolidin-1-yl -ethyl)-amide,
6"-Chloro-[1,1';4',1"]terphenyl-3"-carboxylic acid (4,5-dihydro-thiazol-2-yl)-amide,
6"-Chloro-4-dimethylaminomethyl-[1,1';4',1"]terphenyl-3"-carboxylic acid (6-methoxy-pyridin-3-yl)-amide,
6-Chloro-[1,1';4',1"]terphenyl-3-carboxylic acid (2-diethylamino-ethyl)-amide,
6"-Chloro-[1,1';4',1"]terphenyl-3"-carboxylic acid (6-piperazin-1-yl-pyridin-3-yl)-amide,
6-Chloro-[1,1';4',1"]terphenyl-3-carboxylic acid pyrimidin-4-ylamide,
6-Chloro-[1,1';4',1"]terphenyl-3-carboxylic acid 3-aminomethyl-benzylamide,
4-Methyl-piperazine-1-carboxylic acid 2-chloro-5-(6-methoxy-pyridin-3-ylcarbamoyl)-[1,1';4',1"]terphenyl-4"-yl ester,
6-Chloro-[1,1';4',1"]terphenyl-3-carboxylic acid (piperidin-4-ylmethyl)-amide,
6-Chloro-[1,1';4',1"]terphenyl-3-carboxylic acid (6-hydroxymethyl-pyridin-3-yl)-amide,
6-Chloro-[1,1';4',1"]terphenyl-3-carboxylic acid piperidin-4-ylamide,
6-Chloro-[1,1 ';4',1"]terphenyl-3-carboxylic acid (6-methylsulfanyl-pyridin-3-yl)-amide,
6-Chloro-[1,1';4',1"]terphenyl-3-carboxylic acid [6-(4-methyl-piperazin-1-yl)-pyridin-3-yl]-amide,
6-Methyl-[1,1';4',1"]terphenyl-3-carboxylic acid (5-chloro-pyridin-2-yl)-amide,
6-Chloro-[1,1';4',1"]terphenyl-3-carboxylic acid (5-phenyl-[1,3,4]oxadiazol-2-yl)-amide,
6-Chloro-3"-dimethylaminomethyl-[1,1';4',1"]terphenyl-3-carboxylic acid (4-methoxy-phenyl)-amide,
6-Chloro-[1,1';4',1"]terphenyl-3-carboxylic acid (2-dimethylamino-ethyl)-pyridin-3-yl-amide,
6"-Chloro-[1,1';4',1"]terphenyl-3"-carboxylic acid (6-methanesulfonyl-benzothiazol-2-yl)-amide,
6-Chloro-[1,1';4',1"]terphenyl-3-carboxylic acid (tetrahydro-furan-2-ylmethyl)-amide, 6-Chloro-[1,1';4',1"]terphenyl-3-yl)-(3-dimethylamino-pyrrolidin-1-y-1)-methanone,
6"-Chloro-[1,1';4',1"]terphenyl-3"-carboxylic acid [3-(2-methyl-[1,3]dioxolan-2-yl)-phenyl]-amide,
4"-Benzyloxy-6-chloro-[1,1';4',1"]terphenyl-3-carboxylic acid (6-methoxy-pyridin-3-yl)-amide,
6-Chloro-[1,1';4',1"]terphenyl-3-carboxylic acid pyridin-3-ylamide,
6-Chloro-[1,1';4',1"]terphenyl-3-carboxylic acid (furan-2-ylmethyl)-amide,
6"-Chloro-[1,1';4',1"]terphenyl-3"-carboxylic acid quinolin-6-ylamide,
6-Chloro-[1,1';4',1"]terphenyl-3-carboxylic acid (3-fluoro-4-methoxy-phenyl)-amide,
6-Chloro-[1,1';4',1"]terphenyl-3-carboxylic acid [6-(2-dimethylamino-ethylsulfanyl)-pyridin-3-yl]-amide,
2-Chloro-5-(6-methoxy-pyridin-3-ylcarbamoyl)-[1,1';4',1"]terphenyl-3"-carboxylic acid,
4"-Aminomethyl-6-chloro-[1,1';4',1"]terphenyl-3-carboxylic acid (6-methoxy-pyridin-3-yl)-amide,
6-Chloro-3"-formyl-[1,1';4',1"]terphenyl-3-carboxylic acid (6-methoxy-pyridin-3-yl)-amide,
6-Chloro-[1,1';4',1"]terphenyl-3-carboxylic acid methyl-(2-pyridin-2-yl-ethyl)-amide,
6-Chloro-[1,1';4',1"]terphenyl-3-carboxylic acid (2-methylsulfanyl-pyrimidin-5-yl)-amide,
6"-Chloro-[1,1';4',1"]terphenyl-3"-carboxylic acid (5-chloro-pyrimidin-2-yl)-amide,
6"-Chloro-[1,1';4',1"]terphenyl-3"-carboxylic acid (4-ethoxy-phenyl)-amide,
(3-Amino-pyrrolidin-1-yl)-(6-chloro-[1,1';4',1"]terphenyl-3-yl)-methanone,
[1,1';4',1"]terphenyl-3"-carboxylic acid (2-pyrrolidin-1-yl-ethyl)-amide,
6-Chloro-[1,1';4',1"]terphenyl-3-carboxylic acid [3-(2-morpholin-4-yl-acetylamino)-phenyl]-amide,
6-Chloro-[1,1';4',1"]terphenyl-3-carboxylic acid [4-(2-morpholin-4-yl-acetylamino)-phenyl]-amide,
6-Chloro-[1,1';4',1"]terphenyl-3-carboxylic acid [1-(2-bromo-acetyl)-piperidin-4-ylmethyl]-amide,
6"-Chloro-[1,1';4',1"]terphenyl-3"-carboxylic acid (3-methyl-isoxazol-5-yl)-amide,
6-Chloro-[1,1';4',1"]terphenyl-3-carboxylic acid (5-bromo-pyridin-2-yl)-amide,
6"-Chloro-[1,1';4',1"]terphenyl-3"-carboxylic acid (6-morpholin-4-yl-pyridin-3-yl)-amide,
6-Chloro-[1,1';4',1"]terphenyl-3-carboxylic acid (6-dimethylaminomethyl-pyridin-3-yl)-amide,
6-Chloro-[1,1';4',1"]terphenyl-3-carboxylic acid (6-trifluoromethyl-pyridin-3-yl)-amide,
6-Fluoro-[1,1';4',1"]terphenyl-3-carboxylic acid (6-methoxy-pyridin-3-yl)-amide,
6"-Chloro-2'-fluoro-[1,1';4',1"]terphenyl-3"-carboxylic acid (2-pyrrolidin-1-yl-ethyl)-amide,
6-Chloro-[1,1';4',1"]terphenyl-3-carboxylic acid (2-dimethylamino-ethyl)-amide,
6"-Chloro-[1,1';4',1"]terphenyl-3"-carboxylic acid (3-methoxy-phenyl)-amide,
[1-(6-Chloro-[1,1';4',1"]terphenyl-3-carbonyl)-pyrrolidin-3-yl]-carbamic acid tert-butyl ester,
6-Chloro-[1,1';4',1"]terphenyl-3-carboxylic acid (5-methyl-isoxazol-3-yl)-amide,
6-Chloro-[1,1';4',1"]terphenyl-3-carboxylic acid (6-ethenesulfinyl-pyridin-3-yl)-amide,
6-Chloro-2"-dimethylaminomethyl-[1,1';4',1"]terphenyl-3-carboxylic acid (6-methoxy-pyridin-3-yl)-amide,
6-Chloro-[1,1';4',1"]terphenyl-3-carboxylic acid (1-carbamimidoyl-piperidin-4-yl)-amide,
6-Chloro-[1,1';4',1"]terphenyl-3-carboxylic acid (2-cyano-ethyl)-amide,
6"-Chloro-2'-fluoro-[1,1';4',1"]terphenyl-3"-carboxylic acid pyrazin-2-ylamide,
6-Chloro-[1,1';4',1"]terphenyl-3-carboxylic acid (2-pyridin-3-yl-ethyl)-amide,
6"-Chloro-[1,1';4',1"]terphenyl-3"-carboxylic acid (4-cyano-phenyl)-amide,
6-Chloro-[1,1';4',1"]terphenyl-3-carboxylic acid [2-(1H-imidazol-4-yl)-ethyl]-pyrrolidin-2-ylmethyl-amide,
[1-(6-Chloro-[1,1';4',1"]terphenyl-3-carbonyl)-piperidin-4-ylmethyl]-carbamic acid tert-butyl ester,
6-Methoxy-[1,1';4',1"]terphenyl-3-carboxylic acid (6-methoxy-pyridin-3-yl)-amide,
6"-Chloro-[1,1';4',1"]terphenyl-3"-carboxylic acid (6-dimethylamino-pyridin-3-yl)-amide,
6"-Chloro-[1,1';4',1"]terphenyl-3"-carboxylic acid quinolin-8-ylamide,
6"-Chloro-2'-fluoro-[1,1';4',1"]terphenyl-3"-carboxylic acid (piperidin-4-ylmethyl)-amide,
6"-Chloro-[1,1';4',1"]terphenyl-3"-carboxylic acid (3-acetyl-phenyl)-amide,
6"-Chloro-[1,1';4',1"]terphenyl-3"-carboxylic acid benzo[1,3]dioxol-5-ylamide,
6-Chloro-[1,1';4',1"]terphenyl-3-carboxylic acid (3,4,5-trimethoxy-phenyl)-amide,
6-Chloro-4"-methanesulfonyl-[1,1';4',1"]terphenyl-3-carboxylic acid (6-methoxy-pyridin-3-yl)-amide,
(6-Chloro-[1,1';4',1"]terphenyl3-yl)-[1,4]diazepan-1-yl-methanone,
6-Chloro-[1,1';4',1"]terphenyl-3-carboxylic acid pyridin-4-ylamide,
6-Hydroxy-[1,1';4',1"]terphenyl-3-carboxylic acid (6-methoxy-pyridin-3-yl)-amide,
(3-{[(6-Chloro-[1,1';4',1"]terphenyl-3-carbonyl)-amino]-methyl}-benzyl)-carbamic acid tert-butyl ester,
6"-Chloro-[1,1';4',1"]terphenyl-3"-carboxylic acid [4-(acetyl-methyl-amino)-phenyl]-amide,
6-Chloro-[1,1';4',1"]terphenyl-3-carboxylic acid (2-methanesulfonyl-pyrimidin-5-yl)-amide,
6-Chloro-3",4",5"-methanesulfonyl-[1,1';4',1"]terphenyl-3-carboxylic acid (6-methoxy-pyridin-3-yl)-amide,
6-Chloro-[1,1';4',1"]terphenyl-3-carboxylic acid (6-methanesulfinyl-pyridin-3-yl)-amide,
6"-Chloro-[1,1';4',1"]terphenyl-3"-carboxylic acid cyclopentylamide,
6-Chloro-[1,1';4',1"]terphenyl-3-carboxylic acid {2-[4-(3-chloro-5-trifluoromethyl-pyridin-2-yl)-piperazin-1-yl]-ethyl}-amide,
(6-Chloro-[1,1';4',1"]terphenyl-3-yl)-(3-pyridin-4-yl-pyrrolidin-1-y-1)-methanone,
6-Chloro-[1,1';4',1"]terphenyl-3-carboxylic acid (pyridin-4-ylmethyl)-amide,
6"-Chloro-[1,1';4',1"]terphenyl-3"-carboxylic acid (3-phenyl-[1,2,4]thiadiazol-5-yl)-amide,
6"-Chloro-[1,1';4',1"]terphenyl-3"-carboxylic acid (5-trifluoromethyl-[1,3,4]thiadiazol-2-yl)-amide,
6"-Chloro-[1,1';4',1"]terphenyl-3"-carboxylic acid (4-methanesulfonyl-phenyl)-amide,
(6-Chloro-[1,1';4',1"]terphenyl-3-yl)-piperazin-1-yl-methanone,
4-(6-Chloro-[1,1';4',1"]terphenyl-3-carbonyl)-piperazine-1-carboxamidine,
6-Chloro-[1,1';4',1"]terphenyl-3-carboxylic acid (3-chloro-4-methoxy-phenyl)-amide, 6-Chloro-[1,1';4',1"]terphenyl-3-carboxylic acid (6-methyl-1-oxy-pyridin-3-yl)-amide,
6"-Chloro-[1,1';4',1"]terphenyl-3"-carboxylic acid (2,2,2-trifluoro-ethyl)-amide,
6-Chloro-[1,1';4',1"]terphenyl-3-carboxylic acid pyridin-2-ylamide,
6"-Chloro-[1,1';4',1"]terphenyl-3"-carboxylic acid (4-acetyl-phenyl)-amide,
6"-Chloro-[1,1';4',1"]terphenyl-3"-carboxylic acid (3-methylsulfanyl-phenyl)-amide,
4-[(6-Chloro-[1,1';4',1"]terphenyl-3-carbonyl)-amino]-benzoic acid methyl ester,
6-Chloro-[1,1';4',1"]terphenyl-3-carboxylic acid (6-methoxy-pyrimidin-4-yl)-amide,
6"-Chloro-[1,1';4',1"]terphenyl-3"-carboxylic acid (5-ethyl-[1,3,4]thiadiazol-2-yl)-amide,
[(6"-Chloro-[1,1';4',1"]terphenyl-3"-carbonyl)-phenyl-amino]-acetic acid ethyl ester,
4-Methyl-piperazine-1-carboxylic acid 5-(6-methoxy-pyridin-3-ylcarbamoyl)-[1,1';4',1"]terphenyl-2-yl ester,
6-Chloro-[1,1';4',1"]terphenyl-3-carboxylic acid (2-pyridin-3-yl-ethyl)-amide,
6-Chloro-[1,1';4',1"]terphenyl-3-carboxylic acid (6-methoxy-1-oxy-pyridin-3-yl)-amide,
6"-Chloro-[1,1';4',1"]terphenyl-3"-carboxylic acid benzo[1,2,5]thiadiazol-4-ylamide,
(4-Aminomethyl-piperidin-1-yl)-(6-chloro-[1,1';4',1"]terphenyl-3-yl)-methanone,
6-Chloro-[1,1';4',1"]terphenyl-3-carboxylic acid (6-methanesulfonyl-pyridin-3-yl)-amide,
Methanesulfonic acid 5-(6-methoxy-pyridin-3-ylcarbamoyl)-[1,1';4',1"]terphenyl-2-yl ester,
6"-Chloro-[1,1';4',1"]terphenyl-3"-carboxylic acid (4-cyanomethyl-phenyl)-amide,
6-Chloro-[1,1';4',1"]terphenyl-3-carboxylic acid (6-ethenesulfonyl-pyridin-3-yl)-amide,
1-(6"-Chloro-[1,1';4',1"]terphenyl-3"-carbonyl)-piperidine-4-carboxylic acid ethyl ester,
6-Chloro-[1,1';4',1"]terphenyl-3-carboxylic acid (4-chloro-phenyl)-amide,
6-Chloro-[1,1';4',1"]terphenyl-3-carboxylic acid (3,4-dichloro-phenyl)-amide,
{(2-[(6"-Chloro-[1,1';4',1"]terphenyl-3"-carbonyl)-amino]-thiazol-4-yl}-methoxyimino-acetic acid ethyl ester,
6"-Chloro-[1,1';4',1"]terphenyl-3"-carboxylic acid (2-chloro-5-cyano-phenyl)-amide,
6"-Chloro-[1,1';4',1"]terphenyl-3"-carboxylic acid (3-ethoxy-phenyl)-amide,
4-(6-Chloro-[1,1';4',1"]terphenyl-3-carbonyl)-[1,4]diazepane-1-carboxamidine,
{2-[(6-Chloro-[1,1';4',1"]terphenyl-3-carbonyl)-amino]-ethyl}-trimethyl-ammonium,
6"-Chloro-[1,1';4',1"]terphenyl-3"-carboxylic acid isoquinolin-5-ylamide,
(6-Chloro-[1,1';4',1"]terphenyl-3-yl)-(2-pyridin-4-yl-pyrrolidin-1-yl)-methanone,
6-Chloro-[1,1';4',1"]terphenyl-3-carboxylic acid (pyridin-3-ylmethyl)-amide,
6"-Chloro-[1,1';4',1"]terphenyl-3"-carboxylic acid (3,4-dimethyl-isoxazol-5-yl)-amide,
3-[(6"-Chloro-[1,1';4',1"]terphenyl-3"-carbonyl)-amino]-pyrazine-2-carboxylic acid methyl ester,
6"-Chloro-[1,1';4',1"]terphenyl-3"-carboxylic acid (3,5-dimethoxy-phenyl)-amide,
6-Chloro-[1,1';4',1"]terphenyl-3-carboxylic acid (4-chloro-phenyl)-methyl-amide,
4-[(6-Chloro-[1,1';4',1"]terphenyl-3-carbonyl)-amino]-piperidine-1-carboxylic acid tertbutyl ester,
6-Chloro-[1,1';4',1"]terphenyl-3-carboxylic acid (1H-imidazol-4-ylmethyl)-amide,
6-Chloro-[1,1';4',1"]terphenyl-3-carboxylic acid (5-methylsulfanyl-[1,3,4]thiadiazol-2-yl)-amide,
6-Chloro-[1,1';4',1"]terphenyl-3-carboxylic acid (pyridin-2-ylmethyl)-amide,
2-(6-Chloro-[1,1';4',1"]terphenyl-3-carbonyl)-1,2,3,4-tetrahydro-iso-quinoline-3-carboxylic acid [2-(1H-imidazol-4-yl)-ethyl]-amide,
6-Chloro-[1,1';4',1"]terphenyl-3-carboxylic acid {5-amino-2-[2-(1H-imidazol-4-yl)-ethylcarbamoyl]-indan-2-yl}-amide,
2-(6-Chloro-[1,1';4',1"]terphenyl-3-carbonyl)-1,2,3,4-tetrahydro-iso-quinoline-3-carboxylic acid {2-cyclohexyl-1-[2-(1H-imidazol-4-yl)-ethylcarbamoyl]-ethyl}-amide,
6-Chloro-[1,1';4',1"]terphenyl-3-carboxylic acid [1,3,4]thiadiazol-2-ylamide,
6-Chloro-[1,1';4',1"]terphenyl-3-carboxylic acid (2-pyridin-4-yl-ethyl)-amide,
6-Chloro-[1,1';4',1"]terphenyl-3-carboxylic acid {1-[2-(1H-imidazol-4-yl)-ethylcarbamoyl]-3-phenyl-propyl}-amide,
6"-Chloro-[1,1';4',1"]terphenyl-3"-carboxylic acid (2-chloro-pyridin-3-yl)-amide,
6-Chloro-[1,1';4',1"]terphenyl-3-carboxylic acid (6-chloro-pyridazin-3-yl)-amide,
6"-Chloro-[1,1';4',1"]terphenyl-3"-carboxylic acid (4-methoxy-phenyl)-methyl-amide,
3-[(6"-Chloro-[1,1';4',1"]terphenyl-3"-carbonyl)-amino]-benzoic acid ethyl ester,
6-Chloro-[1,1';4',1"]terphenyl-3-carboxylic acid (5-methyl-[1,3,4]thiadiazol-2-yl)-amide,
6-Chloro-[1,1';4',1"]terphenyl-3-carboxylic acid (1-azabicyclo[2.2.2]oct-3-yl)-amide,
(6-Chloro-[1,1';4',1"]terphenyl-3-yl)-(5-nitro-2,3-dihydro-indol-1-y-1)-methanone,
2-[(5"-Chloro-2'-fluoro-[1,1';4',1"]terphenyl-2"-carbonyl)-amino]-3-cyclohexyl-propionic acid,
6"-Chloro-[1,1';4',1"]terphenyl-3"-carboxylic acid [2-(2,5-dioxo-pyrrolidin-1-yl)-phenyl]-amide,
(6"-Chloro-[1,1';4',1"]terphenyl-3"-yl)-(4-phenyl-piperazin-1-yl)-methanone,
6"-Chloro-[1,1';4',1"]terphenyl-3"-carboxylic acid benzo[1,3]dioxol-5-yl-ethyl-amide,
6"-Chloro-[1,1';4',1"]terphenyl-3"-carboxylic acid [4-(4-nitro-benzenesulfonyl)-phenyl]-amide,
4-[(6"-Chloro-[1,1';4',1"]terphenyl-3"-carbonyl)-amino]-benzoic acid ethyl ester,
{4-[(6"-Chloro-[1,1';4',1"]terphenyl-3"-carbonyl)-amino]-phenyl}-acetic acid ethyl ester,
2-{2-[(6-Chloro-[1,1';4',1"]terphenyl-3-carbonyl)-amino]-4-phenyl-butyrylamino}-4-phenyl-butyric acid,
6-Chloro-[1,1';4',1"]terphenyl-3-carboxylic acid (3-amino-propyl)-amide,
2-[(5"-Chloro-2'-fluoro-[1,1';4',1"]terphenyl-2"-carbonyl)-amino]-4-phenyl-butyric acid,
3-(6-Chloro-[1,1';4',1"]terphenyl-3-carbonyl)-thiazolidine-4-carboxylic acid,
6"-Chloro-[1,1';4',1"]terphenyl-3"-carboxylic acid (5-cyclopropyl-[1,3,4]thiadiazol-2-yl)-amide,
6"-Chloro-[1,1';4',1"]terphenyl-3"-carboxylic acid (4-cyano-naphthalen-1-yl)-amide, 2-{2-[(6-Chloro-[1,1';4',1"]terphenyl-3-carbonyl)-amino]-4-phenyl-butyrylamino}-3-cyclohexyl-propionic acid,
6-Chloro-[1,1';4',1"]terphenyl-3-carboxylic acid [2-(1H-imidazol-4-yl)-ethyl]-piperidin-4-ylmethyl-amide,
6"-Chloro-[1,1';4',1"]terphenyl-3"-carboxylic acid (2-benzenesulfonyl-phenyl)-amide,
2-{[2-(6-Chloro-[1,1';4,'1"]terphenyl-3-carbonyl)-1,2,3,4-tetrahydro-isoquinoline-3-carbonyl]-amino}-3-(1H-imidazol-4-yl)-propionic acid,
3-(6-Chloro-[1,1';4',1"]terphenyl-3-carbonyl)-thiazolidine-4-carboxylic acid,
2-{[2-(6-Chloro-[1,1';4',1"]terphenyl-3-carbonyl)-1,2,3,4-tetrahydro-isoquinoline-3-carbonyl]-amino}-3-(1H-imidazol4-yl)-propionic acid,
6-Fluoro-[1,1';4',1"]terphenyl-3-carboxylic acid (6-methoxy-pyridin-3-yl)-amide,
(6"-Chloro-[1,1';4',1"]terphenyl-3"-yl)-(6-nitro-2,3-dihydro-indol-1-yl)-methanone,
8-(6"-Chloro-[1,1';4',1"]terphenyl-3"-carbonyl)-4-methyl-5,6,7,8-tetrahydro-1-oxa-8-aza-anthracen-2-one,
1-(6-Chloro-[1,1';4',1"]terphenyl-3-carbonyl)-octahydro-indole-2-carboxylic acid,
4-[(6-Chloro-[1,1';4',1"]terphenyl-3-carbonyl)-amino]-tetrahydro-pyran4-carboxylic acid,
1-[(6-Chloro-[1,1';4',1"]terphenyl-3-carbonyl)-amino]-4-hydroxy-cyclohexanecarboxylic acid,
4-[(6-Chloro-[1,1';4',1"]terphenyl-3-carbonyl)-amino]-piperidine-4-carboxylic acid,
1-[(6-Chloro-[1,1';4',1"]terphenyl-3-carbonyl)-amino]-3-hydroxy-cyclopentanecarboxylic acid,
6-Chloro-[1,1';4',1"]terphenyl-3-carboxylic acid (6-hydroxymethyl-pyridin-3-yl)-amide,
6-Chloro-[1,1';4',1"]terphenyl-3-carboxylic acid N'-pyridin-2-yl-hydrazide,
N'-(6-Chloro-[1,1';4',1 "]terphenyl-3-carbonyl)-hydrazinecarboxylic acid 9H-fluoren-9-ylmethyl ester,
6-Chloro-[1,1';4',1"]terphenyl-3-carboxylic acid hydrazide,
6-Chloro-[1,1';4',1"]terphenyl-3-carboxylic acid [1,2,4] triazol-1-ylamide,
2-{2-[(6-Chloro-[1,1';4',1"]terphenyl-3-carbonyl)-amino]-4-phenyl-butyrylamino}-3-cyclohexyl-propionic acid,
6'-Chloro-[1,1';4',1"]terphenyl-3"-carboxylic acid (4-methoxy-phenyl)-amide,
6-Chloro-[1,1';4',1"]terphenyl-3-carboxylic acid (1-{2-cyclohexyl-1-[2-(1H-imidazol-4-yl)-ethylcarbamoyl]-ethylcarbamoyl}-3-phenyl-propyl)-amide,
2-{2-[(6-Chloro-[1,1';4',1"]terphenyl-3-carbonyl)-amino]-4-phenyl-butyrylamino}-3-(1H-imidazol-4-yl)-propionic acid,
6-Chloro-[1,1';4',1"]terphenyl-3-carboxylic acid [6-(4-methyl-piperazin-1-ylmethyl)-pyridin-3-yl]-amide,
{2-[(6"-Chloro-[1,1';4',1"]terphenyl-3"-carbonyl)-amino-thiazol-4-yl}-acetic acid ethyl ester,
6"-Chloro-[1,1';4',1 "]terphenyl-3"-carboxylic acid cyclopropylmethyl-amide,
6"-Chloro-[1,1';4',1"]terphenyl-3"-carboxylic acid cyclopropylamide,
2-[(6"-Chloro-[1,1';4',1"]terphenyl-3"-carbonyl)-amino]-indan-2-carboxylic acid,
2-[(6"-Chloro-[1,1';4',1"]terphenyl-3"-carbonyl)-methylamino]-propionic acid,
1-[(6"-Chloro-[1,1';4',1"]terphenyl-3"-carbonyl)-amino]-cyclopropanecarboxylic acid,
3-[(6"-Chloro-[1,1';4',1"]terphenyl-3"-carbonyl)-amino]-propionic acid,
{3-[(6-Chloro-[1,1 ';4',1"]terphenyl-3-carbonyl)-amino]-propyl}-carbamic acid tert-butyl ester,
4-{[(6-Chloro-[1,1';4',1"]terphenyl-3-carbonyl)-amino]-methyl}-piperidine-1-carboxylic acid tert-butyl ester,
2-(6"-Chloro-[1,1';4',1"]terphenyl-3"-carbonyl)-1,2,3,4-tetrahydro-isoquinoline-1-carboxylic acid, and
6-Chloro-[1,1';4',1"]terphenyl-3-carboxylic acid (6-fluoro-pyridin-3-yl)-amide.

5. The compound of claim 4, wherein said compound is selected from the group consisting of: